United States Patent [19]

Petre

[11] Patent Number: 4,898,176
[45] Date of Patent: Feb. 6, 1990

[54] CONTINUOUS CARDIAC OUTPUT BY IMPEDANCE MEASUREMENTS IN THE HEART

[75] Inventor: John H. Petre, Cleveland Heights, Ohio

[73] Assignee: The Cleveland Clinic Foundation, Cleveland, Ohio

[21] Appl. No.: 210,095

[22] Filed: Jun. 22, 1988

[51] Int. Cl.⁴ .......................... A61B 5/04; A61B 5/02
[52] U.S. Cl. .................................... 128/642; 128/673; 128/713
[58] Field of Search ............... 128/695, 642, 713, 692, 128/673; 361/390

[56] References Cited

U.S. PATENT DOCUMENTS 3,995,623 12/1976 Blake et al. .
4,380,237 4/1983 Newbower .
4,572,206 2/1986 Geddes et al. .
4,632,125 12/1986 Webler et al. ...................... 128/692
4,674,518 6/1987 Salo .
4,686,987 8/1987 Salo et al. .
4,721,115 1/1988 Owens .

*Primary Examiner*—Lee S. Cohen
*Assistant Examiner*—Scott Getzow
*Attorney, Agent, or Firm*—Fay, Sharpe, Beall, Fagan, Minnich & McKee

[57] ABSTRACT

A diagnostic catheter for use in measuring cardiac output in the right ventricular chamber of a heart includes a catheter body having an outer periphery and a distal section terminating in a distal end and a proximal section terminating in a proximal end. A plurality of spaced electrodes are secured to the body outer periphery along the body distal section. A plurality of electrical leads extend in the catheter body from a respective one of the electrodes to the proximal end of the catheter body. An elongated rigid member is provided for stiffening a portion of the catheter body. One end of the rigid member is located adjacent a proximal most one of a plurality of electrodes. The rigid member so locates the plurality of electrodes as to space them away from endocardial tissue. The catheter is used with a cardiac output monitoring system. Signals from the catheter are acquired by a signal conditioning and catheter control unit and, are thereafter fed to a microcomputer. The catheter and the system are used in a method for determining the instantaneous volume of blood in a heart chamber.

21 Claims, 59 Drawing Sheets

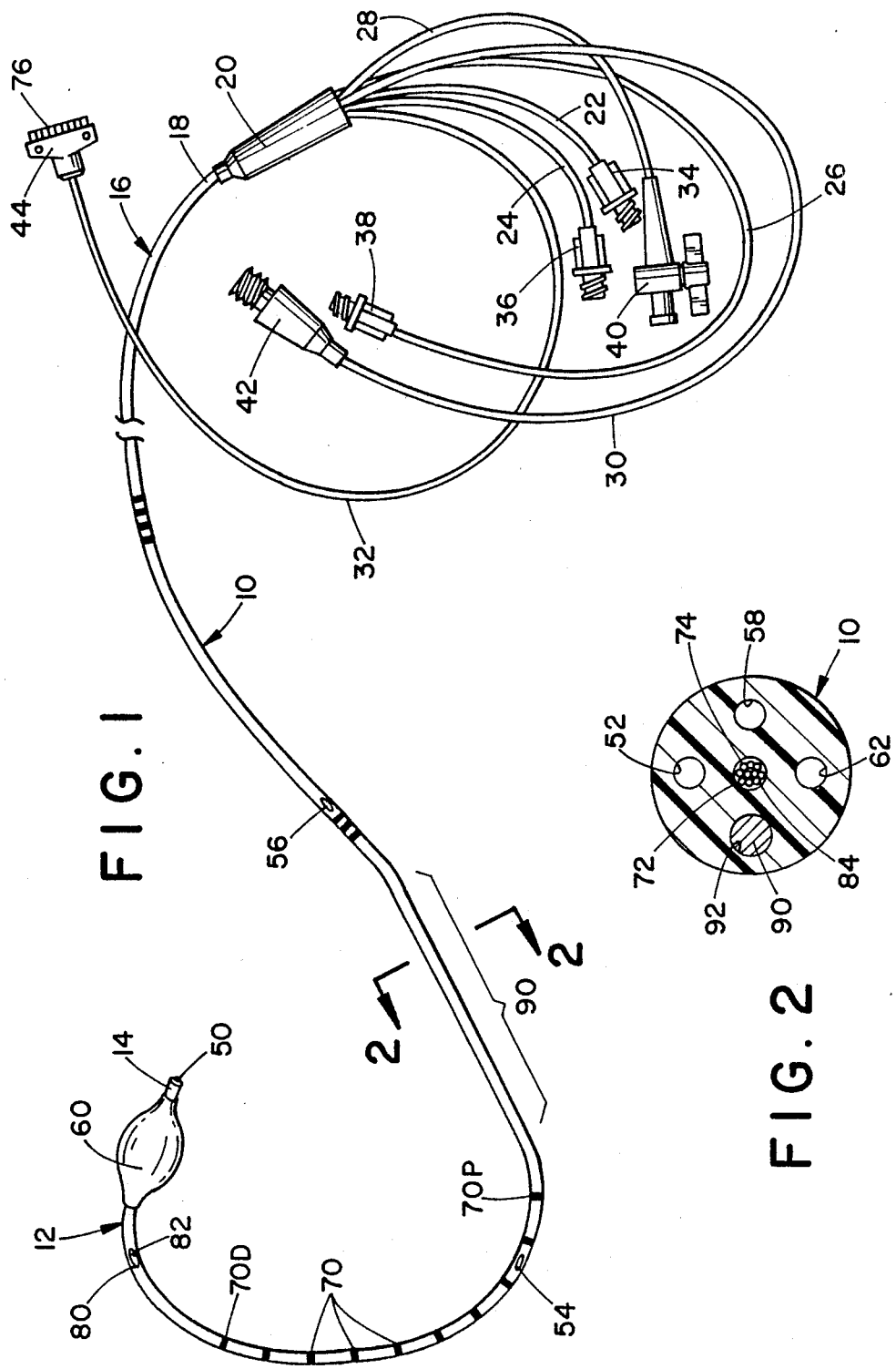

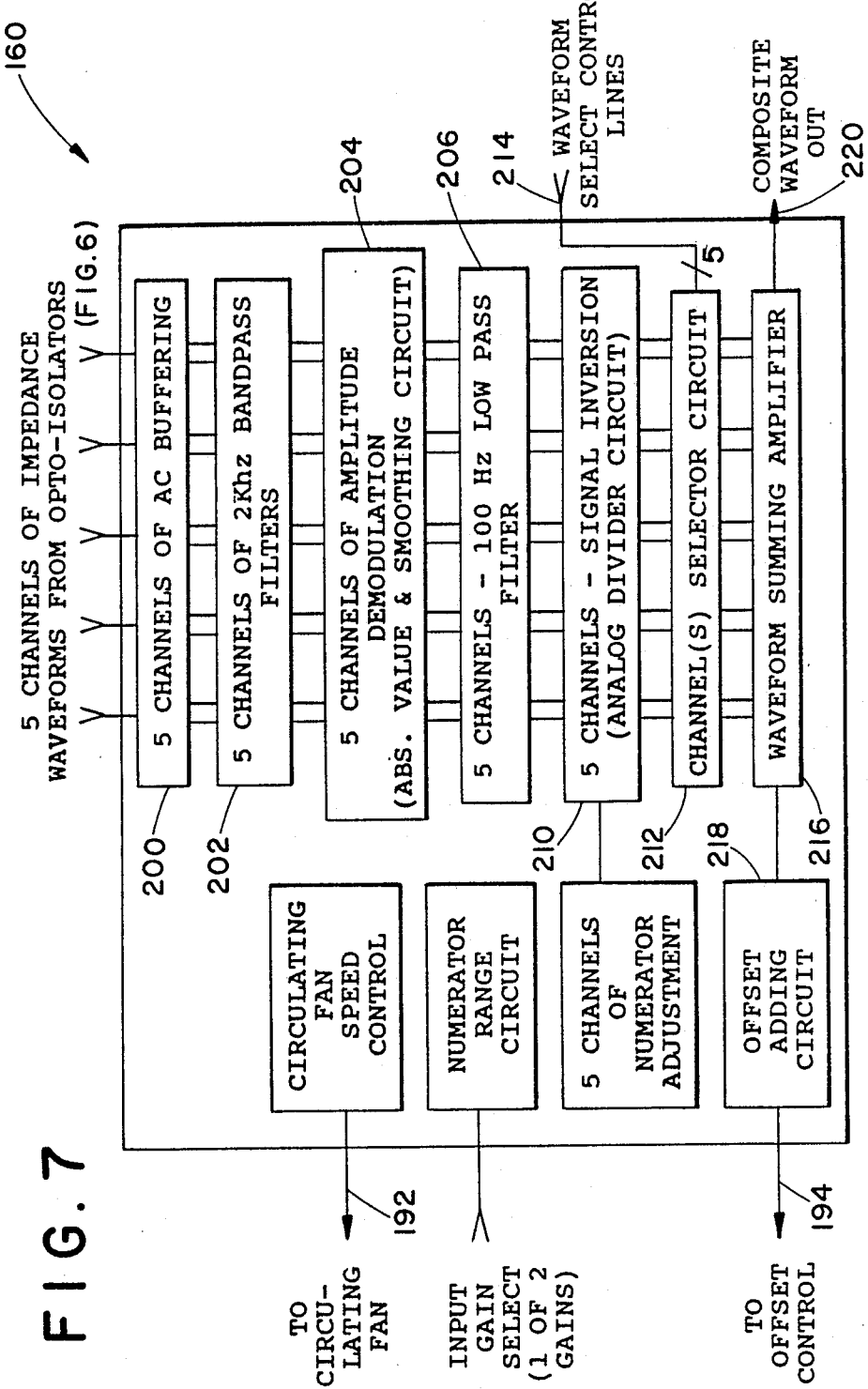

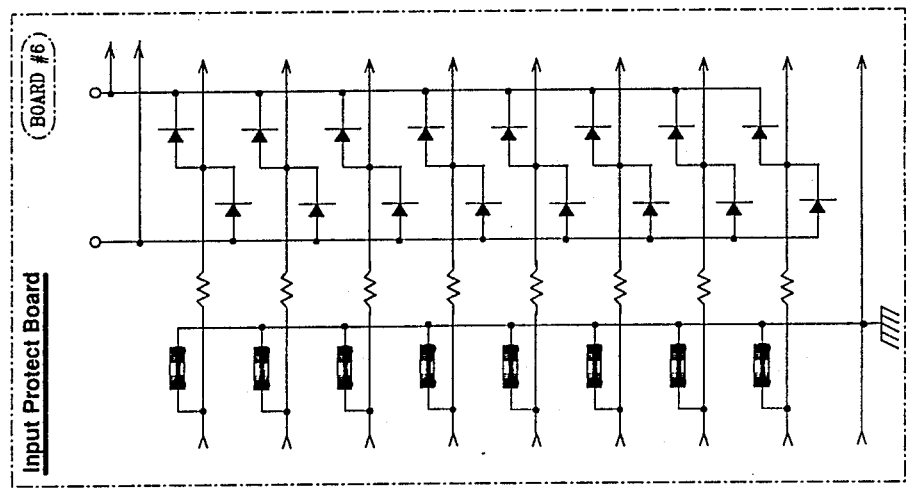
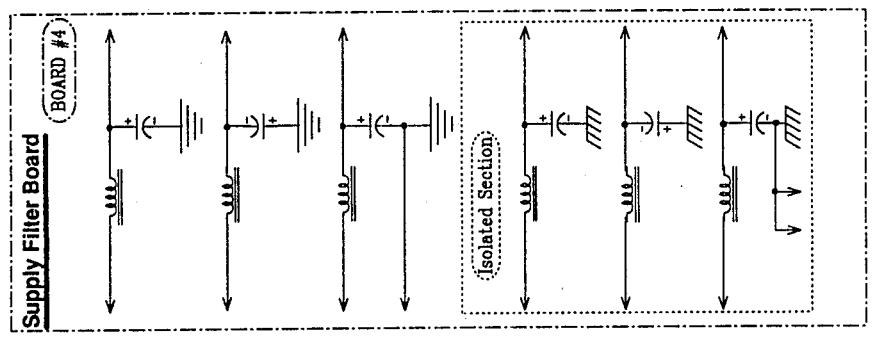
FIG. 17E

SOFTWARE LISTING
RESEARCH AND OPERATIONAL ROUTINES
FOR CCOMS

FORTH SCREEN FILES:

8086 ASSEMBLER AND FORTH LANGUAGES:

SCREEN #30
( FIRST SCREEN OF CCOC SOFTWARE            )

( SCREENS 31 THRU 34 ARE PRIMARILY ASSEMBLY LANGUAGE ROUTINES )
( THESE SCREENS SET THE ADDRESS FOR HARDWARE INTERRUPT #06 )
( THE INTERRUPT IS ACTIVE ONLY IF THE JUMPER PLUG IS INSTALLED )
( THESE SCREENS ALSO READ THE A2D PORT AND WRITE THE WAVEFORM )

( SCREENS 40 THRU 49 ARE USED TO SET THE A2D TIMER AND CHANNEL )
( ALSO TO SEND THE APPROPRIATE SCREEN CALLS TO THE VIDEO BOARD )

( TO EXECUTE: LOAD SCREEN 31, THEN LOAD 45, THEN TURN ON INT. )
( TO TURN ON INT #06 TYPE: BINARY 10110111 HEX 1B PC! OR )
( INT-ON )
( TO TURN OFF THE INT. TYPE: BINARY 11110111 HEX 1B PC! )
( THE TIMER INTERRUPT WHICH IS ALWAYS HIGH IS DISABLED BY A )
( CALL IN SCREEN 31 )

SCREEN #31
( MEMORY LOCATIONS OF VARIABLES )
FORTH DEFINITIONS
HEX
VARIABLE CARD-OUT  00 CARD-OUT ! VARIABLE RANGE  00 RANGE !
VARIABLE HRATE  00 HRATE !    VARIABLE CTS   00 CTS !
VARIABLE BUF-MAX  00 BUF-MAX ! VARIABLE BUF-MIN  00 BUF-MIN !
VARIABLE BUF-NUM  00 BUF-NUM !
( TEMPORARY ASCII DEVELOPMENT NUMBER STORAGE )
VARIABLE MHUNDS  VARIABLE MTENS  VARIABLE MONES
   00 MHUNDS ! 00 MTENS ! 00 MONES !
( ADDRESS OF REOUTINE TO WRITE ASCII VALUES TO SCREEN )
VARIABLE ADINT-RETT       VARIABLE ADQUICK1
VARIABLE ADQUICK2         VARIABLE ADOUT-CODE
VARIABLE ADSELECT-JMP     VARIABLE ADQUICK3
DECIMAL -->

FIG. 18A

SCREEN #32
( Interrupt handler compiling word      )
( —— TURN OFF TIMER 0 INTERRUPT —— )
    BINARY 11110111 HEX 1B PC!
    VARIABLE BUF-ADDRESS  VARIABLE FBUF-ADDRESS
( —— CREATE TWO - 1024 BYTE DATA BUFFERS IN MEMORY —— )
    HEX
    CREATE DATA-A2D 400 ALLOT  CREATE DATA-FIL 400 ALLOT
( — STORE THE ADDRESS OF THE BUFFER IN A MEMORY LOCATION — )
    ' DATA-A2D BUF-ADDRESS !  ' DATA-FIL FBUF-ADDRESS !
( —— MEMORY STORAGE LOCATION OF THE DATA BYTE REFERENCED — )
VARIABLE COUNTER  01 COUNTER !
( —— SET-UP A TEMPORARY STACK IN MEMORY —— )
2VARIABLE OLDSTACK
CREATE RSTACK 40 ALLOT
CREATE DSTACK 40 ALLOT        —>

SCREEN #33
( NEXT SCREEN )
HEX ASM86
( —— RETURN FROM INTERRUPT SERVICE ROUTINE —— )
  CODE INT-RETT
      AX, OLDSTACK MOV
      SS, AX MOV SP, OLDSTACK 2 + MOV
      ES POP DS POP SI POP BP POP DX POP
      CX POP BX POP AX POP  STI IRET  NEXT, END-CODE
' INT-RETT ADINT-RETT !
  CODE QUICK2
      AX, # 99 MOV  C0 , AL OUT  2$ CALL
      AX, # 00 MOV  C0 , AL OUT  2$ CALL
      BX, ADINT-RETT MOV  BX, # 02 ADD  BX JMP
2$:    AL, # C1 IN  AL, # 01 AND  AL, # 01 CMP
2$     JZ  RET
      NEXT, END-CODE  —>

SCREEN #34
( NEXT SCREEN )
  CODE QUICK3
      AX, # 84 MOV  # C0 , AL OUT  2$ CALL
      CL, # 08 MOV  AX, # 60 MOV  AX, CL ROR
      # C0 , AL OUT  2$ CALL  AX, CL ROR  # C0 , AL OUT
      2$ CALL  AX, # 190 MOV  AX, CL ROR  # C0 , AL OUT
      2$ CALL  AX, CL ROR  # C0 , AL OUT  2$ CALL
      AX, # 98 MOV  # C0 , AL OUT  2$ CALL  AX, MTENS MOV
      AX, # 30 ADD  # C0 , AL OUT  2$ CALL
      AX, # 98 MOV  # C0 , AL OUT 2$ CALL  AX, MONES MOV
      AX, # 30 ADD  # C0 , AL OUT  2$ CALL
      BX, ADINT-RETT MOV  BX, # 02 ADD  BX JMP
2$:    AX PUSH  8$: AL, # C1 IN  AL, # 01 AND  AL, # 01 CMP
      8$ JZ  AX POP RET
      NEXT, END-CODE        —>

FIG. 18B

SCREEN #35
( NEXT SCREEN )

```
        CODE QUICK1
        AX, # 99 MOV  C0 , AL OUT  2$ CALL
        AX, # 04 MOV  C0 , AL OUT  2$ CALL
        AX, # 01 MOV  BX, CARD-OUT MOV
        CX, # 48 MOV  DX, # 190 MOV
        BX PUSH  BX, ADOUT-CODE MOV  BX, # 02 ADD  BX JMP
2$:     AL, # C1 IN  AL, # 01 AND  AL, # 01 CMP  2$ JZ  RET
        NEXT, END-CODE
        ' QUICK1 ADQUICK1 !
        ' QUICK2 ADQUICK2 !
        ' QUICK3 ADQUICK3 !
-->
```

SCREEN #36
( POP ROUTINES AND NUM-WRITE SUBROUTINE )
( SUBROUTINE TO CONVERT TO ASCII AND SEND OUT DIGITAL DATA )

```
HEX    CODE OUT-CODE
       BX POP  AX PUSH
       AX, # 84 MOV  # C0 , AL OUT  2$ CALL
       AX, CX MOV  CL, # 08 MOV  AX, CL ROR
       # C0 , AL OUT  2$ CALL  AX, CL ROR
       # C0 , AL OUT  2$ CALL  AX, DX MOV
       AX, CL ROR  # C0 , AL OUT  2$ CALL  AX, CL ROR
       # C0 , AL OUT  2$ CALL
       AX, BX MOV  BX, # 64 MOV
       BL DIV  MHUNDS , AL MOV  AL, AH MOV  AH, # 00 MOV
       BX, # 0A MOV  BL DIV  MTENS , AL MOV  MONES , AH MOV
       AX, # 98 MOV  # C0 , AL OUT  2$ CALL
       AX, MHUNDS MOV  AX, # 0A CMP  4$ JAE        -->
```

SCREEN #37
( CONTINUE WITH ASCII ROUTINE )

```
       AX, # 00 CMP  5$ JG  AX, # 10 SUB
5$:    AX, # 30 ADD  # C0 , AL OUT  2$ CALL
       AX POP  AX, # 01 CMP  6$ JNAE
       AX, # 98 MOV  # C0 , AL OUT  2$ CALL
       AX, # 2E MOV  # C0 , AL OUT  2$ CALL  7$ JMP
6$:    AX, # 98 MOV  # C0 , AL OUT  2$ CALL
       AX, MTENS MOV  AX, # 30 ADD  # C0 , AL OUT  2$ CALL
       AX, # 98 MOV  # C0 , AL OUT  2$ CALL
       AX, MONES MOV  AX, # 30 ADD  # C0 , AL OUT  2$ CALL
7$:    BX, ADINT-RETT MOV
       BX, # 02 ADD  BX JMP
( HANDSHAKING SUBROUTINE FOR MICROANGELO BOARD )
2$:    AX PUSH  8$: AL, # C1 IN  AL, # 01 AND  AL, # 01 CMP
       8$ JZ  AX POP  RET          -->
```

FIG. 18C

SCREEN #38
( CONTINUATION OF ASCII CONVERSION AND SEND-OUT SCREEN )
( SUBROUTINE TO PRINT STARS IF OUT OF RANGE )
4$: AX, # 2A MOV # C0 , AL OUT 2$ CALL
  AX POP AX, # 01 CMP 7$ JZ
  AX, # 2A MOV # C0 , AL OUT 2$ CALL
  AX, # 98 MOV # C0 , AL OUT 2$ CALL
  AX, # 2A MOV # C0 , AL OUT 2$ CALL
  7$ JMP
  NEXT, END-CODE

' OUT-CODE ADOUT-CODE !
—>

SCREEN #39
( BEGIN MIN, MAX AND HRATE DETERMINATIONS  10/14/85 )
DECIMAL ( DEFINE VARIABLES )
VARIABLE LOOP-COUNTER VARIABLE MODE-TYPE 00 LOOP-COUNTER !
VARIABLE NMAX 00 NMAX !  ( # OF MAXS FOUND IN ONE BUFFER )
VARIABLE NMIN 00 NMIN !  ( # OF MINS FOUND IN ONE BUFFER )
CREATE MAX-VAL 40 ALLOT  ( ARRAY OF MAXIMUMS FOUND )
CREATE MIN-VAL 40 ALLOT  ( ARRAY OF MINIMUMS FOUND )
CREATE MAX-COUNT 40 ALLOT ( ARRAY OF COUNTER VALUES, MAXS )
CREATE MIN-COUNT 40 ALLOT ( ARRAY OF COUNTER VALUES, MINS )
VARIABLE RUN-MAX 00 RUN-MAX ! ( RUN TIME MAX, PRESENT VALUE )
VARIABLE RUN-MIN 255 RUN-MIN ! ( RUN TIME MIN, PRESENT VAL )
VARIABLE RUN-COUNT1 00 RUN-COUNT1 ! ( RUNNING MAX-COUNT )
VARIABLE RUN-COUNT2 00 RUN-COUNT2 ! ( RUNNING MIN-CONT )
VARIABLE START-MEM 00 START-MEM ! ( STARTING MEMORY LOCATION )
VARIABLE END-MEM  00 END-MEM ! ( ENDING MEMORY LOCATION )
00 MODE-TYPE ! VARIABLE BUF-OFFSET 00 BUF-OFFSET ! —>

SCREEN #40
( SECOND SCREEN - MIN, MAX AND HRATE DETERMINATION )
VARIABLE ADMIN-VAL  VARIABLE ADMIN-MAX
VARIABLE ADMIN-COUNT VARIABLE ADCALC-JMP
VARIABLE ADMAX-COUNT VARIABLE HRS VARIABLE MINS
VARIABLE ADMAX-VAL  VARIABLE SECS VARIABLE CLK_CT
' MIN-VAL 2+ ADMIN-VAL ! ' MIN-COUNT 2+ ADMIN-COUNT !
' MAX-VAL 2+ ADMAX-VAL ! ' MAX-COUNT 2+ ADMAX-COUNT !
VARIABLE AWAIT  VARIABLE CLK_VAL 00 CLK_VAL !
75 HRATE ! 00 CLK_CT ! 00 HRS ! 00 MINS ! 00 SECS !
VARIABLE ADPUT-DATA VARIABLE ADRATE-LIMITS VARIABLE ADCO-WRITE
100 BUF-NUM !  VARIABLE HRATE-CONST
VARIABLE ADRATE-CONST 15 HRATE-CONST !
VARIABLE ADSEL-JMP
—>

FIG. 18D

SCREEN #41
( FIRST SCREEN OF REAL MAX ROUTINE )
HEX
VARIABLE NMAX-OLD    VARIABLE NMIN-OLD    VARIABLE SD
    VARIABLE RUN-MAX1    VARIABLE RUN-MIN1
    VARIABLE ADREAL-MIN  VARIABLE ADREAL-MAX

CODE REAL-MAX
    DX, NMAX-OLD MOV  CX, NMAX MOV  CX, DX SUB  CX, # 00 CMP
    13$ JLE  BX, ADMAX-COUNT MOV
2$:    AX, DX MOV  AX, # 01 SHL  BX, AX ADD  AX, [BX] MOV
    BX, HRATE-CONST MOV  BX, # 01 SHR  AX, BX SUB  3$ JS
4$:    BX, BUF-ADDRESS MOV  BX, AX ADD  DX PUSH  DX, # 00 MOV
    RUN-MAX1 , DX MOV  CX PUSH  CX, HRATE-CONST MOV
5$:    AL, [BX] MOV  AH, RUN-MAX1 MOV
    AH, AL CMP  10$ JAE  RUN-MAX1 , AL MOV
-->

SCREEN #42
( SECOND SCREEN OF REAL MAX ROUTINE )
10$:  BX INC  5$ LOOP
9$:   CX POP  DX POP
    BX, ADMAX-VAL MOV  AX, DX MOV
    AX, # 01 SHL  BX, AX ADD  AX, RUN-MAX1 MOV
    [BX], AX MOV  DX INC  BX, ADMAX-COUNT MOV  2$ LOOP
13$:  1$ JMP
3$:   AX NEG  BX, HRATE-CONST MOV  AX, BX CMP  6$ JL
    BX, # 03C0 MOV  BX, AX SUB  BX, AX XCHG  4$ JMP
6$:   BX, # 03C0 MOV  BX, AX SUB  DX PUSH  CX PUSH
    CX, BUF-ADDRESS MOV  BX, CX ADD  DX, # 00 MOV
    RUN-MAX1 , DX MOV  CX, AX MOV  AX PUSH
7$:   AL, [BX] MOV  AH, RUN-MAX1 MOV
    AH, AL CMP  11$ JAE  RUN-MAX1 , AL MOV
11$:  BX INC  7$ LOOP
    BX, BUF-ADDRESS MOV  BX INC -->

SCREEN #43
( THIRD SCREEN OF REAL MAX ROUTINE )
    AX POP  CX, HRATE-CONST MOV  CX, AX SUB  CX, # 01 MOV
8$:   AL, [BX] MOV  AH, RUN-MAX1 MOV
    AH, AL CMP  12$ JAE  RUN-MAX1 , AL MOV
12$:  BX INC  8$ LOOP  9$ JMP
1$:   BX, ADINT-RETT MOV  BX, # 02 ADD  BX JMP
    NEXT, END-CODE

' REAL-MAX ADREAL-MAX !
                    -->

FIG. 18E

SCREEN #44
( FIRST SCREEN OF REAL MIN ROUTINE )

HEX

CODE REAL-MIN
  DX, NMIN-OLD MOV  CX, NMIN MOV  CX, DX SUB  CX, # 00 CMP
  13$ JLE  BX, ADMIN-COUNT MOV
2$:  AX, DX MOV  AX, # 01 SHL  BX, AX ADD  AX, [BX] MOV
  BX, HRATE-CONST MOV  BX, # 01 SHR  AX, BX SUB  3$ JS
4$:  BX, BUF-ADDRESS MOV  BX, AX ADD  DX PUSH  DX, # FF MOV
  RUN-MIN1 , DX MOV  CX PUSH  CX, HRATE-CONST MOV
  DX, # 00 MOV
5$:  AL, [BX] MOV  AH, RUN-MIN1 MOV
  AH, AL CMP  10$ JBE  RUN-MIN1 , AL MOV
-->

SCREEN #45
( SECOND SCREEN OF REAL MIN ROUTINE )

10$:  BX INC  5$ LOOP
9$:  CX POP  DX POP  BX, ADMIN-VAL MOV  AX, DX MOV
  AX, # 01 SHL  BX, AX ADD  AX, RUN-MIN1 MOV
  [BX], AX MOV  DX INC  BX, ADMIN-COUNT MOV  2$ LOOP
13$:  1$ JMP
3$:  AX NEG  BX, HRATE-CONST MOV  AX, BX CMP  6$ JL
  BX, # 03C0 MOV  BX, AX SUB  BX, AX XCHG  4$ JMP
6$:  BX, # 03C0 MOV  BX, AX SUB  DX PUSH  CX PUSH
  CX, BUF-ADDRESS MOV  BX, CX ADD  DX, # FF MOV
  RUN-MIN1 , DX MOV  CX, AX MOV  AX PUSH  DX, # 00 MOV
7$:  AL, [BX] MOV  AH, RUN-MIN1 MOV
  AH, AL CMP  11$ JBE  RUN-MIN1 , AL MOV
11$:  BX INC  7$ LOOP  BX, BUF-ADDRESS MOV  BX INC
-->

SCREEN #46
( THIRD SCREEN OF REAL MIN ROUTINE )
  AX POP  CX, HRATE-CONST MOV  CX, AX SUB
8$:  AL, [BX] MOV  AH, RUN-MIN1 MOV
  AH, AL CMP  12$ JBE  RUN-MIN1 , AL MOV
12$:  BX INC  8$ LOOP  9$ JMP
1$:  BX, ADINT-RETT MOV  BX, # 02 ADD  BX JMP
  NEXT, END-CODE

' REAL-MIN ADREAL-MIN !
DECIMAL
-->

FIG. 18F

SCREEN #47
( DEVELOP CODE TO SEND OVER DIGITAL VALUES TO VIDEO DISPLAY )
HEX  CODE SELECT-JMP
     AX, COUNTER MOV
     AX, # 23 CMP  11$ JE  AX, # 27 CMP  12$ JE
     AX, # 213 CMP 11$ JE  AX, # 217 CMP 12$ JE
     AX, # 1E1 CMP  9$ JNAE  AX, # 1E0 SUB
9$:  AX, # 170 CMP  10$ JNAE  1$ JE
     AX, # 180 CMP  2$ JE  AX, # 191 CMP  3$ JE
     AX, # 1A0 CMP  4$ JE  AX, # 1B0 CMP  5$ JE
     AX, # 1C0 CMP  6$ JE  AX, # 1D0 CMP  7$ JE  10$ JMP
10$: BX, ADINT-RETT MOV  BX, # 02 ADD  BX JMP
11$: BX, ADREAL-MAX MOV  BX, # 02 ADD  BX JMP
12$: BX, ADREAL-MIN MOV  BX, # 02 ADD  BX JMP
1$:  AX, # 00 MOV  BX, BUF-MAX MOV
     CX, # 1C8 MOV  DX, # 1C8 MOV  8$ JMP  -->

SCREEN #48
( NEXT SCREEN )
2$:  AX, # 00 MOV  BX, BUF-MIN MOV
     CX, # 1C8 MOV  DX, # 1B4 MOV  8$ JMP
3$:  AX, # 00 MOV  BX, HRATE MOV
     CX, # 1C8 MOV  DX, # 1A0 MOV  8$ JMP
4$:  AX, # 00 MOV  BX, BUF-NUM MOV
     CX, # 1C8 MOV  DX, # 18B MOV  8$ JMP
5$:  BX, ADQUICK1 MOV  BX, # 02 ADD  BX JMP
6$:  BX, ADQUICK3 MOV  BX, # 02 ADD  BX JMP
7$:  BX, ADQUICK2 MOV  BX, # 02 ADD  BX JMP
8$:  BX PUSH  BX, ADOUT-CODE MOV  BX, # 02 ADD  BX JMP
     NEXT, END-CODE
     ' SELECT-JMP ADSELECT-JMP !
: INT-ON HEX B7 1B PC! DECIMAL ;
: INT-OFF HEX F7 1B PC! DECIMAL ;       -->

SCREEN #49
( ASSEMBLER VERSION OF MIN/MAX ROUTINE     10/28/85 )
HEX CODE  MIN-MAX
     CX, # 00 MOV   DX, CTS  MOV
5$:  AX, MODE-TYPE MOV     AX, # 01 CMP  1$ JZ
     BX, START-MEM MOV     BX, CX ADD    AL, [BX] MOV
     AH, RUN-MAX MOV      AH, AL CMP    2$ JAE
     BX, BUF-OFFSET MOV    BX, CX ADD  RUN-COUNT1 , BX MOV
     RUN-MAX , AL MOV     DX, # 00 MOV  3$ JMP
2$:  AX, HRATE-CONST MOV  DX, AX CMP  4$ JL
     BX, ADMAX-COUNT MOV  CX PUSH  CX, NMAX MOV
     CX, # 01 SHL  BX, CX ADD  AX, RUN-COUNT1 MOV
     [BX], AX  MOV  CX POP
     NMAX INC        DX, # 00 MOV  RUN-MAX , DX MOV
     MODE-TYPE INC    3$ JMP
4$:  DX INC     3$ JMP     10$: 5$ JMP  -->

FIG. 18G

SCREEN #50
( ASSEMBLER VERSION OF MIN/MAX ROUTINE - SCREEN #2  10/28/85 )
1$:   BX, START-MEM MOV   BX, CX ADD    AL, [BX] MOV
      AH, RUN-MIN MOV     AH, AL CMP    7$ JBE
      BX, BUF-OFFSET MOV  BX, CX ADD  RUN-COUNT2 , BX MOV
      RUN-MIN , AL MOV    DX, # 00 MOV   3$ JMP
7$:   AX, HRATE-CONST MOV DX, AX CMP 9$ JL BX, ADMIN-COUNT MOV
      CX PUSH   CX, NMIN MOV   CX, # 10 CMP   6$ JGE
      CX, # 01 SHL   BX, CX ADD   AX, RUN-COUNT2 MOV
      [BX], AX MOV   CX POP
      NMIN INC  DX, # 00 MOV  BX, # FF MOV  RUN-MIN , BX MOV
      MODE-TYPE DEC       3$ JMP
9$:   DX INC
3$:   CX, # 01 ADD   CX, # 1DF CMP  10$ JBE  8$ JMP
6$:   BX, # 00 MOV   NMAX , BX MOV   NMIN , BX MOV
8$:   CTS , DX MOV     BX, ADSELECT-JMP MOV  -->

SCREEN #51
( TEST SCREEN FOR MIN-MAX )
      BX, # 02 ADD  BX JMP
NEXT, END-CODE
        ' MIN-MAX ADMIN-MAX !
CODE PUT-DATA
      CX, NMAX MOV  CX, # 02 CMP  1$ JL  AX, # 00 MOV
      BX, ADMAX-VAL MOV  BX, # 02 SUB
2$:   BX, # 02 ADD  DX, [BX] MOV  AX, DX ADD  CX DEC
      CX, # 00 CMP  2$ JNE  BX, NMAX MOV  DX, # 00 MOV
      BX DIV  BX, # 05 MOV  BX MUL  BUF-MAX , AX MOV  3$ JMP
1$:   AX, # 1FFF MOV  BUF-MAX , AX MOV
3$:   CX, NMIN MOV  CX, # 02 CMP  9$ JL  AX, # 00 MOV
      BX, ADMIN-VAL MOV  BX, # 02 SUB
4$:   BX, # 02 ADD  DX, [BX] MOV  AX, DX ADD  CX DEC
      CX, # 00 CMP  4$ JNE  BX, NMIN MOV  DX, # 00 MOV  -->

SCREEN #52
( PUT-DATA ROUTINE AND RATE-LIMITS ROUTINE )
      BX DIV  BX, # 05 MOV  BX MUL  BUF-MIN , AX MOV  10$ JMP
9$:   AX, # 1FFF MOV  BUF-MIN , AX MOV
10$:  BX, ADSELECT-JMP MOV  BX, # 02 ADD  BX JMP
      NEXT, END-CODE
' PUT-DATA ADPUT-DATA !
CODE RATE-LIMITS
      AX, NMAX MOV  AX, # 02 CMP  1$ JGE  AX, NMIN MOV
      AX, # 02 CMP  1$ JGE AX, # 1FFF MOV  HRATE , AX MOV  10$ JMP
1$:   BX, ADMAX-VAL MOV  AX, [BX] MOV  BX, ADMIN-VAL MOV
      CX, [BX] MOV  AX, CX SUB  BX, # 05 MOV  AX, BX CMP
      2$ JG  BX, # 1FFF MOV  HRATE , BX MOV  10$ JMP
2$:   AX, HRATE MOV  AX, # FFFF CMP  3$ JNE  AX, # 1FFF MOV
      HRATE , AX MOV  10$ JMP  -->

FIG. 18H

SCREEN #53
( RATE-LIMITS ROUTINE )
3$:   BX, ADMAX-COUNT MOV  AX, [BX] MOV  AX, # 0352 CMP
      6$ JLE  AX, # 3C0 SUB  [BX], AX MOV

6$:   CX, NMAX MOV  CX DEC  CX PUSH  BX, ADMAX-COUNT MOV
      AX, # 00 MOV
4$:   DX, [BX] MOV  AX PUSH  BX, # 02 ADD
      AX, [BX] MOV  AX, DX SUB  DX POP  AX, DX ADD
      4$ LOOP  CX POP  DX, # 00 MOV  CX DIV  AX PUSH
      BX, ADMIN-COUNT MOV  AX, [BX] MOV  AX, # 0352 CMP
      7$ JLE  AX, # 3C0 SUB  [BX], AX MOV

7$:   CX, NMIN MOV  CX DEC  CX PUSH  BX, ADMIN-COUNT MOV
      AX, # 00 MOV      -->

SCREEN #54
( RATE-LIMITS ROUTINE )

5$:   DX, [BX] MOV  AX PUSH  BX, # 02 ADD
      AX, [BX] MOV  AX, DX SUB  DX POP  AX, DX ADD
      5$ LOOP  CX POP  DX, # 00 MOV  CX DIV  BX POP
      BX, AX ADD  DX, # 00  MOV  AX, # 5DC0 MOV  BX DIV
      HRATE , AX MOV
10$:  BX, ADSELECT-JMP MOV  BX, # 02 ADD  BX JMP
      NEXT, END-CODE
' RATE-LIMITS ADRATE-LIMITS ! -->

SCREEN #55
( CO-WRITE ROUTINE AND RATE-CONST ROUTINE )
  CODE CO-WRITE
      AX, HRATE MOV  AX, # 1FFF CMP  1$ JNE  AX, # 044C MOV
      CARD-OUT , AX MOV  2$ JMP
1$:   AX, BUF-MAX MOV  BX, BUF-MIN MOV  AX, BX SUB  BX, BUF-NUM
      MOV  BX MUL  CX, # 64 MOV  CX DIV  BX, HRATE MOV
      BX MUL  CX, # 50 MOV  CX DIV  CARD-OUT , AX MOV
2$:   BX, ADSELECT-JMP MOV  BX, # 02 ADD  BX JMP
      NEXT, END-CODE
  ' CO-WRITE ADCO-WRITE !

CODE RATE-CONST
      BX, HRATE MOV  BX, # 1FFF CMP  1$ JE  AX, # 0BB8 MOV
      DX, # 00 MOV  BX DIV  AX, # 014 CMP  2$ JL
      AX, # 064 CMP  3$ JG
      HRATE-CONST, AX MOV  1$ JMP  -->

FIG. 181

SCREEN #56
( RATE-CONST ROUTINE AND CALC-JMP ROUTINE )
```
2$:     AX, # 014 MOV  HRATE-CONST, AX MOV  1$ JMP
3$:     AX, # 064 MOV  HRATE-CONST, AX MOV  1$ JMP
1$:     BX, HRATE-CONST MOV  DX, # 3BE MOV  DX, BX SUB
        RANGE, DX MOV
        BX, ADSELECT-JMP MOV  BX, # 02 ADD  BX JMP
        NEXT, END-CODE
 ' RATE-CONST ADRATE-CONST !

CODE CALC-JMP
        AX, COUNTER MOV  BX, CLK_CT MOV  AX, # 3C0 CMP  11$ JNE
        BX, # 00 MOV  CLK_CT, BX MOV  12$ JMP
11$:    AX, BX SUB  AX, # 028 CMP  13$ JNE  BX, # 028 ADD
        CLK_CT, BX MOV
12$:    AX, CLK_VAL MOV  AX INC  AX, # 05 CMP  14$ JE
        CLK_VAL, AX MOV  13$ JMP    -->
```

SCREEN #57
( SCREEN #2 -> RATE-CONST ROUTINE AND CALC-JMP ROUTINE )
```
14$:    AX, # 00 MOV  CLK_VAL, AX MOV  AX, SECS MOV  AX INC
        AX, # 03C CMP  15$ JL  BX, # 00 MOV  SECS, BX MOV
        AX, MINS MOV  AX, # 01 AND  AX, # 01 CMP  18$ JNE
        CLK_VAL INC
18$:    AX, MINS MOV  AX INC  AX, # 03C CMP  16$ JL  MINS, BX MOV
        AX, HRS MOV  AX INC  AX, # 019 CMP  17$ JL  BX, # 01 MOV
        HRS, BX MOV  13$ JMP     15$: SECS, AX MOV  13$ JMP
16$:    MINS, AX MOV  13$ JMP     17$: HRS, AX MOV
13$:    AX, COUNTER MOV  AX, # 60 CMP  3$ JLE  AX, # 200 CMP  1$ JE
        AX, # 210 CMP  2$ JE  AX, # 220 CMP  10$ JNE
        BX, ADRATE-CONST MOV  BX, # 02 ADD  BX JMP
3$:     AX, # 10 CMP  4$ JE  AX, # 20 CMP  2$ JE
        AX, # 30 CMP  5$ JE  AX, # 40 CMP  6$ JE
        AX, # 51 CMP  7$ JE  AX, # 60 CMP  8$ JE  -->
```

SCREEN #58
( CALC-JMP ROUTINE - SCREEN #3 )
```
10$:    BX, ADSELECT-JMP MOV  BX, # 02 ADD  BX JMP
1$:     BX, # 00 MOV  BUF-OFFSET, BX MOV  NMAX, BX MOV
        NMIN, BX MOV  AX, FBUF-ADDRESS MOV  AX, # 01 ADD
        START-MEM, AX MOV  10$ JMP
2$:     BX, ADMIN-MAX MOV  BX, # 02 ADD  BX JMP
4$:     AX, FBUF-ADDRESS MOV  AX, # 01E1 ADD  START-MEM, AX MOV
        BX, # 1E0 MOV  BUF-OFFSET, BX MOV  10$ JMP
5$:     AX, RUN-COUNT1 MOV  BX, RANGE MOV  AX, BX CMP  9$ JLE
        AX, # 3C0 SUB  RUN-COUNT1, AX MOV
9$:     AX, RUN-COUNT2 MOV  BX, RANGE MOV  AX, BX CMP  10$ JLE
        AX, # 3C0 SUB  RUN-COUNT2, AX MOV  10$ JMP  -->
```

FIG. 18J

SCREEN #59
( CALC-JMP ROUTINE - SCREEN #4 )
6$:    BX, ADPUT-DATA MOV  BX, # 02 ADD  BX JMP
7$:    BX, ADRATE-LIMITS MOV  BX, # 02 ADD  BX JMP
8$:    BX, ADCO-WRITE MOV  BX, # 02 ADD  BX JMP
       NEXT, END-CODE
  ' CALC-JMP ADCALC-JMP !
CODE SEL-JMP
       AX, COUNTER MOV  AX, # 203 CMP  1$ JE  AX, # 13 CMP  2$ JE
3$:    BX, ADCALC-JMP MOV  BX, # 02 ADD  BX JMP
1$:    BX, # 00 MOV  NMAX-OLD , BX MOV  NMIN-OLD , BX MOV  3$ JMP
2$:    BX, NMAX MOV  NMAX-OLD , BX MOV  BX, NMIN MOV
       NMIN-OLD , BX MOV  3$ JMP
NEXT, END-CODE
  ' SEL-JMP  ADSEL-JMP ! -->

SCREEN #60
( SCREEN 2 OF INTERRUPT HANDLER            09/30/85 )

( SAMPLE A DATA POINT AND STORE IT IN A RING BUFFER )
HEX    CODE INT-CODE     BX, BUF-ADDRESS MOV
       CX, COUNTER MOV  AL, # B2 IN  AH, AL MOV  AL, # B4 IN
       AL, # 00 CMP  13$ JE  AX, # 00 MOV
( AT THIS POINT, THE AL REGISTER HAS THE SAMPLED DATA AND THE )
( CX REGISTER HAS THE MEMORY BUFFER COUNT )
13$:   AH, AL XCHG  BX, CX ADD
       AX PUSH  AL, [BX] MOV  AH, # 00 MOV
       DX, # 8C MOV  3$ CALL  AX POP
       [BX], AL MOV  DX, # 8D MOV  3$ CALL  AX, # 01 SHR
       AX, # 01 SHR  AX, # 01 SHR  DX, AX MOV  DX, # 01 AND
       AX, # 01 SHR  AX, DX ADD  AX PUSH  BX, FBUF-ADDRESS MOV
       BX, CX ADD  BX DEC  AL, [BX] MOV  DL, # 0F MOV
       DL MUL  AX, # 01 SHR  AX, # 01 SHR  AX, # 01 SHR  -->

SCREEN #61
( PRODUCE A FILTERRED WAVEFORM - 2 HZ LOW PASS DIGITAL FILTER )

DX, AX MOV  DX, # 01 AND
       AX, # 01 SHR  AX, DX ADD  DX POP  AX, DX ADD  BX INC
       [BX], AL MOV
       CX, # 3C0 CMP  1$ JNE  BX, FBUF-ADDRESS MOV
       [BX], AL MOV  CX, # 00 MOV
1$:    CX INC
       COUNTER , CX MOV ( JUMP TO ASCII SEND-OUT ROUTINE IF COUNT APPROPRIATE )
       BX, ADSEL-JMP MOV  BX, # 02 ADD
       BX JMP              -->

FIG. 18K

SCREEN #62
( SUBROUTINE TO OUTPUT DATA TO THE MICROANGELO VIDEO BOARD )
( ENTER HERE WITH: Y-AXIS DATA IN AL REGISTER, X-AXIS DATA )
( IN THE CX REGISTER, AND OP-CODE TO BE SENT IN THE DX REG. )
3$:   CX PUSH  AX PUSH  10$ CALL   AX PUSH
      AX, DX MOV  # C0 , AL OUT  4$ CALL
      AX, CX MOV  CL, # 08 MOV  AX PUSH
      AX, # 1E1 CMP  8$ JB  AX, # 1E0 SUB
8$:   AX, # 1E ADD
      AX, CL ROR  # C0 , AL OUT  4$ CALL
      AX, CL ROR  # C0 , AL OUT  4$ CALL
      AX POP  AX, # 1E0 CMP  AX POP  9$ JA  AX, # C8 ADD
9$:   AX, CL ROR  # C0 , AL OUT  4$ CALL
      AX, CL ROR  # C0 , AL OUT 4$ CALL  AX POP  CX POP  RET
( HANDSHAKING SUBROUTINE FOR MICROANGELO BOARD )
4$:   AX PUSH  5$: AL, # C1 IN  AL, # 01 AND  AL, # 01 CMP
      5$ JZ  AX POP  RET  -->

SCREEN #63
( LAST SCREEN OF INTERRUPT SERVICE ROUTINE        10/04/85 )

( SUBROUTINE TO LIMIT MAXIMUM Y AMPLITUDE TO 95 HEX )
10$:  AX, # 95 CMP  2$ JLE  AX, # 95 MOV
2$:   AX, # 00 CMP  7$ JNE  AX INC  7$: RET
      NEXT, END-CODE
FORTH DECIMAL

-->

SCREEN #64
( SCREEN 3 OF INTERRUPT HANDLER         09/30/85 )
FORTH    VARIABLE ADJUMP ' INT-CODE ADJUMP !
( ----- WRITE TO 0000 03F8 THE INTERRUPT VECTOR ADDRESS ---- )
        HEX ?CS: 00 03FA !L  ( STORE CURRENT SEGMENT )
        HERE 00 03F8 !L      ( STORE HERE ADDRESS )
( ----- PUSH REGISTERS AND SETUP FOR INTERRUPT SERVICE ----- )
ASSEMBLER
        AX PUSH  AH, # 31 IN  BX PUSH  CX PUSH  DX PUSH
        BP PUSH  SI PUSH  DS PUSH  ES PUSH
        AX, SS MOV  CS: OLDSTACK , AX MOV
        AX, SP MOV  CS: OLDSTACK 2 + , AX MOV
        AX, CS MOV  SS, AX MOV
        DS, AX MOV  ES, AX MOV
        SP, # DSTACK 40 + MOV  BP, # RSTACK 40 + MOV
        CLI CLD  BX, ADJUMP MOV  BX, # 02 ADD  BX JMP
FORTH DECIMAL
-->

FIG. 18L

SCREEN #65
( Set-up Routine for MicroAngelo Video display    10/01/85 )
HEX
( DATA PORT = 192 [C0 HEX]    CONTROL PORT = 193 [C1 HEX] )

( DEFINE WORD TO RESET VIDEO BOARD THROUGH PORT C1 )
: MICRO-RESET 00 C1 P! 01 C1 P! 01 C1 P! 00 C1 P! ;

( DEFINE WORD TO CHECK IF VIDEO BUFFER CLEAR TO SEND )
: PORTRDY BEGIN C1 P@ 01 AND 0= UNTIL ;

( SEND X AND Y POINTS TO VIDEO BOARD- YLOW YH XLOW XH GETPT )
: GETPT  8D C0 P! PORTRDY C0 P! PORTRDY C0 P! PORTRDY
   C0 P! PORTRDY C0 P! PORTRDY ;
-->

SCREEN #66
( #2 Set-up Routine for MicroAngelo Video display    10/01/85 )
HEX
 DATA PORT = 192 [C0 HEX]    CONTROL PORT = 193 [C1 HEX] )

( BREAK X AND Y 16 BIT VALUES INTO FOUR 8 BIT VALUES )
 : PLOTXY 100 /MOD ROT 100 /MOD GETPT ;
( USE PLOTXY AS --> XVALUE YVALUE PLOTXY )

( CLEAR VIDEO GRAPHICS SCREEN )
: CLRVID 88 C0 P! PORTRDY ;
MICRO-RESET CLRVID

DECIMAL -->

SCREEN #67
( WRITE TO SCREEN )
      HEX
( SEND X AND Y POINTS TO VIDEO BOARD- YLOW YH XLOW XH GETPT )
: GETPTT  8C C0 P! PORTRDY C0 P! PORTRDY C0 P! PORTRDY
   C0 P! PORTRDY C0 P! PORTRDY ;

: UNPLOTXY 100 /MOD ROT 100 /MOD GETPTT ;

README COUNTER @ DUP BUF-ADDRESS @ + C@
      PLOTXY ;
-->

FIG. 18M

SCREEN #68
( SET-UP SCREEN FOR TECMAR A2D BOARD - C.C.O.C.   9/25/85  )
( ------- SET-UP AM9513 TIMER FOR 200 HZ OPERATION --------- )
   HEX  FF BE P!    ( ISSUE A MASTER RESET COMMAND      )
         17 BE P!    ( POINT DATA POINTER REGISTER AT MMR )
         E0 BC P!    ( SEND LSB OF MASTER MODE REGISTER  )
         C5 BC P!    ( SEND MSB OF MASTER MODE REGISTER  )
( --- AM9513 TIMER NOW PROGRAMED FOR 200 HZ OPERATION ------ )
( ------ SET-UP A2D CONVERTER FOR INTERRUPT OPERATION ------- )
         0C B0 P!    ( SET A2D FOR LOAD ENABLE OPERATION  )
(                    ALSO ENABLE EXTERNAL STROBE        )
         00 B2 P!    ( SELECT ANALOG CHANNEL 0 FOR INPUT  )
         00 BA P!    ( CLEAR OVERRUN FLAG             )
( ------ A2D CONVERTER NOW READY TO SAMPLE INPUT CH. 0 ------ )
( INT-ON  BINARY 10110111 HEX 1B PC! )
( INT-OFF BINARY 11110111 HEX 1B PC! )        -->

SCREEN #69
( DEVELOP A RECTANGLE PLOT ROUTINE )
( -- DRAW ANY RECTANGLE - POINTS MUST BE ON STACK AS SHOWN )
( BOT --> TO TOP:  XLOW YLOW XHIGH YHIGH )      HEX
( TO IMPLEMENT; PLACE VALUES ON THE STACK WITH X,Y OF L-CORNER )
( ON BOTTOM AND X,Y OF R-CORNER ON TOP, THEN CALL RECTANGLE )
: P-T C0 P! PORTRDY ;
( TAKE THE XX AND YY 16 BIT VALUES AND SPLIT INTO XH,XL,YH,YL )
: SPLITT 100 /MOD ROT 100 /MOD ;
: RECTANGLE 84 P-T 2DUP SPLITT  P-T P-T P-T P-T
      91 P-T DUP 4 PICK SWAP SPLITT P-T P-T P-T P-T
      91 P-T 2SWAP 2DUP SPLITT P-T P-T P-T P-T
      91 P-T DUP 4 PICK SWAP SPLITT P-T P-T P-T P-T
      91 P-T 2SWAP SPLITT P-T P-T P-T P-T DROP DROP ;
1D 00 1FF 096 RECTANGLE   1D C8 1FF 15E RECTANGLE      -->

SCREEN #70
( ALPHA PHRASE WRITE TO SCREEN )
HEX  VARIABLE WDL
( SET GRAPHICS CHARACTER MODE )
: CHAR-MODE 99 C0 PC! PORTRDY 00 C0 PC! PORTRDY ;
( DEFINE THE PHRASE TO BE WRITTEN AS 'WORD-BUF' )
: WORDD ." UPPER WAVEFORM - POINTS 1 TO 500$" ; ' WORDD WDL !
( WHEN ENTERRING HERE, THE ASCII HEX CHAR. MUST BE ON STACK )
: SEND-PHRASE 98 C0 PC! PORTRDY C0 PC! PORTRDY ;
( MOVE GRAPHICS CURSOR TO X & Y LOCATION; TOP OF STACK: Y -> X )
: CURSOR 84 C0 PC! PORTRDY SPLITT P-T P-T P-T P-T ;
( X & Y LOCATIONS PREVIOUSLY SPECIFIED )
: PHRASE-WRITE WDL @ 5 + BEGIN DUP C@ DUP 24 <>
WHILE SEND-PHRASE 1+ REPEAT DROP DROP ;
1D 160 CURSOR PHRASE-WRITE
: WORDD ." LOWER WAVEFORM - POINTS 501 TO 1000$" ; ' WORDD WDL !
1D 098 CURSOR PHRASE-WRITE   DECIMAL -->

FIG. 18N

SCREEN #71
( CONTINUE PLOTTING RECTANGLES AND UPPER LABELS )
( WRITE TO SCREEN UPPER DATA BOXES )
HEX
1D 180 1FF 1DF RECTANGLE
1D 180 FF 1DF RECTANGLE
( WRITE TO SCREEN UPPER BOX LABELS )
99 P-T 04 P-T
: WORDD ." CARDIAC OUTPUT$" ; ' WORDD WDL !
36 1C0 CURSOR PHRASE-WRITE
( UNDERLINE CO WORD )
: WORDD ." ------------$" ; ' WORDD WDL !
36 1AD CURSOR PHRASE-WRITE
( WRITE L/M UNDER CO AND RESET ALPHA MODE TO SINGLE HIGH CHAR )
: WORDD ." L/MIN$" ; ' WORDD WDL ! 90 190 CURSOR PHRASE-WRITE
99 P-T 00 P-T DECIMAL -->

SCREEN #72
( CONTINUE DEVELOPMENT OF ALPHA SCREEN )
HEX
( SEND-OUT TIME BASELINE )
: WORDD ." |--------------|--------------|--------------|--------------|--------------|$" ;
' WORDD WDL ! 1D AA CURSOR PHRASE-WRITE
( LABEL TIME AXIS WITH DIGITAL VALUES )
: WORDD ." 0.0      0.5       1.0       1.5       2.0       2.5$" ;
' WORDD WDL ! 1D B5 CURSOR PHRASE-WRITE
( WRITE THE LOGO 'SECONDS ----> ' TO THE SCREEN )
: WORDD ." TIME, IN SECONDS ---->$" ; ' WORDD WDL !
150 9C CURSOR PHRASE-WRITE

DECIMAL
-->

SCREEN #73
( CONTINUE ALPHA SET-UP SCREEN - WRITE UPPER LABELS )
HEX
( WRITE UPPER-RIGHT LABELS )
: WORDD ." BUFFER MAXIMUM VALUE ........$" ; ' WORDD WDL !
10A 1C8 CURSOR PHRASE-WRITE
: WORDD ." BUFFER MINIMUM VALUE ........$" ; ' WORDD WDL !
10A 1B4 CURSOR PHRASE-WRITE
: WORDD ." HEART RATE .................$" ; ' WORDD WDL !
10A 1A0 CURSOR PHRASE-WRITE
: WORDD ." FORMULA CORRECTION FACTOR ...$" ; ' WORDD WDL !
10A 18B CURSOR PHRASE-WRITE

DECIMAL -->

FIG. 18·O

SCREEN #74
( SETUP VERTICAL LABELS NEXT TO WAVEFORM GRIDS )
HEX
( WRITE DIGITAL VALUES AND TICKS MARKS )
: WORDD ." 750-$" ; ' WORDD WDL ! 04 158 CURSOR PHRASE-WRITE
04 90 CURSOR PHRASE-WRITE
 : WORDD ." -$" ; ' WORDD WDL ! 16 128 CURSOR PHRASE-WRITE
16 60 CURSOR PHRASE-WRITE
16 F8 CURSOR PHRASE-WRITE 16 30 CURSOR PHRASE-WRITE
: WORDD ." 0.0_$" ; ' WORDD WDL ! 04 C8 CURSOR PHRASE-WRITE
04 00 CURSOR PHRASE-WRITE
( SEND VERTICAL LABELS )
99 P-T 02 P-T
: WORDD ." SIGNAL, IN MILLIVOLTS$" ; ' WORDD WDL !
12 10 CURSOR PHRASE-WRITE 12 D8 CURSOR PHRASE-WRITE
99 P-T 00 P-T
DECIMAL           -->

SCREEN #75
( LAST SCREEN OF VIDEO LOADER SCREENS - FORGET STATEMENT )
FORGET MICRO-RESET    CREATE TIME_BUF 10 ALLOT
                    TIME_BUF 10 32 FILL
( TIME SCREENS )
: STIME CLS 10 05 GOTOXY ." ENTER TIME: ( USE FORM HH:MM:SS )"
        TIME_BUF 10 EXPECT
        0. TIME_BUF 1- CONVERT DROP DROP HRS !
        0. TIME_BUF 2 + CONVERT DROP DROP MINS !
        0. TIME_BUF 5 + CONVERT DROP DROP SECS ! ;
: .TIME HRS @ DUP 10 < IF ." 0" THEN . 08 EMIT ." :"
        MINS @ DUP 10 < IF ." 0" THEN . 08 EMIT ." :"
        SECS @ DUP 10 < IF ." 0" THEN . ;
: @TIME HRS @ 256 * MINS @ + SECS @ 256 * ;

SCREEN #76
( SELECT CONTROL FOR CCOC - SCREEN #1 - 12/17/86 )
VARIABLE COL_LOCATION
( FOR EACH VARIABLE BELOW, A '1' INDICATES 'ON' A '0' OFF )
VARIABLE CH#1     VARIABLE CH#2     VARIABLE CH#3
VARIABLE CH#4     VARIABLE CH#5
 : TT 20 EMIT ; : LIST_A 20 EMIT
08 13 GOTOXY ." MONITOR" 08 14 GOTOXY ." CONTROL==>" 20 EMIT
20 12 GOTOXY ." ............ELECTRODE PAIRS SELECTED............"
20 16 GOTOXY ." ................................................"
20 14 GOTOXY CH#1 @ IF TT ." PAIR#1 " TT ELSE ." PAIR#1 " THEN
30 14 GOTOXY CH#2 @ IF TT ." PAIR#2 " TT ELSE ." PAIR#2 " THEN
40 14 GOTOXY CH#3 @ IF TT ." PAIR#3 " TT ELSE ." PAIR#3 " THEN
50 14 GOTOXY CH#4 @ IF TT ." PAIR#4 " TT ELSE ." PAIR#4 " THEN
60 14 GOTOXY CH#5 @ IF TT ." PAIR#5 " TT ELSE ." PAIR#5 " THEN
20 15 GOTOXY 20 COL_LOCATION ! ;          -->

FIG. 18P

SCREEN #77
( SELECT CONTROL FOR CCOC - SCREEN #2 - 12/17/86 )

: SEND_CONTROL CH#1 @ CH#2 @ 2 * + CH#3 @ 4 * + 40 +
 0 8 PC! 8 PC!   CH#4 @ CH#5 @ 2 * + 72 + 0 8 PC! 8 PC! ;
: INIT_8255 137 11 PC! ;
: CURSOR_OFF 27 EMIT 91 EMIT 49 EMIT 59 EMIT 57 EMIT 109 EMIT ;
: CURSOR_ON 27 EMIT 91 EMIT 49 EMIT 59 EMIT 56 EMIT 109 EMIT ;

: BOX-FULL 1 0 GOTOXY 78 1 DO 95 EMIT LOOP 22 0 DO 0 I 1 +
  GOTOXY  124 EMIT 78 I 1 + GOTOXY  124 EMIT LOOP 1 23 GOTOXY
  78 1 DO 95 EMIT LOOP 00 00 GOTOXY ;
: DRAW-SCREEN
20 EMIT 27 01 GOTOXY ." ELECTRODE SELECT SCREEN " 20 EMIT ;
-->

SCREEN #78
( SELECT CONTROL FOR CCOC - SCREEN #3 - 12/17/86 )

: ERASE_LINE COL_LOCATION @ 15 GOTOXY ."         "; 
: MOVE-CURSOR LIST_A ." ------" SEND_CONTROL BEGIN
  0 KEY DUP 21 <> IF DUP 13 <> IF DUP 23 <> IF DUP 26 <> IF 81
  = IF DROP DROP 1 1 THEN
        ELSE DROP ERASE_LINE 10 COL_LOCATION +! THEN
        ELSE DROP ERASE_LINE -10 COL_LOCATION +! THEN
        ELSE DROP COL_LOCATION @ DUP 14 GOTOXY 5 - 10 / CASE
     1 OF CH#1 @ IF ." PAIR#1 " 0 ELSE TT ." PAIR#1 " TT 1
           THEN CH#1 ! ENDOF
     2 OF CH#2 @ IF ." PAIR#2 " 0 ELSE TT ." PAIR#2 " TT 1
           THEN CH#2 ! ENDOF
     3 OF CH#3 @ IF ." PAIR#3 " 0 ELSE TT ." PAIR#3 " TT 1
           THEN CH#3 ! ENDOF         -->

SCREEN #79
( SELECT CONTROL FOR CCOC - SCREEN #4 - 12/17/86 )
     4 OF CH#4 @ IF ." PAIR#4 " 0 ELSE TT ." PAIR#4 " TT 1
           THEN CH#4 ! ENDOF
     5 OF CH#5 @ IF ." PAIR#5 " 0 ELSE TT ." PAIR#5 " TT 1
           THEN CH#5 ! ENDOF
     ENDCASE
     THEN
           COL_LOCATION @ DUP 20 < IF DROP 20 THEN DUP 60 >
IF DROP 60 THEN DUP 15
           GOTOXY ." ----- " COL_LOCATION !
           SEND_CONTROL
     ELSE ERASE_LINE 38 09 GOTOXY ." --- " DROP 1 THEN
           UNTIL  ( DROP 1 CR CR CR ) ;
( THE WORD 'MOVE-CURSOR' RUNS THIS SELECT SOFTWARE )
( SCREENS 66, 67, 68 AND 69 CONTROL THIS WORD ) -->

FIG. 18 Q

SCREEN #80
( LABEL SCREEN FOR SELECT SCREEN - SCREEN 5 )

: LABEL-SCREEN
08 18 GOTOXY ." Use UP, DOWN , LEFT and RIGHT arrow keys to move the select cursor."
08 20 GOTOXY ." The 'ENTER' key toggles the electrode pairs on and off."
08 21 GOTOXY ." To exit this routine, hit the DOWN arrow key then the 'Q' key to quit." ;

-->

SCREEN #81
( SELECT CONTROL FOR CCOC - SCREEN #6 - 12/18/86 )

( FOR EACH VARIABLE BELOW, A VALUE > 0 INDICATES THE )
( ELECTRODE NUMBER WHICH HAS BEEN SELETED )
( IF THE VALUE IS ZERO, NO ELECTRODE HAS BEEN SELECTED )
( CHIP #1 IS THE DRIVE OUTPUT FOR THE OSCILLATOR )
( CHIP #4 IS THE RETURN PATH FOR THE OSCILLATOR )
VARIABLE CHIP1   VARIABLE CHIP4
: E_BK 08 EMIT ." "; ( SAME AS ERASE_BACK )
( THE FOLLOWING WORD WRITES THE INITIAL HEADER INFO )
: LIST_B 20 EMIT 08 07 GOTOXY ." DRIVE"
08 08 GOTOXY ." SIGNAL==>" 08 09 GOTOXY ." CONTROL" 20 EMIT
20 06 GOTOXY ." .........DRIVE/RETURN ELECTRODES SELECTED......"
20 10 GOTOXY ." .............................................."       -->

SCREEN #82
( SELECT CONTROL FOR CCOC - SCREEN #7 - 12/18/86 )

22 08 GOTOXY ." DRIVE ELECTRODE"
47 08 GOTOXY ." RETURN ELECTRODE"
39 08 GOTOXY CHIP1 @ DUP IF TT . TT E_BK ELSE ." *" DROP THEN
65 08 GOTOXY CHIP4 @ DUP IF TT . TT E_BK ELSE ." *" DROP THEN
38 09 GOTOXY ." ---" 38 COL_LOCATION ! ;

: PAUSE1 3000 0 DO I 5 + DROP LOOP ;

: XMIT_DRIVE CHIP1 @ 0 <> IF
        0 8 PC! PAUSE1  CHIP1 @ 8 + 16 + 1 - 8 PC!
    THEN  CHIP4 @ 0 <> IF PAUSE1
        0 8 PC! PAUSE1  CHIP4 @ 8 + 128 + 1 - 8 PC!  THEN ;

: ERASE_DASH COL_LOCATION @ 09 GOTOXY ."   "; -->

FIG. 18R

SCREEN #83
( SELECT C0NTROL FOR CCOC - SCREEN #8 - 12/18/86 )

: MOVE_CURSOR LIST_B BEGIN 0 KEY DUP DUP 47 > SWAP 57 < AND IF
COL_LOCATION @ DUP 1 + 08 GOTOXY 64 -
IF DUP 48 - CHIP1 ! ELSE DUP 48 - CHIP4 !
THEN 48 - DUP 0 > IF TT . TT E_BK ELSE ." *" DROP
THEN ELSE DUP 26 = IF COL_LOCATION @ DUP 09 GOTOXY
ERASE_DASH 64 < IF 26 COL_LOCATION +! THEN THEN
DUP 23 = IF COL_LOCATION @ DUP 09 GOTOXY ERASE_DASH 40 > IF
-26 COL_LOCATION +! THEN THEN COL_LOCATION @ 09 GOTOXY ." ---"
18 = IF ERASE_DASH DROP 1 THEN THEN XMIT_DRIVE UNTIL ;

: ELECTRODE2 INIT_8255 CURSOR_OFF DRAW-SCREEN LABEL-SCREEN
        LIST_A BEGIN 0 MOVE_CURSOR
        MOVE-CURSOR UNTIL CURSOR_ON ;

-->

SCREEN #84
( SUMMARY SCREEN FOR CCOC INSTRUMENT - 12/19/86 )

: PERIMETER CLS BOX-FULL 06 04 GOTOXY
." ------------------------ CCOC CONTROL MODE ------------------------"
5 BEGIN DUP DUP 06 SWAP GOTOXY ." I"
74 SWAP GOTOXY ." I" 1 + DUP 17 = UNTIL DROP 06 17 GOTOXY
." ------------------------------------------------------------" ;

: STARRT 10 08 GOTOXY
20 EMIT ." TO START THE PROGRAM TYPE: --> " 20 EMIT ." "
20 EMIT ." MENU1" 20 EMIT 30 10 GOTOXY ;

SCREEN #85
( SUMMARY SCREEN FOR CCOC INSTRUMENT - 12/19/86 )

( LOAD SOFTWARE )
31 LOAD
INT-ON
76 LOAD
86 LOAD
STIME STARRT ( KEY CONTROLS FOR THE SCREEN ARE: )
        ( 'ENTER' --> TOGGLES ELECTRODE PAIR ON/OFF )
        ( 'ARROW KEYS ARE ACTIVE FOR LEFT, RIGHT UP AND DOWN )
        ( 'Q' WHILE ON LOWER SECTION QUITS THE PROCESS )
        ( NUMBERS CHANGE ELECTRODES )

FIG. 18 S

SCREEN #86
( INITIALIZE SCREEN FOR PATIENT ENTRY MODULE )

| | |
|---|---|
| CREATE PNAME 25 ALLOT | CREATE PID 12 ALLOT |
| CREATE PSEX 05 ALLOT | CREATE PAGE 05 ALLOT |
| CREATE PWGT 06 ALLOT | CREATE PHT 06 ALLOT |
| CREATE T-SURG 12 ALLOT | CREATE SURG 12 ALLOT |
| CREATE ANES 12 ALLOT | CREATE S-TIME 10 ALLOT |
| CREATE CASE-NUM 03 ALLOT | CREATE ID-FNAME 10 ALLOT |
| CREATE DATA-FNAME 10 ALLOT | CREATE DATE-MEM 10 ALLOT |

```
: ZERO-PAT  PNAME 25 32 FILL    PID 12 32 FILL
            PSEX 05 32 FILL      PAGE 05 32 FILL
            PWGT 06 32 FILL      PHT 06 32 FILL
            T-SURG 12 32 FILL  SURG 12 32 FILL
            ANES 12 32 FILL      S-TIME 10 32 FILL
            CASE-NUM 03 32 FILL  ID-FNAME 10 32 FILL
            DATA-FNAME 10 32 FILL  DATE-MEM 10 32 FILL ;   -->
```

SCREEN #87
( INITIALIZE SCREEN #2 FOR PATIENT ENTRY MODULE )

```
: SLASH DUP  47 ROT C! 1+ ;

: DATE-WRITE @DATE 256 /MOD DUP 10 < IF DATE-MEM
DUP 48  SWAP C! 1+ DUP ROT 48 + SWAP C! 1+
ELSE DATE-MEM  SWAP 10 /MOD 48 + ROT DUP ROT
SWAP C! 1+ DUP ROT 48 + SWAP C! 1+ THEN
        SLASH SWAP DUP 10 < IF SWAP DUP 48 SWAP C! 1+ DUP
        ROT 48 + SWAP C! 1+ ELSE 10 /MOD 48  + ROT DUP
        ROT SWAP C! 1+ DUP ROT 48 + SWAP C! 1+
THEN SLASH SWAP 1900 - 10 /MOD 48 + ROT DUP ROT
SWAP C! 1+ DUP ROT 48 + SWAP C! DROP ; -->
```

SCREEN #88
( FIRST SCREEN OF PATIENT DATA INPUT MODULE )        ( 1/16/87 - JP )

```
: PAT-ENTRY BEGIN ZERO-PAT
CLS BOX-FULL
20 EMIT 25 2 GOTOXY ." ***** CCOC DATA ENTRY SCREEN *****"
20 EMIT 10 4 GOTOXY ." ENTER THE FOLLOWING INFORMATION:"
10 5 GOTOXY 33 1 DO 61 EMIT LOOP 05 6 GOTOXY  ." Patient Name:........."
05 7    GOTOXY ." Patient I.D. Number:.." 05 8 GOTOXY ." Patient Sex:(M or F).."
05 9 GOTOXY ." Patient Age:........." 05 10 GOTOXY ." Patient Weight:(kg)..."
05 11 GOTOXY         ."  Patient Height:(cm)..." 60 6 GOTOXY ." Time: "  -->
```

FIG. 18T

SCREEN #89
( SECOND SCREEN OF PATIENT DATA INPUT MODULE )

2 12 GOTOXY 78 1 DO 95 EMIT LOOP
05 13 GOTOXY ." Type of Surgery:......."
05 14 GOTOXY ." Surgeon:.............."
05 15 GOTOXY ." Anesthesiologist:......"
05 16 GOTOXY ." Start Time of Study:.."
05 17 GOTOXY ." Study Case #:........."
43 13 GOTOXY ." ID-Filename:(4 Char)...."
43 14 GOTOXY ." (File Form: B:XXXX.IDD )"
43 15 GOTOXY ." Data-Filename:(4 Char).."
43 16 GOTOXY ." (File Form: B:XXXX.DAT )"
02 18 GOTOXY 78 1 DO 95 EMIT LOOP
-->

SCREEN #90
( THIRD SCREEN OF PATIENT DATA INPUT MODULE )

15 19 GOTOXY ." HIT THE 'ENTER' or 'RETURN' KEY AFTER EACH ENTRY"
15 20 GOTOXY ." (To correct any entries, type 'R' and re-enter)"

CURSOR_OFF
20 21 GOTOXY ." ( E ==> EXIT   R ==> RE-ENTER )"
29 06 GOTOXY  20 EMIT 24 0 DO 32 EMIT LOOP 20 EMIT
29 06 GOTOXY  PNAME 25 EXPECT
29 06 GOTOXY  PNAME 25 TYPE
29 07 GOTOXY 20 EMIT 11 0 DO 32 EMIT LOOP 20 EMIT
29 07 GOTOXY  PID 12 EXPECT
29 07 GOTOXY  PID 12 TYPE   -->

SCREEN #91
( FOURTH SCREEN OF PATIENT DATA INPUT MODULE )

29 08 GOTOXY 20 EMIT 04 0 DO 32 EMIT LOOP 20 EMIT
29 08 GOTOXY  PSEX 05 EXPECT
29 08 GOTOXY  PSEX 05 TYPE
29 09 GOTOXY 20 EMIT 04 0 DO 32 EMIT LOOP 20 EMIT
29 09 GOTOXY  PAGE 05 EXPECT
29 09 GOTOXY  PAGE 05 TYPE
29 10 GOTOXY 20 EMIT 05 0 DO 32 EMIT LOOP 20 EMIT
29 10 GOTOXY  PWGT 06 EXPECT
29 10 GOTOXY  PWGT 06 TYPE
29 11 GOTOXY 20 EMIT 05 0 DO 32 EMIT LOOP 20 EMIT
29 11 GOTOXY  PHT 06 EXPECT
29 11 GOTOXY  PHT 06 TYPE
-->

FIG. 18U

SCREEN #92
( FIFTH SCREEN OF PATIENT DATA INPUT MODULE )
  29 13 GOTOXY 20 EMIT 11 0 DO 32 EMIT LOOP 20 EMIT
  29 13 GOTOXY  T-SURG 12 EXPECT
  29 13 GOTOXY  T-SURG 12 TYPE
  29 14 GOTOXY 20 EMIT 11 0 DO 32 EMIT LOOP 20 EMIT
  29 14 GOTOXY  SURG 12 EXPECT
  29 14 GOTOXY  SURG 12 TYPE
  29 15 GOTOXY 20 EMIT 11 0 DO 32 EMIT LOOP 20 EMIT
  29 15 GOTOXY  ANES 12 EXPECT
  29 15 GOTOXY  ANES 12 TYPE
  29 16 GOTOXY 20 EMIT 09 0 DO 32 EMIT LOOP 20 EMIT
  29 16 GOTOXY  S-TIME 10 EXPECT
  29 16 GOTOXY  S-TIME 10 TYPE            -->

SCREEN #93
( SIXTH SCREEN OF PATIENT DATA INPUT MODULE )
  29 17 GOTOXY 20 EMIT 02 0 DO 32 EMIT LOOP 20 EMIT
  29 17 GOTOXY  CASE-NUM 03 EXPECT
  29 17 GOTOXY  CASE-NUM 03 TYPE
  67 13 GOTOXY 20 EMIT 09 0 DO 32 EMIT LOOP 20 EMIT
  67 13 GOTOXY  ID-FNAME 10 EXPECT
  67 13 GOTOXY  ID-FNAME 10 TYPE
  67 15 GOTOXY 20 EMIT 09 0 DO 32 EMIT LOOP 20 EMIT
  67 15 GOTOXY  DATA-FNAME 10 EXPECT
  67 15 GOTOXY  DATA-FNAME 10 TYPE
  20 EMIT
  20 21 GOTOXY ." ( E ==> EXIT   R ==> RE-ENTER )"
  20 EMIT                         -->

SCREEN #94
( SEVENTH SCREEN OF PATIENT DATA INPUT MODULE )
00 BEGIN DROP KEY DUP DUP 69 = SWAP 82 = OR UNTIL
82 <> UNTIL CURSOR_ON ;
PAT-ENTRY EXITS HERE.  NOW CHECK IF DATA IS TO GO TO DISK )
FCB FILE1
: DISK-ID
CLS 20 05 GOTOXY ." STORE THIS PATIENT DATA ON DISK ?"
25 06 GOTOXY ." ( Y = YES  N = NO ) "
BEGIN KEY DUP DUP 89 = SWAP 78 = OR UNTIL 89 = IF
FILE1 FILENAME B:TEMP.IDD   FILE1 ID-FNAME PARSE-FILENM
FILE1 OPEN-FILE 0 = IF 07 08 GOTOXY ." *** ID FILE WITH SAME NAME ALREADY
EXISTS --> MAKE-FILE ABORTED ***" 25 10 GOTOXY    ." RE-WRITE EXISTING
FILE ? " 27 11 GOTOXY ." ( Y = YES  N = NO )"  BEGIN KEY DUP DUP 89 = SWAP 78
= OR UNTIL 89 = DUP 0= IF   FILE1 CLOSE-FILE DROP THEN ELSE FILE1 MAKE-
FILE DROP 01  -->

FIG. 18V

SCREEN #95
( MEMORY MOVE SCREEN FOR DISK WRITE OF ID FILE )
20 09 GOTOXY
." -- NEW PATIENT ID FILE CREATED --" THEN IF DATE-WRITE
FILE1 ?BUFFER-ADDR DUP PNAME SWAP 25 CMOVE 25 +
DUP PID SWAP 12 CMOVE 12 +
DUP PSEX SWAP 05 CMOVE 05 + DUP PAGE SWAP 05 CMOVE 05 +
DUP PWGT SWAP 06 CMOVE 06 + DUP PHT SWAP 06 CMOVE 06 +
DUP T-SURG SWAP 12 CMOVE 12 + DUP SURG SWAP 12 CMOVE 12 +
DUP ANES SWAP 12 CMOVE 12 + DUP S-TIME SWAP 10 CMOVE 10 +
DUP CASE-NUM SWAP 03 CMOVE 03 + DUP DATE-MEM SWAP 10 CMOVE 10 +
DUP DATA-FNAME SWAP 10 CMOVE 10 + -->

SCREEN #96
( ID DISK WRITE ROUTINE CONTINUED )
FILE1 00 WRITE-RANDOM DROP FILE1 CLOSE-FILE DROP
THEN THEN ;
FCB FILE2
: FILE-HEAD FILE2 FILENAME B:TEEP.DAT
           FILE2 DATA-FNAME PARSE-FILENM
FILE2 OPEN-FILE 0 = IF
05 13 GOTOXY ." ------------------------------------------------------------"
07 17 GOTOXY ." ***
DATA FILE WITH SAME NAME ALREADY EXISTS-->MAKE-FILE ABORTED ***"
ELSE FILE2 MAKE-FILE DROP 20 18 GOTOXY ." -- NEW DATA FILE CREATED --"
THEN FILE2 CLOSE-FILE DROP
20 23 GOTOXY ." ( HIT ANY KEY TO CONTINUE: )" KEY DROP ;
: ENTRY-MODULE PAT-ENTRY DISK-ID FILE-HEAD CLS ;
( ENTRY-MODULE ENDS HERE. BEGAN ON SCREEN 80 )
-->

SCREEN #97
( FIRST SCREEN OF DATA ENTRY MODULE )

VARIABLE EPISODE# 00 EPISODE# ! VARIABLE RECORD# 00 RECORD# !
CREATE LAST-TIME 10 ALLOT    VARIABLE P-CAL 00 P-CAL !
LAST-TIME 10 32 FILL     VARIABLE EPI-TIME
: INPUT-SCREEN CLS BOX-FULL
 20 EMIT 18 02 GOTOXY
." CONTINUOUS CARDIAC OUTPUT - DATA ENTRY SCREEN" 20 EMIT
05 04 GOTOXY ." PATIENT NAME:....." PNAME 25 TYPE
05 05 GOTOXY ." DATE:............." .DATE
02 06 GOTOXY 77 01 DO 95 EMIT LOOP
05 07 GOTOXY ." PREVIOUS ENTRY #: " EPISODE# @ .
30 07 GOTOXY ." TIME: "    LAST-TIME 10 TYPE
50 07 GOTOXY ." PREVIOUS CAL-FACTOR: " P-CAL @ .
02 08 GOTOXY 77 1 DO 61 EMIT LOOP    -->

FIG. 18W

SCREEN #98
( SECOND SCREEN OF DATA ENTRY MODULE )

05 09 GOTOXY ." EPISODE #:"
35 09 GOTOXY ." PRESENT CAL-FACTOR:"
15 11 GOTOXY ." RUN #"    24 11 GOTOXY ." THERMO-C.O."
37 11 GOTOXY ." IMPED-C.O."  50 11 GOTOXY ." TIME"
60 11 GOTOXY ." HRATE"
15 12 GOTOXY 50 00 DO 45 EMIT LOOP
17 13 GOTOXY ." 1"  17 14 GOTOXY ." 2"  17 15 GOTOXY ." 3"
17 16 GOTOXY ." 4"  17 17 GOTOXY ." 5"  17 18 GOTOXY ." 6"
02 19 GOTOXY 77 1 DO 61 EMIT LOOP   -->

SCREEN #99
( THIRD SCREEN OF INPUT MODULE )

02 20 GOTOXY ." ENTER EACH THERMODILUTION CARDIAC OUTPUT
IMMEDIATELY AFTER EACH BOLUS IS SHOT"
02 21 GOTOXY ." HIT THE 'ENTER' OR 'RETURN' KEY TWICE AFTER
COMPLETING THE LAST DATA ENTRY." ;

: UPDATE-EPISODE
    EPISODE# @ 1+ DUP EPISODE# !   16 09 GOTOXY .
    BUF-NUM @ 55 09 GOTOXY .
    BUF-NUM @ P-CAL ! ;
-->

SCREEN #100
( FOURTH SCREEN OF DATA ENTRY MODULE )

CREATE THERMO-CO 10 ALLOT   CREATE TEMP-BUF 05 ALLOT
( CONVERTS A VARIABLE WHICH IS A DECIMAL # TIMES 100 TO A )
( STRING WITH A DECIMAL POINT )
( ENTER WITH # ON STACK AND LEAVE WITH STRING IN TEMP-BUF )
: VAR-CONVERT  TEMP-BUF 05 32 FILL
  1000 /MOD 1 = IF 49 TEMP-BUF C! THEN 100 /MOD
  48 + TEMP-BUF 1+ C! 46 TEMP-BUF 2 + C!
  10 /MOD 48 + TEMP-BUF 3 + C! 48 + TEMP-BUF 4 + C! ;

SCREEN #101
( FIFTH SCREEN OF DATA ENTRY MODULE )

CREATE TEMP-BUF1 06 ALLOT  CREATE TEMP-BUF2 10 ALLOT
           TEMP-BUF2 10 32 FILL
( ENTER THIS ROUTINE WITH NUMBER TO BE CONVERTED ON STACK )
( VALUE MUST BE < 9999, CONVERTED STRING WILL BE IN TEMP-BUF1 )
: ASCII-CONVERT
   TEMP-BUF1 06 32 FILL 1000 /MOD 48 + TEMP-BUF1 C!
                   100 /MOD 48 + TEMP-BUF1 1+ C!
                    10 /MOD 48 + TEMP-BUF1 2 + C!
                    48 + TEMP-BUF1 3 + C! ;
: NOW-TIME @TIME SWAP 256 /MOD 10 /MOD 48 + TEMP-BUF2 C! 48 +   TEMP-
  BUF2 1+ C! 58 TEMP-BUF2 2 + C! 10 /MOD 48 + TEMP-BUF2  3 + C! 48 + TEMP-
  BUF2 4 + C! 58 TEMP-BUF2 5 + C! 256 /MOD    10 /MOD 48 + TEMP-BUF2 6 + C! 48 +
  TEMP-BUF2 7 + C! DROP    TEMP-BUF2 LAST-TIME 10 CMOVE ; -->

SCREEN #102
( SIXTH SCREEN OF DATA ENTRY ROUTINE )
           ( THERMO-CO INPUT LOOP STARTS HERE )
: ENTER-CO  CURSOR_OFF FILE2 OPEN-FILE DROP
06 00 DO THERMO-CO 10 32 FILL  26 13 I + GOTOXY
20 EMIT 09 00 DO 32 EMIT LOOP 20 EMIT
26 13 I + GOTOXY THERMO-CO 10 EXPECT
SPAN @ 0= IF LEAVE THEN
26 13 I + GOTOXY THERMO-CO 10 TYPE
38 13 I + GOTOXY CARD-OUT @ VAR-CONVERT TEMP-BUF 05 TYPE
48 13 I + GOTOXY .TIME  62 13 I + GOTOXY HRATE @ .
FILE2 ?BUFFER-ADDR DUP RECORD# @ ASCII-CONVERT
TEMP-BUF1 SWAP 06 CMOVE 06 + DUP
EPISODE# @ ASCII-CONVERT TEMP-BUF1
SWAP 06 CMOVE 06 + DUP 01 I + ASCII-CONVERT TEMP-BUF1  SWAP 06
CMOVE 06 + DUP NOW-TIME TEMP-BUF2 SWAP 10 CMOVE  10 + DUP  -->

SCREEN #103
( SEVENTH SCREEN OF DATA ENTRY ROUTINE )

THERMO-CO SWAP 10 CMOVE 10 + DUP TEMP-BUF SWAP 05 CMOVE
05 + DUP HRATE @ ASCII-CONVERT TEMP-BUF1 SWAP 06 CMOVE
06 + BUF-NUM @ ASCII-CONVERT TEMP-BUF1 SWAP 06 CMOVE
FILE2 RECORD# @ WRITE-RANDOM DROP
RECORD# @ 1+ RECORD# ! LOOP
FILE2 CLOSE-FILE DROP
CURSOR_ON ;
: EPTIME EPISODE# @ 8 = IF @TIME DROP 256 /MOD 60 * +
EPI-TIME ! THEN ;
: DATA-MODULE
INPUT-SCREEN UPDATE-EPISODE ENTER-CO EPTIME ; -->

FIG. 18Y

SCREEN #104
( FIRST SCREEN OF CAL-FACTOR DETERMINATION MODULE )
: START-CAL  CLS  BOX-FULL 20 EMIT
    25 02 GOTOXY ."  CAL-FACTOR ADJUST ROUTINE " 20 EMIT
    05 05 GOTOXY ." PRESENT CAL-FACTOR ===> " BUF-NUM @ .
    10 07 GOTOXY ." SELECT METHOD OF CHANGING CAL-FACTOR:"
    10 08 GOTOXY ." ====================================="
    10 09 GOTOXY ." 1. MANUAL ENTRY OF NEW CAL-FACTOR."
    10 10 GOTOXY ." 2. AUTOMATIC CALCULATION."
    10 11 GOTOXY ." 3. EXIT WITH NO CHANGES."
    10 12 GOTOXY ." ====================================="
    10 13 GOTOXY ." ENTER SELECTION #: "
    00 BEGIN DROP KEY DUP DUP DUP 49 = SWAP 50 = OR SWAP
    51 = OR UNTIL 49 - CASE  0 OF 49 EMIT 10 15 GOTOXY
." ENTER NEW CAL-FACTOR VALUE:.."  #IN BUF-NUM ! ENDOF -->

SCREEN #105
( SECOND SCREEN OF CAL-FACTOR DETERMINATION MODULE )
1 OF 50 EMIT BEGIN 48 15 GOTOXY ."          "
10 15 GOTOXY ." ENTER THERMODILUTION CARDIAC OUTPUT VALUE: "
PAD 10 EXPECT PAD 1- NUMBER? 10 17 GOTOXY 20 EMIT
." ERROR - RE-ENTER C.O. VALUE " 20 EMIT UNTIL  10 17 GOTOXY ."  "
DROP  DUP 0 = IF DROP 01 THEN   DPL @ DUP -1 = IF DROP
   100 * BUF-NUM @ CARD-OUT @ */ ELSE DUP 1 = IF DROP
   10 * BUF-NUM @ CARD-OUT @ */ ELSE DUP 2 = IF DROP
   BUF-NUM @ CARD-OUT @ */ ELSE 3 = IF
   BUF-NUM @ CARD-OUT @ 10 * */ THEN THEN THEN THEN
DUP BUF-NUM ! 10 17 GOTOXY ." THE NEW CAL-FACTOR IS ==> " .
25 20 GOTOXY ." ( HIT ANY KEY TO EXIT ROUTINE: )" KEY DROP  ENDOF
2 OF 51 EMIT CLS ENDOF ENDCASE ; -->

SCREEN #106
( FIRST SCREEN OF TRANSPORT VARIABLE SAVE ROUTINE )
FCB FILE3    : LEAVE-DSK  BEGIN CLS BOX-FULL  20 EMIT
17 02 GOTOXY ." TEMPORARY VARIABLE STORE ROUTINE FOR TRANSPORT"
20 EMIT  25 04 GOTOXY ." DATA-FILENAME: " DATA-FNAME 10 TYPE
10 06 GOTOXY ." ENTER TRANSFER FILENAME: ( USE THE FORM ==> B:XXX#.MOV )"
10 07 GOTOXY ."  where:  XXX = FIRST 3 LETTERS OF PATIENT'S LAST NAME"
20 08 GOTOXY ." # = 1 FOR IND. RM. to O.R. TRANSFER"
20 09 GOTOXY ." # = 2 FOR O.R. to UNIT TRANSFER"
20 10 GOTOXY ." # = 3 FOR UNIT to O.R. TRANSFER"
20 11 GOTOXY ." # = 4 FOR O.R. back to UNIT TRANSFER"
15 14 GOTOXY ." ( FORM ==> B:XXX#.MOV )"
15 13 GOTOXY FILE3 INPUT-FILENAME
FILE3 OPEN-FILE 0 = IF  07 16 GOTOXY
." * TRANSFER FILE ALREADY EXISTS --> MAKE-FILE ABORTED *"
22 18 GOTOXY ." RE-ENTER TRANSFER FILENAME ?"
24 19 GOTOXY ." ( Y = YES  N = NO )" BEGIN
KEY DUP DUP 89 = SWAP 78 = OR UNTIL 78 = -->

FIG. 18Z

SCREEN #107
( SECOND SCREEN OF TRANSPORT VARIABLE SAVE MODULE )
ELSE   FILE3 MAKE-FILE DROP
FILE3 ?BUFFER-ADDR DUP
PNAME SWAP 25 CMOVE 25 + DUP  LAST-TIME SWAP 10 CMOVE 10 + DUP
DATA-FNAME SWAP 10 CMOVE 10 + DUP  P-CAL @ SWAP ! 2 + DUP
RECORD# @ SWAP ! 2 + DUP  EPISODE# @ SWAP ! 2 + DUP BUF-NUM @
SWAP ! 2 + DUP CHIP1 @ SWAP ! 2 + DUP CHIP4 @ SWAP ! 2 + DUP
CH#1 @ SWAP ! 2 + DUP CH#2 @ SWAP ! 2 + DUP CH#3 @ SWAP ! 2 +
DUP CH#4 @ SWAP ! 2 + CH#5 @ SWAP !
( WRITE VARIABLES TO TEMPORARY FILE/ CLOSE FILE )
20 16 GOTOXY ." ALL REQUIRED DATA HAS BEEN TRANSFERRED"
25 21 GOTOXY ." ( HIT ANY KEY TO CONTINUE )"
KEY DROP 01 THEN UNTIL ;     -->

SCREEN #108
( FIRST SCREEN OF RESTART-UP ROUTINE TO RELOAD VARIABLES )
FCB FILE4
: RELOAD-DSK   CLS   BOX-FULL  20 EMIT
20 02 GOTOXY ." RESTART/RELOAD VARIABLE ROUTINE" 20 EMIT
06 04 GOTOXY ." --- Directory Listing of the B Drive: ---"
14 01 FDOS 2DROP CR DIR 14 00 FDOS 2DROP
10 09 GOTOXY ." ENTER TRANSFER FILENAME:"
10 10 GOTOXY ." ( USE THE FORM ==> B:XXX#.MOV )"
15 12 GOTOXY FILE4 INPUT-FILENAME   FILE4 OPEN-FILE
255 = IF    12 14 GOTOXY ." *** FILE NOT FOUND - NO DATA
HAS BEEN LOADED FROM DISK ***" ELSE
FILE4 00 READ-RANDOM  DROP  FILE4 ?BUFFER-ADDR DUP
PNAME 25 CMOVE 25 + DUP  LAST-TIME 10 CMOVE 10 + DUP
DATA-FNAME  10 CMOVE 10 + DUP  @ P-CAL ! 2 + DUP
-->

SCREEN #109
( SECOND SCREEN OF RESTART-UP ROUTINE TO RELOAD VARIABLES )

@ RECORD# ! 2 + DUP @ EPISODE# ! 2 + DUP @ BUF-NUM !
2 + DUP @ CHIP1 ! 2 + DUP @ CHIP4 ! 2 + DUP @ CH#1 !
2 + DUP @ CH#2 ! 2 + DUP @ CH#3 ! 2 + DUP @ CH#4 !
2 + @ CH#5 !
( CLOSE TEMPORARY MOVE FILE AND PLUG-IN DATA FILENAME )
FILE4 CLOSE-FILE DROP  FILE2 DATA-FNAME PARSE-FILENM ( INITIALIZE PORT/SET DRIVE AND MONITOR ELECTRODES )
INIT_8255 SEND_CONTROL XMIT_DRIVE
20 16 GOTOXY ." ALL REQUIRED DATA HAS BEEN TRANSFERRED"
THEN
25 21 GOTOXY ." ( HIT ANY KEY TO CONTINUE )"
KEY DROP ;  -->

FIG. 18 AA

SCREEN #110
( FIRST SCREEN OF PATIENT STORED DATA REVIEW )

```
VARIABLE BACK-REC
: SCREEN-REVIEW
   CLS BOX-FULL 20 EMIT
   25 01 GOTOXY ."      PATIENT HISTORY         "
   25 02 GOTOXY ." DISPLAY PREVIOUS SAMPLE RUNS " 20 EMIT
   10 04 GOTOXY ." ENTER # OF MOST RECENT RECORD TO REVIEW: "
   20 05 GOTOXY ." ( # RANGE ==>  0 TO " RECORD# @ 1- .." )"
   EGIN 52 04 GOTOXY ."   " 52 04 GOTOXY #IN
   DUP RECORD# @ 1- <= 50 05 GOTOXY
20 EMIT ." ** INPUT ERROR-TRY AGAIN **"
20 EMIT UNTIL BACK-REC ! 50 05 GOTOXY ."                    "
   50 07 GOTOXY   PNAME 25 TYPE
   02 07 GOTOXY ." DISPLAY OF 10 RUNS BACK FROM RECORD SELECTED:"
   02 08 GOTOXY
."================================================
========================" -->
```

SCREEN #111
( SECOND SCREEN OF PATIENT STORED DATA REVIEW )

```
44 09 GOTOXY ." C.O.     C.O.    HEART  CAL-"
05 10 GOTOXY ." RECORD#  EPISODE#  RUN #   TIME   THERMO
IMPED   RATE  FACTOR"
05 11 GOTOXY ." ----------------------------------------------------------" ;

: LOCA BACK-REC @ - - ;
: REVIEW-LOOP
   FILE2 OPEN-FILE DROP
   BACK-REC @ DUP 09 - SWAP DO
   FILE2 I READ-RANDOM DROP 06 12 I LOCA GOTOXY
   FILE2 ?BUFFER-ADDR 01 + DUP 03 TYPE 07 + 16 12 I LOCA
GOTOXY DUP 02 TYPE 06 + 25 12 I LOCA GOTOXY DUP 02 TYPE -->
```

SCREEN #112
(THIRD SCREEN OF PATIENT STORED DATA REVIEW )

```
04 + 32 12 I LOCA GOTOXY DUP 10 TYPE 10 + 45 12 I LOCA
GOTOXY DUP 07 TYPE 10 + 54 12 I LOCA GOTOXY DUP 05 TYPE
06 + 63 12 I LOCA GOTOXY DUP 03 TYPE 06 + 71 12 I LOCA
GOTOXY 03 TYPE -01 +LOOP FILE2 CLOSE-FILE DROP
17 22 GOTOXY
." ( HIT 'R' TO REVIEW MORE HISTORY, 'E' TO EXIT )" ;
: REVIEW-DSK BEGIN SCREEN-REVIEW REVIEW-LOOP
BEGIN KEY DUP DUP 82 = SWAP 69 = OR UNTIL 69 = UNTIL ;
-->
```

FIG. 18BB

SCREEN #113
( FIRST SCREEN OF STUDY SAMPLE TIMES )
: SAMPLE-TIMES
  CLS BOX-FULL
  20 EMIT 25 02 GOTOXY ." CCOC STUDY - SAMPLE TIME LISTING "
  20 EMIT
  10 04 GOTOXY ." [1] PRE-INDUCTION EPISODE"
  10 05 GOTOXY ." [2] POST-INDUCTION EPISODE"
  10 06 GOTOXY ." [3] POST-PERICARDIECTOMY"
  10 07 GOTOXY ." [4] POST-BYPASS (15 MINUTE POST-BYPASS)"
  10 08 GOTOXY ." [5] JUST PRIOR TO CLOSING THE CHEST"
  10 09 GOTOXY ." [6] JUST AFTER CLOSING THE CHEST"
  10 10 GOTOXY ." [7] JUST PRIOR TO PATIENT TRANSPORT"
  10 11 GOTOXY ." [8] PT - POST-TRANSPORT (PATIENT STABILIZED)"
  10 12 GOTOXY ." [9] 30 MINUTES AFTER PT SAMPLE"
  10 13 GOTOXY ." [10] 60 MINUTES AFTER PT SAMPLE" -->

SCREEN #114
( SECOND SCREEN OF STUDY SAMPLE TIMES )

10 14 GOTOXY ." [11] 90 MINUUTES AFTER PT SAMPLE"
  10 15 GOTOXY ." [12] 120 MINUTES AFTER PT SAMPLE"
  10 16 GOTOXY ." [13] 150 MINUTES AFTER PT SAMPLE"
  10 17 GOTOXY ." [14] - [20] EVERY 30 MINUTES (6 HRS POST-OP)"
  05 19 GOTOXY ." NOTE: THE MAXIMUM EPISODE # IS 20
                       USING THE 6 HOUR POST-OPERATIVE "
  12 20 GOTOXY ." MONITORING LIMIT IMPOSED BY THE STUDY."
  25 22 GOTOXY ." ( HIT ANY KEY TO CONTINUE )"
  KEY DROP ;   -->

SCREEN #115
( FIRST SCREEN OF HELP MODULE )
: HELP-MODULE  CLS
  25 02 GOTOXY 20 EMIT ." STUDY 'HELP' SCREEN " 20 EMIT
  10 05 GOTOXY ." SAMPLING RUN INFORMATION:"
  10 06 GOTOXY ." -------------------------"
  10 07 GOTOXY 20 EMIT ." TAKING A SAMPLE: " 20 EMIT
  ." To initiate a sample run, select from the study menu"
  ." selection # 2, 'DATA RUN - SAMPLE ENTRY SCREEN'. "
  ." This selection will automatically call-up a data entry"
  ." screen. The screen is formated such that the thermo"
  ." dilution cardiac output values obtained during"
  ." each sample run can be easily entered."
  ." To begin a sample run, take a thermodilution CO and"
  ." as soon as the output appears on the monitor, enter"
  ." the value into the computer via the keyboard." -->

FIG. 18CC

SCREEN #116
( SECOND SCREEN OF HELP MODULE )

." For example; '4.55' followed by the 'ENTER' key. The"
." value you type-in will appear in the high-lighted box"
." on the screen. When you hit the 'ENTER' key and register"
." your value, the associated Impedance Cardiac Output,"
." Sample-Time and Cal-factor will be automatically entered."
." The computer will automatically move down to the next line"
." and wait for your next entry. Try to enter the CO value "
." as soon as viewing it on the Patient Monitor since the "
." Impedance value will be automatically entered at that time."
." To terminate the sampling episode, simply hit the 'ENTER'"
." key with no numbers entered for a sample run or twice"
." after the last CO value has been entered."
." This will log your data entry and return you to the main" ." selection menu." -->

SCREEN #117
( THIRD SCREEN OF HELP MODULE )

20 23 GOTOXY ." ( ENTER 'C' TO CONTINUE OR 'E' TO EXIT: )"
BEGIN KEY DUP DUP 67 = SWAP 69 = OR UNTIL 67 = IF CLS
25 02 GOTOXY 20 EMIT ." STUDY 'HELP' SCREEN #2 " 20 EMIT
10 04 GOTOXY 20 EMIT ." REVIEWING STORED DATA: " 20 EMIT
." To view previous CO sample episodes, select from"
." the study menu option # 7, ' REVIEW GATHERED PATIENT'"
." CO DATA '. Enter the most recent record number"
." to review. That record and the previous nine records"
." will be displayed. More records can be viewed by"
." by selecting the ' REVIEW MORE HISTORY OPTION '."
." Selecting the ' EXIT ' option will return"
." you to the main menu. " -->

SCREEN #118
( FOURTH SCREEN OF HELP MODULE )

10 11 GOTOXY 20 EMIT ." ENTERING A NEW CAL-FACTOR: " 20 EMIT
." The cal-factor is a multipling constant whose"
." value represents various unknowns such as blood"
." conductivity or tissue signal absorption."
." Calibration to thermodilution CO is determined by"
." modifying the cal-factor value. This is accomplished"
." by selecting option #4, ' ENTER/CALCULATE NEW"
." CAL-FACTOR '. Manually enter a new cal-factor"
." or let the computer formulate a value."
10 19 GOTOXY 20 EMIT ." OBTAINING ASSISTANCE: " 20 EMIT
." To obtain assistance, contact JOHN PETRE at"
." EXT: 5056 or beeper # 1394. Home phone number: 321-"   ." 8742 " -->

FIG. 18DD

SCREEN #119
( FIFTH SCREEN OF HELP MODULE )

20 23 GOTOXY ." ( ENTER 'C' TO CONTINUE OR 'E' TO EXIT: )"
BEGIN KEY DUP DUP 67 = SWAP 69 = OR UNTIL 67 = IF
CLS
25 02 GOTOXY 20 EMIT ."  STUDY 'HELP' SCREEN #3 "  20 EMIT
10 04 GOTOXY 20 EMIT ." THE C.O. IMPEDANCE TECHNIQUE: " 20 EMIT
." Continuous Cardiac Outputs can be obtained by employing"
." a measurement technique which directly monitors"
." the beat-to-beat volume of the Right Ventricle."
." This technique uses the conductive properties of blood"
." to determine the stroke volumes of the right ventricle."
." A modified Swan-Ganz catheter is placed through the"
." right ventricle and positioned such that a series of ring"
." electrodes are within the structure of the RV. A small"
-->

SCREEN #120
( SIXTH SCREEN OF HELP MODULE )

." AC current is passed between two of the far electrodes"
." thus producing time varying potentials between pairs of"
." ring electrodes. These signals are inversely proportional"
." to the blood volume between the electrode pairs. By"
." summing the signals developed accross all pairs of"
." electrodes, a total RV volume signal can be obtained."
20 23 GOTOXY ." ( HIT ANY KEY TO EXIT MODULE: )"
KEY DROP
THEN THEN ;

-->

SCREEN #121
( DISPLAY NEXT EPISODE TO BE TAKEN )

: CHK DUP 1499 > IF 1440 - THEN 60 /MOD DUP 10 < IF ." 0" . ELSE
  . THEN 08 EMIT ." :" DUP 10 < IF ." 0" . ELSE . THEN 08 EMIT ;
  ( ENTER HERE AT THE SCREEN LOCATION TO PRINT MESSAGE )
: EPI-NEXT 20 EMIT ." NEXT SAMPLE EPISODE:" 20 EMIT ." "
EPISODE# @ 1+ CASE
1 OF ." #1 - SURG - PRE-INDUCTION" ENDOF
2 OF ." #2 - SURG - POST-INDUCTION" ENDOF
3 OF ." #3 - SURG - POST-PERICARDIECTOMY" ENDOF
4 OF ." #4 - SURG - POST-BYPASS (15 MINUTE POST-BYPASS)" ENDOF
5 OF ." #5 - SURG - JUST PRIOR TO CLOSING THE CHEST" ENDOF
6 OF ." #6 - SURG - JUST AFTER CLOSING THE CHEST" ENDOF
7 OF ." #7 - SURG - JUST PRIOR TO PATIENT TRANSPORT" ENDOF
8 OF ." #8 - UNIT - PT - POST-TRANSPORT (PATIENT STABILIZED)"
ENDOF -->

FIG. 18EE

SCREEN #122
( SECOND SCREEN OF NEXT EPISODE DISPLAY )

9 OF ." #9 - UNIT - 30 MINUTES AFTER PT ( "
    EPI-TIME @ 30 + CHK ." :00 )" ENDOF
10 OF ." #10 - UNIT - 1 HOUR AFTER PT SAMPLE ( "
    EPI-TIME @ 60 + CHK ." :00 )" ENDOF
11 OF ." #11 - UNIT - 90 MINUTES AFTER PT ( "
    EPI-TIME @ 90 + CHK ." :00 )" ENDOF
12 OF ." #12 - UNIT - 2 HOURS AFTER PT SAMPLE ( "
    EPI-TIME @ 120 + CHK ." :00 )" ENDOF
13 OF ." #13 - UNIT - 150 MINUTES AFTER PT ( "
    EPI-TIME @ 150 + CHK ." :00 )" ENDOF
14 OF ." #14 - UNIT - 3 HOURS AFTER PT SAMPLE ( "
    EPI-TIME @ 180 + CHK ." :00 )" -->

SCREEN #123
( THIRD SCREEN OF NEXT SAMPLE DISPLAY MODULE )

16 OF ." #16 - UNIT - 4 HOURS AFTER PT SAMPLE ( "
    EPI-TIME @ 240 + CHK ." :00 )" ENDOF
17 OF ." #17 - UNIT - 270 MINUTES AFTER PT ( "
    EPI-TIME @ 270 + CHK ." :00 )" ENDOF
18 OF ." #18 - UNIT - 5 HOURS AFTER PT SAMPLE ( "
    EPI-TIME @ 300 + CHK ." :00 )" ENDOF
19 OF ." #19 - UNIT - 330 MINUTES AFTER PT ( "
    EPI-TIME @ 330 + CHK ." :00 )" ENDOF
20 OF ." #20 - UNIT - 6 HOURS AFTER PT SAMPLE ( "
    EPI-TIME @ 360 + CHK ." :00 )" ENDOF
EPISODE# @ 1+ ." #" .." - ( NO MORE EPISODES REQUIRED )"
ENDCASE ;      -->

SCREEN #124
( FIRST SCREEN OF MENU SELECTION MODULE )

: MENU1 BEGIN 01 WHILE 00 BEGIN DROP
CLS BOX-FULL 20 EMIT 20 02 GOTOXY
."   CONTINUOUS CARDIAC OUTPUT COMPUTER (CCOC) "
20 03 GOTOXY
."    -- INTERACTIVE MODULE LISTING --    " 20 EMIT
10 05 GOTOXY ." SELECTIONS AVAILABLE:"
10 06 GOTOXY ." ———————————"
12 07 GOTOXY ." [1] Electrode Select Screen"
12 08 GOTOXY ." [2] Data Run - Sample Entry Screen"
12 09 GOTOXY ." [3] Start-Up Patient ID Entry Screen"
12 10 GOTOXY ." [4] Enter/Calculate New Cal-factor"
12 11 GOTOXY ." [5] Prepare For Instrument Move"
12 12 GOTOXY ." [6] Restart After Instrument Move"
12 13 GOTOXY ." [7] Review Gathered Patient CO Data" -->

FIG. 18FF

SCREEN #125
( SECOND SCREEN OF MENU SELECTION MODULE )

12 14 GOTOXY ." [8] Help Screen For 'HELP !'"
12 15 GOTOXY ." [9] Screen Listing of Study Sample Run Times"
12 16 GOTOXY ." [0] Terminate Study and Program"
05 22 GOTOXY EPI-NEXT
12 20 GOTOXY ." ****************************************"
12 17 GOTOXY ." ****************************************"
12 19 GOTOXY ." ( # followed by 'ENTER' key )"
12 18 GOTOXY ." Enter Your Selection:......... "
00 BEGIN DROP #IN DUP DUP 00 >= SWAP 10 < AND UNTIL
CLS BOX-FULL 25 02 GOTOXY 20 EMIT
." SELECTION VERIFICATION SCREEN " 20 EMIT
10 06 GOTOXY ." YOU HAVE SELECTED MODULE # " DUP DUP .
10 08 GOTOXY
-->

SCREEN #126
( THIRD SCREEN OF MENU SELECTION MODULE )

CASE
0 OF ." THIS MODULE WILL TERMINATE THE STUDY." ENDOF
1 OF ." THIS MODULE SELECTS IN/OUT ELECTRODE PAIRS." ENDOF
2 OF ." THIS MODULE IS THE DATA ENTRY MODULE." ENDOF
3 OF ." THIS MODULE IS FOR INITIAL PATIENT ID ENTRY ." ENDOF
4 OF ." THIS MODULE ALLOWS FOR CAL-FACTOR ADJUSTMENT." ENDOF
5 OF ." THIS MODULE SAVES DATA PRIOR TO TRANSPORT/MOVE." ENDOF
6 OF ." THIS MODULE LOADS DATA AFTER TRANSPORT/MOVE." ENDOF
7 OF ." THIS MODULE REVIEWS THE PATIENT'S STUDY HISTORY."
     ENDOF
8 OF ." THIS MODULE DISPLAYS USER HELP SCREENS." ENDOF
9 OF ." THIS MODULE DISPALYS A LIST OF STUDY SAMPLE TIMES."
     ENDOF          -->

SCREEN #127
( FOURTH SCREEN OF MENU SELECTION MODULE )

ENDCASE  25 12 GOTOXY ." ****************************************"
         25 13 GOTOXY ." *                                      *"
         25 14 GOTOXY ." *  IS THIS SELECTION CORRECT ?         *"
         25 15 GOTOXY ." *( ENTER 'Y' FOR YES OR 'N' FOR NO )*"
         25 16 GOTOXY ." *                                      *"
         25 17 GOTOXY ." ****************************************"
         57 14 GOTOXY
00 BEGIN DROP KEY DUP DUP 89 = SWAP 78 = OR UNTIL
89 = UNTIL
CASE
1 OF PERIMETER ELECTRODE2 ENDOF  -->

FIG. 18 GG

SCREEN #128
( FIFTH SCREEN OF MENU SELECTION MODULE )

2 OF DATA-MODULE ENDOF
3 OF ENTRY-MODULE ENDOF
4 OF START-CAL ENDOF
5 OF LEAVE-DSK ENDOF
6 OF RELOAD-DSK ENDOF
7 OF REVIEW-DSK ENDOF
8 OF HELP-MODULE ENDOF
9 OF SAMPLE-TIMES ENDOF
CLS 25 10 GOTOXY ." PROGRAM TERMINATED" DROP INT-OFF QUIT
ENDCASE REPEAT ;
-->

SCREEN #129
( SCREEN LISTING PROGRAM )
( ENTER WITH NUMBER OF SCREENS TO BE PRINTED ON TOP OF THE )
( STACK AND FIRST SCREEN TO BE PRINTED SECOND ON THE STACK )
( FOR EXAMPLE: 60 05 LISTING WILL PRINT SCREENS 60 - 64 )
: LISTING   PRINTER SWAP 01 - SWAP BEGIN SWAP 01 + DUP
LIST SWAP 01 - DUP 0= UNTIL CONSOLE ;

-------------------------------------------------------------------------------

SCREEN #140
( FIRST SCREEN OF DATA FILE PRINT-OUT ROUTINE )
: PTAB 27 EMIT 68 EMIT 03 EMIT 13 EMIT 24 EMIT 30 EMIT
43 EMIT 54 EMIT 65 EMIT 74 EMIT 0 EMIT ;
: EP-ON 27 EMIT 69 EMIT ;   : HTAB 9 EMIT ;
: EP-OFF 27 EMIT 70 EMIT ;   : FF 12 EMIT ;
: SET-P PRINTER PTAB EP-ON FF CR HTAB HTAB ."            "
." PATIENT DATA - IMPEDANCE CARDIAC OUTPUT STUDY "
CR HTAB HTAB ."
=================================================" CR CR CR HTAB
HTAB ." FILENAME ===>_____    PATIENT STUDY # ===>_____" CR CR ;
: HEAD PRINTER 4 0 DO HTAB LOOP ."            C.O.     C.O.    HEART    CAL-" CR ;
: HEAD2 ." RECORD#  EPISODE#   RUN #   TIME    THERMO  IMPED    RATE
FACTOR" CR."=========================================
======================================
====" CR CONSOLE ;

FIG. 18HH

CONTINUOUS CARDIAC OUTPUT BY IMPEDANCE MEASUREMENTS IN THE HEART

BACKGROUND OF THE INVENTION

This invention generally relates to medical apparatus for measuring characteristics of a heart. More particularly, the invention relates to a balloon flotation electrode catheter which can be used with appropriate equipment to monitor cardiac outputs on a beat-by-beat basis over a prolonged period of time.

While the invention is particularly applicable to the measurement of cardiac output in the right ventricular chamber of a human heart, it should be appreciated that the measurement of cardiac output in another chamber of a heart, such as the left ventricular chamber and of a nonhuman heart such as a suitable mammalian heart can also be performed by the present invention.

Several parameters are routinely monitored in patients having heart problems or those undergoing cardiovascular surgery. These include the electrocardiogram (ECG), the arterial blood pressure (ART), the central venuous pressure (CVP), the pulmonary artery pressure (PAP), and the cardiac output (CO). With the exception of cardiac output, technology now exists which permits these time varying parameters to be monitored continuously. However, all present techniques for clinically obtaining cardiac output involve indirect methods with sample intervals of several minutes. In addition, these techniques require either the injection of an indicator substance or the gathering of significant respiratory and blood gas patient data.

Cardiac output is generally measured in terms of liters per minute which corresponds to the heart's stroke volume multiplied by heart rate. Cardiac output values change depending on the activity level of the body, the level of metabolic demand, the condition of the heart and many other factors. During major operations, cardiac output is clinically significant because it is an indicator of how well the heart itself is performing and it demonstrates whether a sufficient supply of blood is being circulated to maintain metabolic demands.

One of the indirect methods of measuring cardiac output is the Fick method which determines such output by examining both the oxygen consumption of the lungs and the difference between arterial and venuous oxygen concentrations. A second method involves indicator dilution. Early indicator techniques used injectates such as cardio green dye which was injected as a bolus into the vascular system and allowed to mix with the venuous blood. An arterial sampling through a densitometer was then used to measure the time varying concentration levels of dye. The concentrations recorded were directly related to the flow rate of the dye mixed blood through the circulatory system.

The currently accepted clinical indicator method is a technique known as thermodilution. This method relies on thermal changes as a flow indicator. A bolus of cold fluid, at least 10° C. less than the patient's core temperature, is injected into a venuous site. After mixing in the right ventricle, the adjacent cooled blood and fluid pass a small thermistor temperature sensor which has been placed via a catheter in the patient's pulmonary artery. The time varying temperature changes are directly related to the flow rate of the mixed fluid through the right side of the heart. Since the circulatory system is a series circuit, the right side value is also reflective of the left side ejections. Thus, a cardiac output can be calculated from the indicator dilution curve using a known equation.

Non-invasive techniques for obtaining cardiac output have been recently developed. Echocardiographic instruments can be used to measure aortic sizes and ventricular volumes at specific times during the cardiac cycle. Stroke volumes can then be derived from this information. In this connection, flow doppler instruments have been developed to measure blood velocity via external probes which are placed on the skin of the patient and aimed at a major arterial vessel such as the ascending or descending aorta. Cardiac output is then derived by estimating the vessel diameter in determining blood flow. Further calculations can convert the flow determinations to cardiac output by multiplying the heart rate and the flow per beat. Also, instruments which attempt to measure transthoracic impedance have also been developed in an attempt to determine non-invasive cardiac output. Finally, a non-invasive technique known as the pulse wave contour technique has been developed which makes use of the concept that the area under the arterial waveform curve is related to the stroke volume and the aortic compliance.

Each of the above recited methods has deficiencies which greatly limit either its use and/or functionality for clinical applications, especially during surgery. The Fick principle requires special equipment and careful attention in collecting the required samples and present technology does not allow all of the required patient data to be continuously monitored and analyzed. Non-invasive methods have also demonstrated severe limitations with regard to the size and expense of equipment, the requirement for highly trained personnel and may lead to inaccurate information in patients with cardiac diseases. Finally, the thermodilution technique is not capable of providing real time data on a beat-by-beat basis.

It would be very desirable to provide the clinician with the ability to evaluate cardiac function in certain circumstances, such as with critically ill patients or during surgery, on a continual basis since all other hemodynamic information except cardiac output is currently gathered on a beat-to-beat basis. By obtaining beat-to-beat cardiac output, a hemodynamic assessment of the patient could be performed continuously by the attending staff.

Accordingly, it has been considered desirable to develop a new and improved catheter for measuring cardiac output together with a method for determining the instantaneous volume of blood in a chamber of a heart and a cardiac output monitoring system with which the catheter can be used which would overcome the foregoing difficulties and others while providing better and more advantageous overall results.

BRIEF SUMMARY OF THE INVENTION

In accordance with the present invention, a new and improved diagnostic catheter is provided for measuring cardiac output in the right ventricular chamber.

More particularly in accordance with this aspect of the invention, the catheter comprises an elongated multilumen flexible member having a distal end and a proximal end. A first lumen extends the entire length of the member and terminates in a distal port. A second port extends through the side wall of the member at a location immediately proximate of the distal end of the flexible member and a second lumen extends from the proximal end of the member to the second port. An expandable sleeve surrounds the member and spans the second port. The sleeve is inflatable by a fluid introduced into the proximal end of the second lumen. A plurality of ring electrodes are secured to the outer surface of the member at a predetermined axial spacing. The electrodes include a distal ring electrode located at a first predetermined distance proximal of the distal end of the flexible member and a proximal ring electrode located a second predetermined distance greater than the first predetermined distance from the distal end of the flexible member. The electrodes further include a plurality of intermediate ring electrodes disposed between the distal ring electrode and the proximal ring electrode. A plurality of electrical conductors extend longitudinally through a third lumen in the flexible member from the proximal end of the flexible member and are individually connected to separate ones of a plurality of ring electrodes. A first stiffening member is disposed in a fourth lumen in the flexible member and extends from a third predetermined distance to a fourth predetermined distance.

According to another aspect of the invention, a catheter is provided for measuring cardiac output.

More particularly in accordance with this aspect of the invention, the catheter comprises a catheter body having an outer periphery and a distal section terminating in a distal end and a proximal section terminating in a proximal end. A plurality of spaced electrodes are secured to the body outer periphery along the body distal section. A plurality of electrical leads are provided each one of which extends in the catheter body from a respective one of the electrodes to the proximal end of the catheter body. An elongated rigid means is provided for stiffening a portion of the catheter body. One end of the rigid means is located adjacent a proximal most one of the plurality of electrodes. The rigid means so locates the plurality of electrodes as to space them away from endocardial tissue.

In accordance with still another aspect of the invention, a catheter is provided for measuring cardiac output.

More particularly in accordance with this aspect of the invention, the catheter comprises an elongated flexible multi-lumen catheter body having an outer periphery and a distal section terminating in a distal end and a proximal section terminating in a proximal end. A balloon is attached to the distal end of the body. A first lumen extends the entire length of the catheter body and terminates in a first port which communicates with an interior surface of the balloon. A plurality of spaced electrodes are secured to the body outer periphery along the body distal section proximal of the balloon. A second lumen extends from a distal most one of the plurality of spaced electrodes to the proximal end of the body. A plurality of electrical leads are provided each one of which extends through the second lumen from a respective one of the electrodes to the proximal end of the catheter body. A third lumen is provided which extends longitudinally in the catheter body from the proximal end to a port which is intermediate to the plurality of spaced electrodes.

According to a further aspect of the invention, a method is provided for determining the instantaneous volume of blood in a chamber of an animal heart.

More particularly, the method comprises the steps of inserting an elongated tubular catheter percutaneously into the heart chamber. The catheter has a plurality of longitudinally spaced electrodes on the surface thereof which electrodes are individually connected to a corresponding plurality of terminals at the proximal end of the catheter by conductors passing through the tubular catheter. The longitudinal spacing of the electrodes are such that a distal electrode and a proximal electrode are located at the pulmonic valve and the tricuspid valve of the heart, respectively. The distal electrode and the proximal electrode are driven with a constant current source. The potential signal developed between pairs of sensing electrodes located intermediate the pair of driving electrodes and attributable to the application of the driving constant current source to the pair of driving electrodes is selectively and sequentially detected. The potentials are proportional to the instantaneous impedance of the medium existing between the selected pairs of intermediate sensing electrodes. The detected potential signals are then converted to digital quantities. The digital quantities are applied to a programmed digital computing device. A single corrected instantaneous impedance value is generated for each of the intermediate sensing electrodes determined to lie within the ventricle. The impedance value detected is due to the application of the constant current source to the pair of driving electrodes. A single corrected instantaneous impedance value is calculated for a ventricular segment volume for each pair of the sensing electrodes. The segment volumes for each pair of sensing electrodes are summed to produce the total instantaneous ventricular volume.

According to a further aspect of the invention, an apparatus is provided for measuring the instantaneous volume of blood in a chamber of a heart.

More particularly in accordance with this aspect of the invention, the apparatus comprises an elongated tubular intravascular catheter having a proximal end and a distal end with a pair of drive electrodes attached to the exterior surface thereof and spaced apart from one another by a predetermined distance D1 which is less than the length dimension of a catheter section that is held in the chamber. A plurality of pairs of sense electrodes are attached to the surface of the catheter and longitudinally spaced therealong between the drive electrodes. The pair of drive electrodes and the plurality of sense electrodes are electrically coupled individually to a terminal at the proximal end of the catheter. A constant current source of a frequency $F_1$ is provided together with a switching means which is joined to the terminals for coupling the constant current source to a selected pair of drive electrodes. A signal detector means is connectable through the switching means to predetermined pairs of the plurality of pairs of sense electrodes for producing signal waves corresponding to the impedance of the medium present between a sense electrode pair selected by the switching means attributable to the constant current source. A means is operatively coupled to the signal detector means for sampling the signal waves at a predetermined rate and converting the signal waves to digital values representative of impedance values. A computing means is coupled to receive the digital values. The computing means is programmed to compute the volume of the segments between selected pairs of sense electrodes using the formula Volume = $(i_c \times \rho \times L^2)/V_{EE}$ where $i_c$ is a known constant current source, $\rho$ is the resistivity of the medium, L is the distance between electrodes and $V_{EE}$ is the measured end to end voltage.

According to another aspect of the invention, a continuous cardiac output monitoring system is provided.

In accordance with this aspect of the invention, an elongated tubular intravascular catheter is provided which is adapted for insertion into a patient's heart. The catheter includes a plurality of spaced electrodes positioned on a periphery of the catheter. A distal most one and a proximal most one of the electrodes are configured as drive electrodes and the remaining electrodes are configured as sense electrodes. Each of the electrodes is connected to a terminal located at a proximal end of the catheter. A signal conditioning and control unit is provided which is in electrical contact with the catheter through the catheter terminal. The unit comprises a constant current source, a selector means for coupling the constant current source to drive electrodes and a signal processing means for processing a signal received by the unit. A computing means is electrically connected to the unit for converting signal waves from the unit to digital values and then computing a stroke volume of the heart.

According to still another aspect of the invention, a cardiac output monitoring system is provided.

More particularly in accordance with this aspect of the invention, the system comprises a first signal means for sending analog data related to a stroke volume in a right ventricle of a patient's heart. A signal processing means is provided for processing the analog data from the first signal means into processed analog data. A computing means is provided for converting the processed analog data from the signal processing means to digital values and thereafter computing the stroke volume of the patients heart.

One advantage of the present invention is the provision of a new and improved catheter for use in monitoring stroke volume.

Another advantage of the present invention is the provision of a method and apparatus for measuring stroke volume and cardiac output with an accuracy greater than has heretofore been possible using known prior art techniques.

Still another advantage of the present invention is the provision of a method and apparatus for measuring stroke volume and cardiac output on a beat-to-beat basis in a continuous manner.

Yet another advantage of the present invention is the provision of a catheter which, together with apparatus for measuring stroke volume facilitates the measurement of cardiac output on a beat-to-beat basis. The catheter can also be used in ventricular pacing and the diagnosis of complex arrhythmias.

Still yet another advantage of the present invention is the provision of a balloon catheter having a series of axially aligned electrodes extending over a predetermined length proximally of the balloon such that when the balloon is guided into the pulmonary outflow tract of the heart, the portion of the catheter bearing the electrodes extends between the tricuspid valve and the pulmonary valve of a right ventricle of the heart.

A further advantage of the present invention is the provision of a flow directed catheter having a stiffening member contained in a lumen thereof for causing the catheter to assume the correct orientation in a right ventricle of the heart.

A still further advantage of the present invention is the provision of a method and apparatus for measuring ventricular volume of a heart wherein the catheter is capable of conducting stroke volume measurements using two different techniques so that a comparison or a calibration can be performed.

A yet further advantage of the present invention is the provision of a ventricular volume measuring system including a catheter having electrodes, a signal conditioning and catheter control unit and a microcomputer. The system allows any electrode pair to be selected for use as either sensing electrodes or drive electrodes as desired and the electrodes can be scanned to determine catheter position.

Still other benefits and advantages of the invention will become apparent to those skilled in the art upon reading and understanding of the following detailed specification.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof and wherein:

FIG. 1 is a plan view of a catheter according to the preferred embodiment of the present invention;

FIG. 2 is an enlarged cross-sectional view along line 2—2 of the catheter of FIG. 1;

FIG. 7 is a block diagram of the signal processing unit of FIG. 5.

FIGS. 17A–17I are schematics of the actual circuitry in which an embodiment of the subject system is presented; and FIGS. 18A–18II is a listing of the software modules with which the subject system operates.

DESCRIPTION OF THE PREFERRED EMBODIMENT

Figure 3:
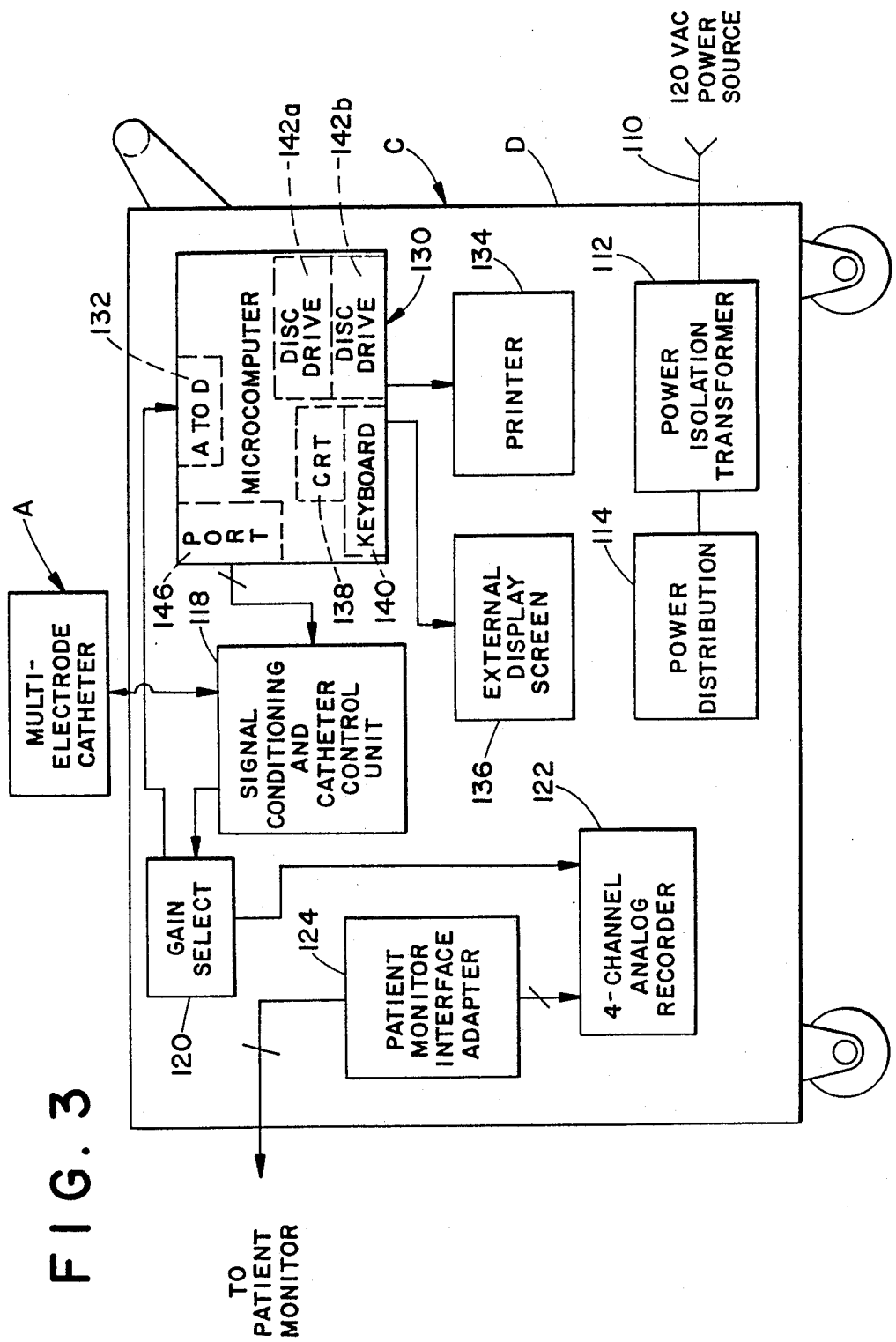
FIG. 3 is a block diagram of a continuous cardiac output measuring system according to the present invention.
Figure 15:
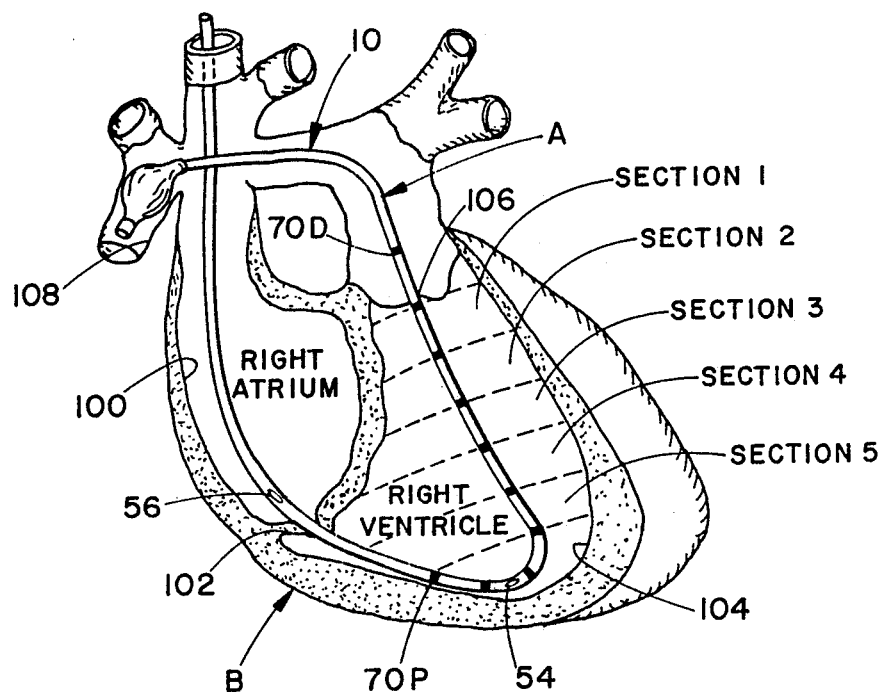
FIG. 15 is a sectional view of a heart showing the catheter of FIG. 1 inserted in the right ventricle.

Referring now to the drawings, wherein the showings are for purposes of illustrating a preferred embodiment of this invention only and not for purposes of limiting same, FIG. 1 shows the subject new diagnostic catheter A which is adapted to be positioned in a heart B as is illustrated in FIG. 15 and is adapted to convey information to the continuous cardiac output measuring system C illustrated in FIG. 3. While the catheter will be described for use in monitoring cardiac output in the right ventricle of a human heart, it should be appreciated that the catheter can be used for monitoring cardiac output elsewhere in the heart, such as in the left ventricle, and can also be used to monitor cardiac output in hearts other than human hearts, such as suitable mammalian hearts and others.

More specifically, the catheter A is a balloon flotation catheter of the type known as a Swan-Ganz catheter. The catheter A comprises an elongated tubular member 10 which can be approximately 110 cm long if desired and which can be made from a plasticized PVC extrusion, if desired. The member 10 is extruded so as to have a predetermined outer diameter which, for purposes of illustration only, may be about a French 7.5 diameter (2.475 mm) and which is preferably formed from silicone rubber, polyurethane or some other suitable plastic that tends to be non-thrombogenic. It should be appreciated, however, that the tubular member could have a diameter between about French 4 (1.32 mm), for pediatric applications, and French 8 (2.64 mm). The tubular member 10 includes a distal section 12 having a distal end 14 and a proximal section 16 having a proximal end 18 which terminates in a pigtail sheath 20.

Extending from the pigtail sheath are a first inlet tube 22, a second inlet tube 24, a third inlet tube 26, and a fourth inlet tube 28. Also extending from the sheath is a first electrical conduit 30 and a second electrical conduit 32. Secured on a free end of the first inlet tube 22 is a connector terminal 34. Similarly secured on the free ends of the second and third inlet tubes 24 and 26 are suitable second and third connector terminals 36 and 38. To a free end of the fourth inlet tube 28 is secured a fluid connector terminal 40 known as a Luer valve. A first electrical terminal 42, which is for the thermistor and can be a three pin Edwards type connector if desired, is connected to a free end of the first electrical conduit 30. Similarly, secured to the free end of the second electrical conduit 32 is a suitable second electrical terminal 44, which is for the electrodes and can include ten pins, if desired.

The distal end 14 of the catheter is provided with a first outlet port 50 which is in fluid communication with the first inlet tube 22 through a first or distal lumen 52 as shown in the cross-sectional view of FIG. 2. Similarly, second and third outlet ports 54, 56 are in fluid communication with a respective one of the second and third inlet tubes 24, 26, through suitable lumens only one of which, 58, is illustrated in FIG. 2 since the port 56 can terminate the other lumen before the cross-sectional view of FIG. 2. A balloon section 60 is in fluid communication with the fourth inlet tube 28 through a third lumen 62 as is illustrated in FIG. 2.

Formed through the side wall of the tubular member 10 in the zone spanned by the balloon 60, is a port, not visible in FIG. 1, which communicates with the third lumen 62. Thus, when fluid under pressure is introduced through the open fluid terminal 40, it flows through the lumen 62 and out the mentioned port so as to inflate the balloon. By then closing the valve 40, the balloon can be retained in its inflated state.

Secured on an outer periphery of the tubular member 10 are a plurality of spaced ring type surface electrodes 70, which can be made from Elgiloy. The electrodes are spaced apart by approximately 0.8 to 1.0 cm and can be approximately 2 mm wide. The most proximal electrode is identified by the numeral 70P and the most distal electrode is identified by the numeral 70D. Preferably, ten electrodes are provided with each of the electrodes being connected to a separate insulated conductor 72 which is positioned in a fourth or electrical lumen 74 as is illustrated in FIG. 2. If desired, the distal-most electrode 70D can be located approximately 9 cm from the distal end of the catheter with the proximal-most electrode being located approximately 16.4 cm from the catheter distal end, when the electrodes are spaced apart by 0.8 cm. Such an electrode spacing may be advantageous for patients with small ventricles. The conductors 72 extend in the fourth lumen proximally to the second electrical terminal 44 and terminate in individual connector pins 76 contained in the terminal or housing 44. The terminal is adapted to be connected to a control unit as described hereinbelow.

Located on the tubular member 10 is a port 80 adjacent the balloon section 60 for holding a conventional thermistor element 82 which is normalized for blood temperature measurement and is disposed within the tubular member. As is well known in the art, a suitable plastic such as polyurethane having good heat conducting properties covers the thermistor in the port 80 in order to prevent the ingress of blood and other body fluids. The thermistor 82 is in electrical contact with the thermistor terminal 42 through a suitable insulated conductor 84 (FIG. 2) which for the sake of convenience, can also extend through the fourth lumen 74 if desired.

As illustrated in FIG. 2, a metallic stiffening member or stylet 90 is suitably disposed in a lumen 92 proximally of the proximal most electrode 70P. If desired, the lumen 92 can be a continuation of the lumen which leads also to the third port or proximal port 56. In order to prevent fluid from flowing further down this lumen, a suitable adhesive plug (not visible) is suitably injected into the lumen at a location distal of the port 56, as is well known in the art.

As is evident from FIG. 2, the tubular member can be a five lumen catheter. However, it should be recognized that the member could also be provided with six or more lumens if that was considered desirable or necessary.

The stiffening stylet 90 can comprise a suitable stainless steel wire which is encapsulated in an insulating material such as nylon. In order to give the wire considerable stiffness, it can be made out of a suitable conventional spring wire if desired. The stylet 90 can be positioned immediately proximally of the proximal most electrode 70P and can extend approximately 10 cm proximally therefrom as is illustrated in FIG. 1. During insertion, the stiffening stylet 90 aids in the proper positioning of the catheter to locate the electrodes away from the heart chamber walls thereby allowing the catheter to be placed in a position which permits impedance measurements.

While the stylet 90 is shown in FIG. 1 as being substantially straight, it should be appreciated that curved, bent, or looped stylets might prove advantageous for certain catheter uses as well. The stylet could be fixed or adjustable as may be required. While the stylet has been illustrated as being made of stainless steel, other types of material, such as for example fiber-reinforced composites may be used instead.

The first lumen 52 which terminates in the first port 50 at the tip of the catheter is useful for monitoring blood pressures during insertion of the catheter. Additionally, blood samples can also be drawn from the first port 50. The third port or proximal port 56 with which the lumen 92 can communicate as explained above, can terminate approximately 30 cm from the distal end of the catheter. When the catheter is correctly inserted in the heart, the port 56 will be located in the right atrium. This port can be used to monitor central venuous pressures and can also be employed as an injection site for fluids and medications. Blood samples can also be obtained through this port.

As mentioned previously, it is advantageous to provide a second port 54 which is located between the series of spaced electrodes 70. The lumen 58 communicating with port 54 can terminate at approximately the 15 cm mark as measured from the distal end locating the port between the eighth and ninth electrodes 70. The port 54 can be used for measuring right ventricular pressures as well as determining catheter location by examining the changes in the pressure wave-form as the port passes through the tricuspid valve and into the right ventricle.

In another embodiment of the invention, ten electrodes can be spaced apart at 1 cm intervals beginning 9 cm from the distal tip of the catheter and terminating 20 cm from the distal tip. A calibrated thermistor bead can be located approximately 4 cm from the distal tip. The catheter can have a balloon of approximately 1.5 cc volume located between the thermistor and the distal tip. A stiffening or stabilizing stylet 10 cm in length can be provided in the catheter between 20 cm and 30 cm from the distal tip of the catheter, that is proximally from the proximal-most electrode. The stylet can be made of stainless steel which is encapsulated nylon.

This catheter can include four lumens, namely, a proximal lumen which terminates 30 cm from the distal end of the catheter for monitoring central venuous pressures, injecting fluids and medications and drawing blood samples; an electrical lumen which contains the leads for the thermistor and each of the ten electrodes; a balloon lumen which is used to control the inflation and deflation of the balloon; and a distal lumen which terminates at the tip of the catheter, for monitoring blood pressures and drawing blood samples.

With reference now to FIG. 15, the catheter A can, if desired, be inserted via the superior vena cava. The site of entry can be an internal jugular, subclavian or antecubital vein. Insertion and final catheter positioning are guided by pressure waveforms and EKG signals obtained from the catheter. The methods employed for introducing the catheter are identical to those used for the insertion of a conventional Swan-Ganz catheter, and, accordingly, no further description of them is considered necessary. Once the distal tip of the catheter has been routed through a right atrium 100 of the heart B, and a tricuspid valve 102 thereof and into the right ventricle 104, and inflating fluid is applied under pressure to the balloon lumen 62 to inflate the balloon 60. As blood is pumped from the right ventricle, the balloon 60 tends to be carried by blood flow through the pulmonary valve 106 and into the pulmonary outflow tract. Once the tip of the catheter has been located in the pulmonary artery, it is advanced until a wedge condition exists, i.e., the inflated balloon lodges in a branch of the pulmonary artery 108.

When correctly located, the proximal electrode 70P is located adjacent the tricuspid valve 102 and the distal electrode 70D is located at the entrance to the pulmonary outflow tract and preferably adjacent the pulmonic valve 106. Once the catheter is installed, stroke volume measurements can be taken using the techniques set out hereinbelow.

One advantage of the pentamerous lumen embodiment of the invention illustrated in FIG. 1, is that the port 54 can be used to inject medications directly into the cardiovascular system even when blood pressure measurements are being taken through the ports 50 and 56. Also, the port 54 will be positioned in the right ventricle (as shown in FIG. 15) which is advantageous for obtaining a good mixing of the medication with the blood.

On the other hand, the port 56 can also be used to inject medication. This port, since it will be positioned in the right atrium (see FIG. 15) will also assure a good mixing of medication with the blood.

Turning now to FIG. 3, a block diagram of a continuous cardiac output measuring system C of the present invention will be described. The entire monitoring system C is contained in the portable cart D. The monitoring system C receives electrical power from a power source connection 110. Power entering through connection 110 passes through an isolation transformer 112, and then to a power distribution network 114 which functions to condition power to appropriate levels and distribute it throughout the system. The power isolation transformer 112 functions to provide a level of patient safety for the equipment when operating in a critical environment.

Figure 4:
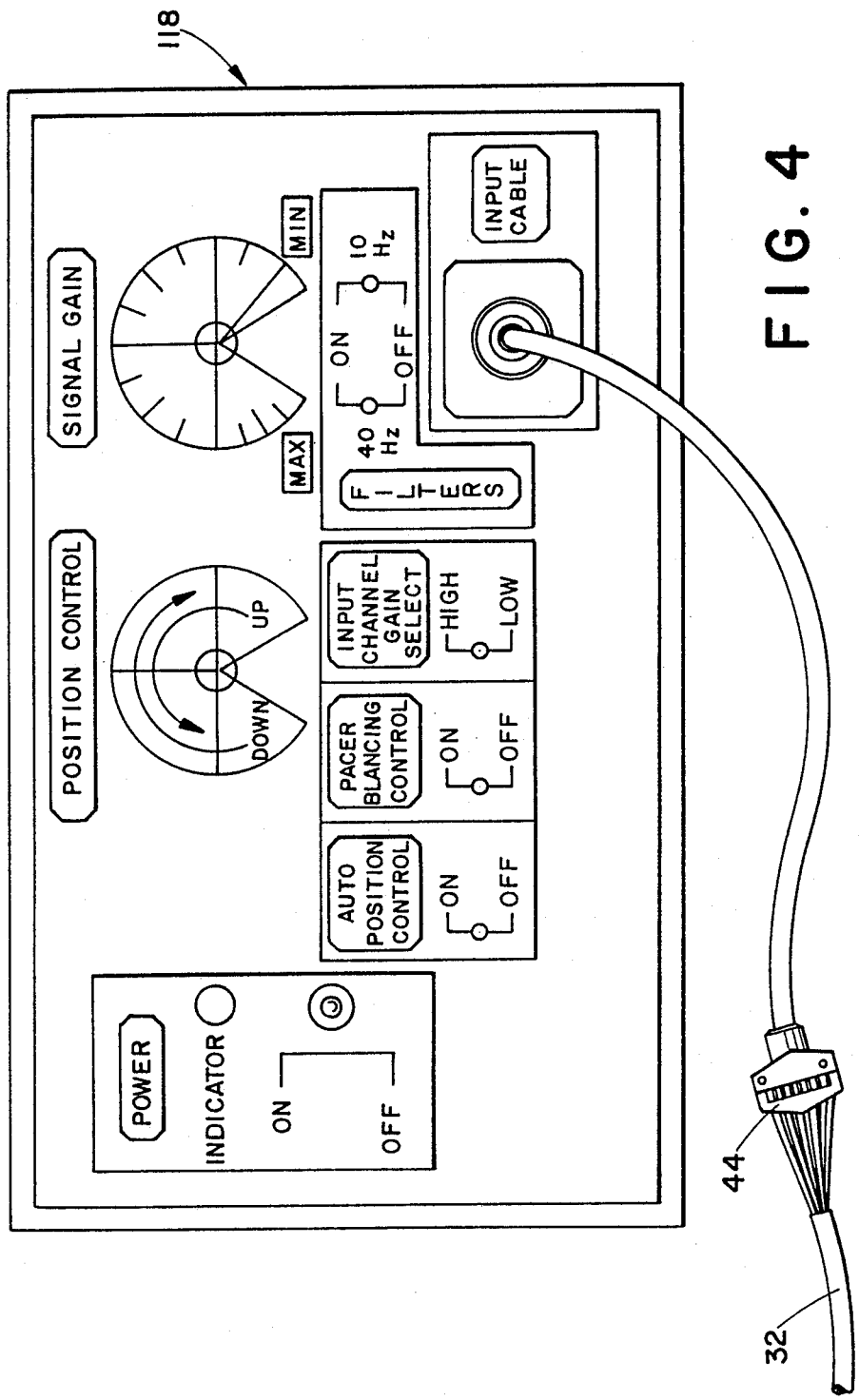
FIG. 4 is a front elevational view of a signal conditioning and control unit housing of the system of FIG. 3 according to the present invention.

Signals received from the multi-electrode catheter A into the continuous monitoring system C are acquired by a signal conditioning and catheter control unit 118 ("SCCCU"), the user interface of which is illustrated more fully by FIG. 4. The SCCCU 118 provides a user interface to control operation parameters of the system. Included is user selected auto position control; pacer balancing controls; input channel gain select; electronic filtration; position control; signal gain; and a master power control.

It will be recalled that analog signals are received by the continuous monitoring system C. Signals received by the unit 118 are passed through a gain select 120 which functions to isolate a desired signal level. Analog outputs from the gain select 120 are fed to a four channel analog recorder 122, which in turn interfaces a patient monitor through an interface adapter 124. Analog signals from the gain select 120 are also fed to a microcomputer 130 via an analog to digital ("A to D") interface 132. In this fashion, a digital signal representative of the analog values obtained from the multi-catheter electrode A is obtained for use in the microcomputer 130 which, in the preferred embodiment, is digital. The microcomputer 130 will be described more fully in conjunction with FIG. 10, below.

The microcomputer 130 is also in data communication with a hard-copy data recorder illustrated by printer 134. The microcomputer 130 is also similarly in data communication with an external display such as that illustrated by display screen 136 which is suitably comprised of a conventional cathode ray tube ("CRT") display. The microcomputer 130 is also shown as including a contiguous CRT monitor 138, a data entry device such as key board 140, and a mass storage medium 142 which is illustrated as a pair of disk drives 142a and 142b. The mass storage medium 142 is suitably comprised of a hard disk, a floppy disk, a CD-MEMORY (compact disk memory), or the like, or any combination thereof. A data port 146, which is suitably comprised of a parallel port or a serial port, provides a means for communicating data to an exterior of the microcomputer 130. As illustrated, the data port 146 communicates data back to the signal conditioning and catheter control unit 118 in a feed-back manner.

Figure 5:
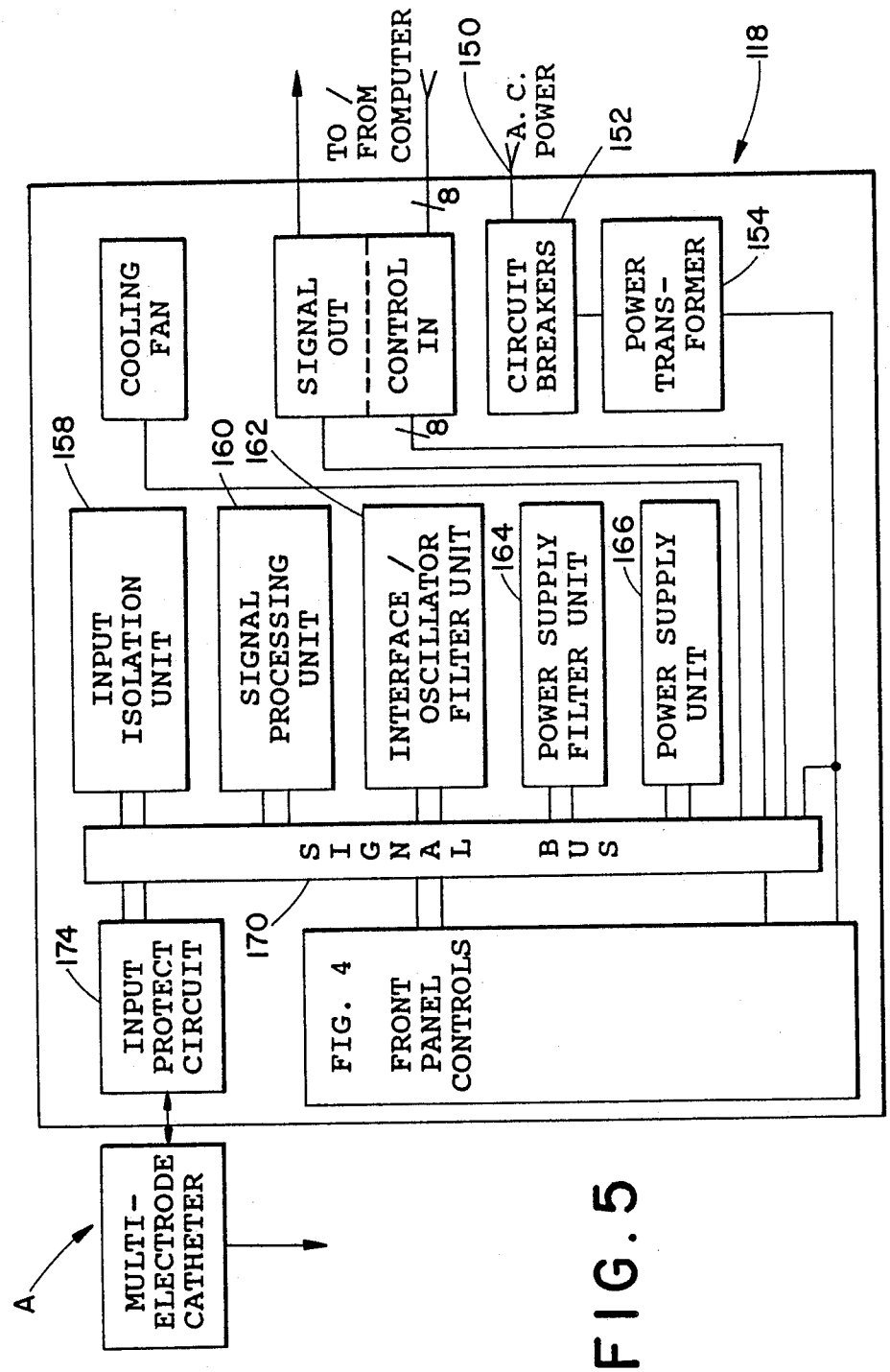
FIG. 5 is a block diagram of the electronic modules within the signal conditioning and control unit of FIG. 4.

Turning now to FIG. 5, a block diagram of the signal conditioning and catheter control unit 118 is presented. Power is received into the SCCCU unit 118 via interconnect 150 which is in turn connected to the power distribution network 114 (FIG. 3). The power network interfaces circuit breakers 152 and a power transformer 154, which steps down the voltage therethrough to suitable levels for operation of the remaining circuitry. The control unit 118 includes primary circuit modules comprising an input isolation unit 158, a signal processing unit 160, and interface/oscillator/filter unit 162, a power supply filter unit 164, and a power supply unit 166. All devices are interfaced via a common signal bus 170. The signal bus 170 also interfaces the control panel of FIG. 4.

The power supply unit 166 receives power from the power transformer 154, stepping it down to appropriate values for use throughout the control unit 118. The voltage levels obtained from the power supply unit 166 are filtered, prior to distribution to the remaining circuitry of the unit, by power supply filter unit 164.

Use of the common connector bus 170 provides a means by which any or all of the above units may be implemented by "plug-in" modules which facilitates selective replacement, enhancement, or modification. Implementation of this bus structure also provides for minimization of noise problems.

The signal bus 170 also interconnects the multielectrode catheter A via an input protection circuit 174. The input protection circuit 174 isolates the signal bus 170, and accordingly the remaining components interfaced thereto, from voltage levels which may otherwise damage circuitry within the control unit 118.

Figure 6:
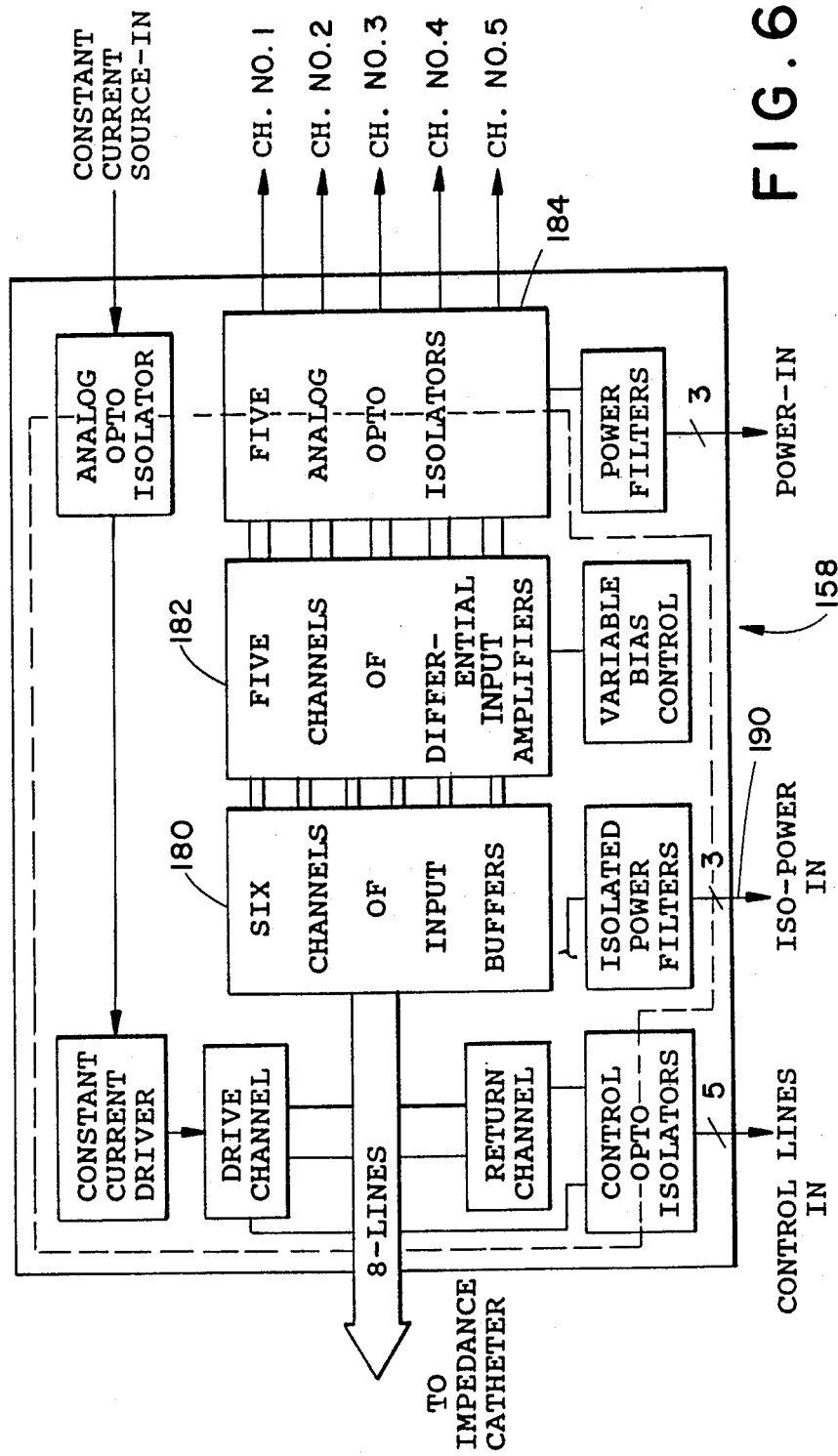
FIG. 6 is a block diagram at the input isolation unit of FIG. 5.

Turning to FIG. 6, the input isolation unit 158 will be described in detail. The input isolation unit 158 contains circuitry which provides five channels of input isolation, a constant current source, electrode select control, and ground isolation. All signals, as well as power entering or leaving this module, are isolated via optoisolators or transformer coupling. Blocks within the dash line of FIG. 6 are isolated. Blocks through which the dash line passes are providing the isolation. Block 180 illustrates a series of six high impedance voltage follower amplifiers which function as buffers between the multi-electrode catheter and the remaining circuitry. Outputs from the input buffers 180 are in turn fed to a series of five channels of differential input amplifiers illustrated by block 182. Signals resultant from the amplifiers 182 are in turn fed outward, again through the signal bus 170 (FIG. 5) via a group of optoisolators 184. The opto-isolators isolate the signals passed therethrough from the next stage via optic coupling. This circuitry is powered via a transformer coupled with non-earth ground references. This forms the iso-power input 190. The iso-power used is referenced to a potential known as isolated ground. Isolated ground is not tied to earth ground. This feature provides a level of patient isolation preventing currents which are flowing due to ground reference potentials from passing into this circuitry. Each optical coupler provides a signal isolation well above several thousand volts.

Turning to FIG. 7, fabrication of the signal processing unit 160 of FIG. 5 will be described. The signal processing unit 160 contains circuitry which provides AC buffering, bandpass filtering, amplitude demodulation, signal smoothing, signal inversion, and waveform isolation. FIG. 7 depicts a signal flow and control related to this module. The board is connected, via the signal bus 170, to two external devices. These external devices include a circulating fan (not shown) via an interconnect 192, and an offset control (not shown) via an offset control interconnect 194. Unlike the circuitry of FIG. 5A the signal processing unit 160 includes no circuitry which uses isolated power. Outputs of the optoisolators 184 from FIG. 6 form an input to AC buffering circuitry 200. This circuitry buffers analogously to the buffers 180 of FIG. 6. Waveforms from the buffer circuitry 200 are passed to a series of five 2 Khz bandpass filters 202. Use of multi-feedback active bandpass filters permits modulated signals of up to 40 Hertz to pass with minimal effect. The filters are implemented given that the modulated impedance signals contain frequencies of up to 40 Hertz. The bandpass filters effectively block undesirable physiologic signals such as electrical signals generated by the contractions of the heart.

After the bandpass filters 202, the signals are passed into five channels of amplitude demodulation present in demodulation circuitry 204. In this circuitry, each channel of impedance waveforms is amplitude demodulated by an absolute value and wave smoothing circuit comprised of a pair of operational amplifiers. The output waveforms from each of these stages is a demodulated signal with some carrier frequency noise. The signals are next passed to a low pass filter 206 to further reduce carrier frequency noise. The low pass filters 206 are suitably comprised of Butterworth-type filters with a maximally flat frequency response. Attenuation is suitably 12 dB at twice the cutoff frequency of 100 Hertz. Signals after the 100 Hertz low-pass filters represent real time dynamic impedance waveforms for each of five selected pairs of electrodes from the catheter A (FIG. 1).

Signals are next fed to a signal inversion circuit 210. In this stage, each impedance value is inverted to form an admittance value. The admittance signal level is desired as it forms a signal from which volume to be measured is directly proportional. The signal inversion circuit functions by implementation of an analog divider chip. Impedance signals are used as denominator values, while an adjustable but constant voltage is used for a numerator. With these two analog voltages, a real time quotient (admittance) is developed for each channel which is inversely proportional measuring impedance values. One of two resistive voltage dividers can be selected, via the front panel control of FIG. 4, to determine the constant numerator voltage.

Output from channels are selected from the signals from the signal inversion circuit 210 by channel selector circuit 212. Such selection is accomplished by means of a signal on waveform select control lines which are obtained as described further below. These control lines determine whether a particular channel is selected. In the event a channel is not selected, no connection is made to further stages, thereby leaving the circuitry open or at a high impedance state. Accordingly, the channel selector circuitry 212 functions analogously to a tri-state device. Outputs from the channel selector circuit 212 form inputs to a waveform summing amplifier 216. The summing amplifier 216 generates a composite waveform, which in turn forms an input to an offset adjust buffer 218. In the offset adding circuit 218, an externally selected DC level adds a value to the composite admittance waveform resultant from the summing amplifier 216. This functions to "window" the waveform within the range of an analog to digital convertor which is implemented in the computer 132 (FIG. 3).

Figure 8A:
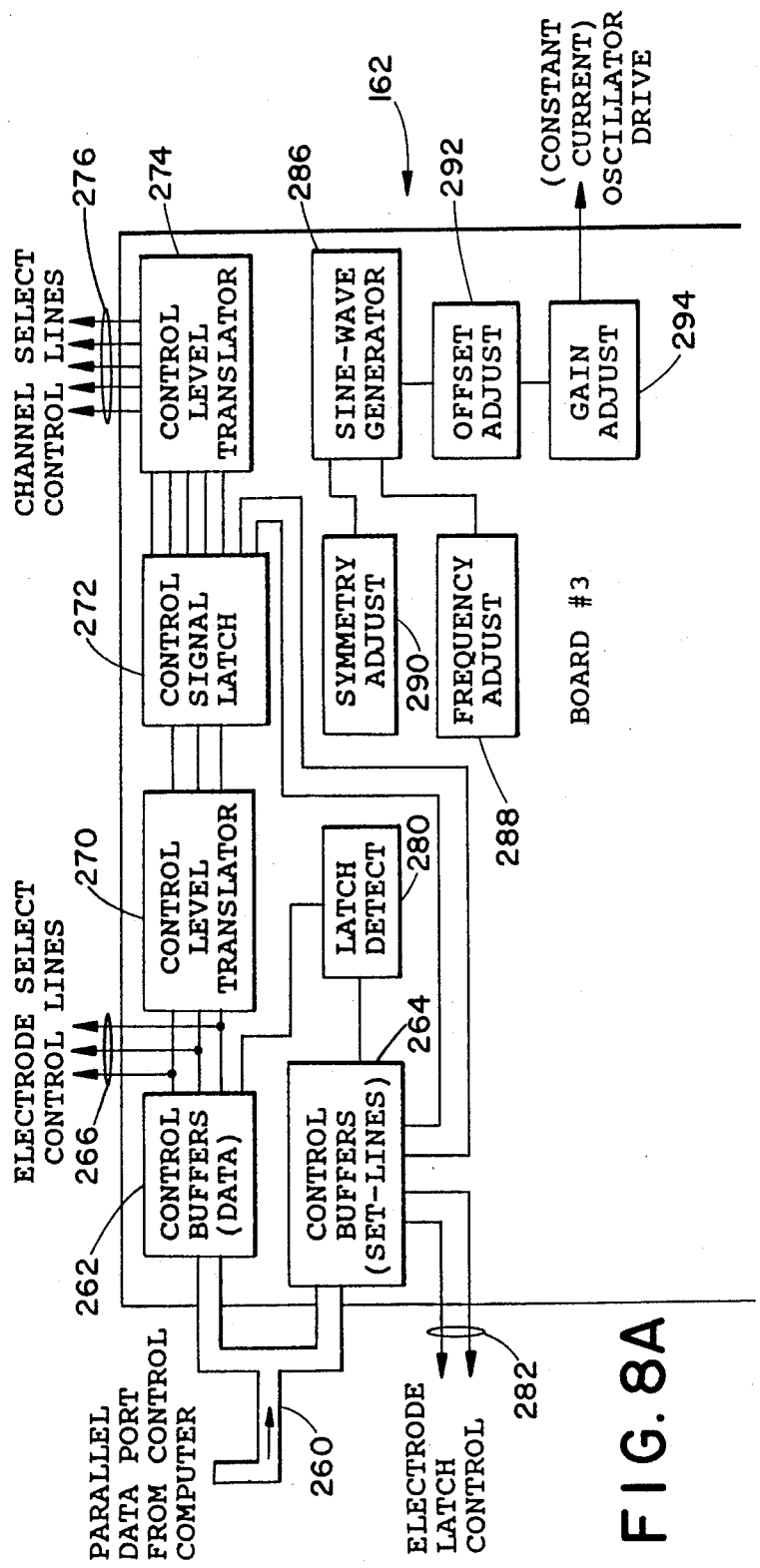
FIG. 8 is a block diagram of the interface/ oscillator unit of FIG. 5.
Figure 8B:
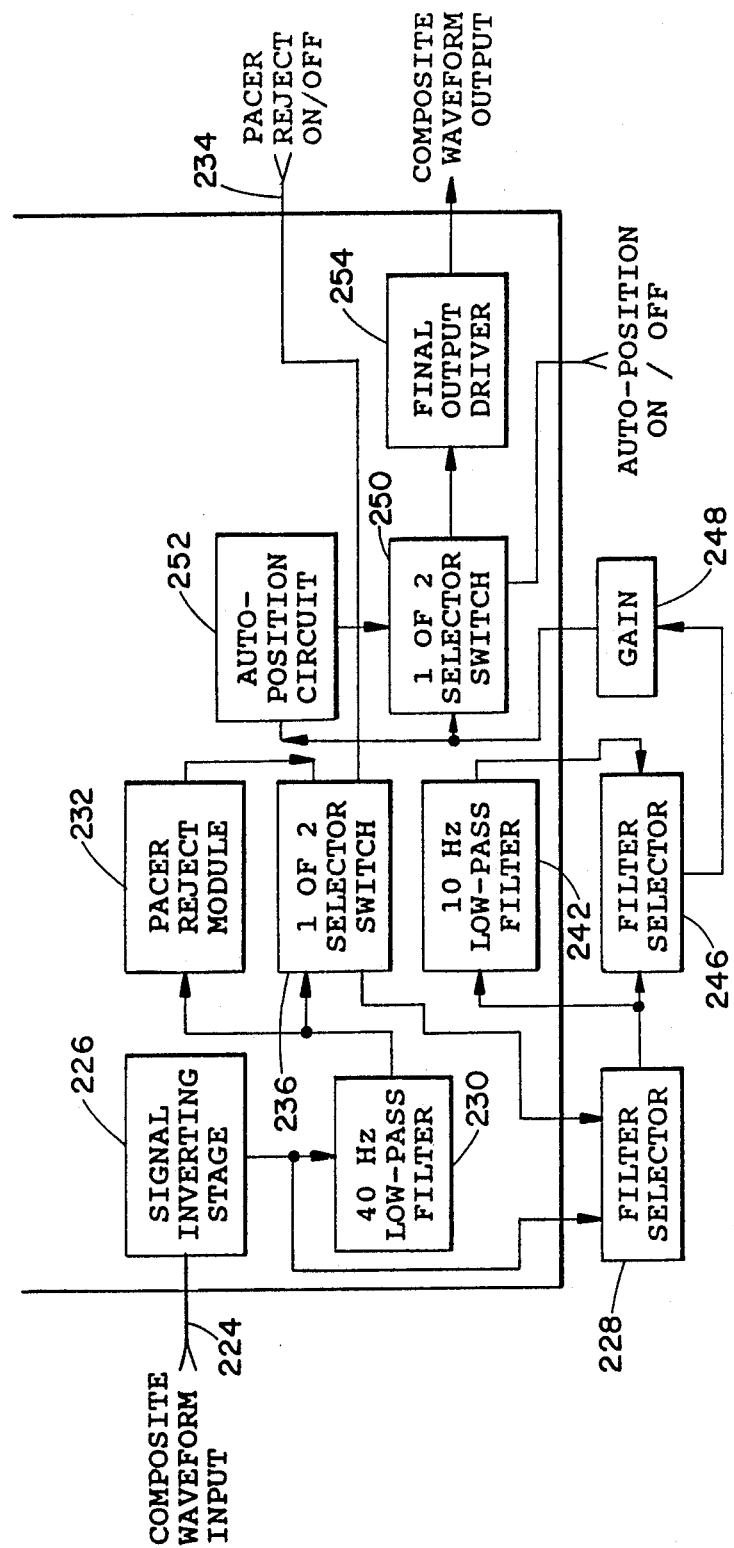

Turning now to FIG. 8, fabrication of the interface/isolator/filter unit 162 will be described. The interface/isolator/filter unit 162 provides interface buffering, latching control, constant current source development, control level shifting, waveform filtering, pacemaker rejection, and auto positioning. The composite admittance waveform developed by the signal processing unit 160 of FIG. 7 is routed via interconnect 224 to circuitry which accomplishes the above-stated operations. The interconnect 224 receives its signal from an output 220 of the waveform summing amplifier 216 to FIG. 7. The composite waveform input obtained from interconnect 224 enters a signal inverting stage 226 which is comprised of an inverting buffer with unity gain. The output from the inverter 226 forms an input for a filter selector switch (single pole, double throw) 228 on the panel of FIG. 4. The selector switch permits operator selection of an inline 40 Hertz filter or a straight-through non-filtered waveform.

The output from the signal inverting stage 226 also forms an input to a low-pass filter 230. An output of the 40 Hertz low-pass filter is selectively fed to the filter selector 228 through a pacer reject module 232 prior to being additionally fed to the filter selector 228.

The pacer reject module is implemented in conjunction with the signal placed on pacer reject line 234 which controls a selector switch 236. A signal on the pacer reject line 234 is user selected by the control panel of FIG. 4. The pacer reject circuitry is comprised of a slew rate limiter fabricated from a diode bridge circuit. The circuitry functions by saturating if a feed-back path coupled to an RC network is not at the same voltage as its input. A state of the feed-back path is determined by the slew rate of the input signals. For dynamic values greater than 50 Hertz, the output of the amplifier saturates. Saturation may be positive or negative depending on a direction of a detected signal spike. Upon activation, the circuit deselects the actual wave-form and connects the output to a high impedance source. This essentially forces the circuit to behave as a sample and hold circuit, thus locking out spike potentials from the pacer and forcing the circuit to remain at its last detected value.

The operator selected signal from filter selector 228 is passed to a low pass filter 242 and a filter selector 246. The filter selector 246 functions to selectively pass the output of the filter selector 228 through the 10 Hertz low-pass filter 242 prior to passing it to a gain select potentiometer 248 which is also found in FIG. 4.

The output of gain potentiometer 248 is selectively placed, via selector switch 250, through an auto-position circuit 252, prior to being fed to a final output driver 254. The auto-position circuit 252 inverts the polarity of the signal.

Turning to the top portion of FIG. 8, parallel data from the microcomputer 130 is input to the interface/oscillator/filter unit 162 via a data bus 260. Data enters control buffers 262 and 264. The buffer 262 holds admittance select-channel data with the buffer 264 holding electrode select-line information. The lines 266 form the electrode select control lines which are coupled directly to the catheter A.

Data from the buffer 262 is also fed to a control level translator 270 to provide for control within the interface/oscillator/filter unit 162. These signals are latched by control signal latch 272, and translated by control level translator 274 which converts them to voltage levels suitable for a logic control external of the unit 162. The voltages levels are made available on channel select control lines 276.

Latch detect circuitry 280 triggers a control pulse at its output in response to a low to high transition on its input port, which is derived from an output of the control data buffer 262. In response to an output of latch detect 280, data from the select-lines control buffer 264 is made available at lines 282.

A sine wave generator 286 has its frequency and symmetry adjusted by controls 288 and 290, respectively. The sine wave generated by this circuit is routed through an offset adjust 292 and a gain adjust potentiometer 294. These components form a constant current source for use elsewhere in the circuit which also includes an isolator.

Figure 9:
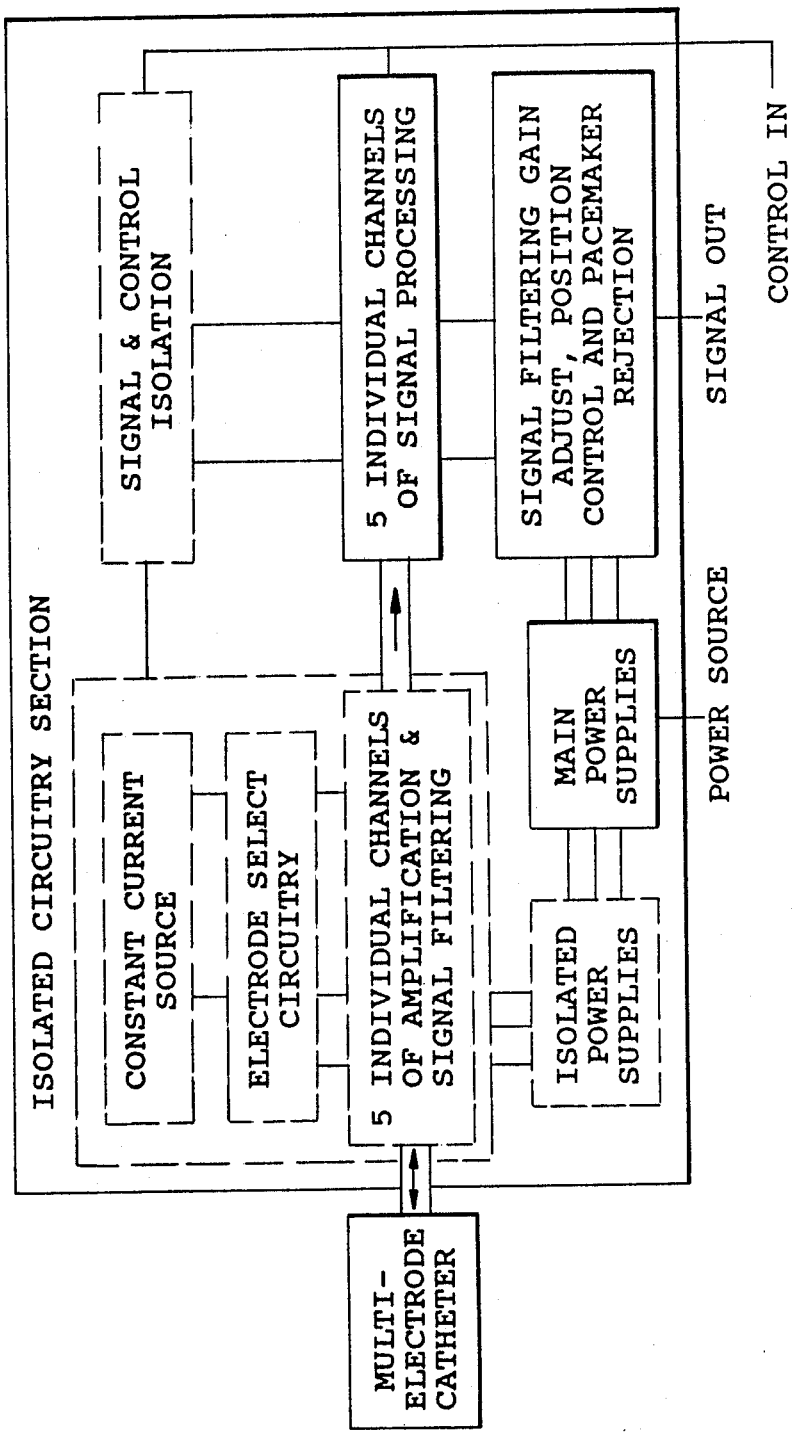
FIG. 9 is a block diagram of the major sections of the signal conditioning and catheter control unit of FIG. 4.

Turning to FIG. 9, a summary of the interaction of all hardware components illustrated in conjunction with FIGS. 5–8 as presented.

Figure 10:
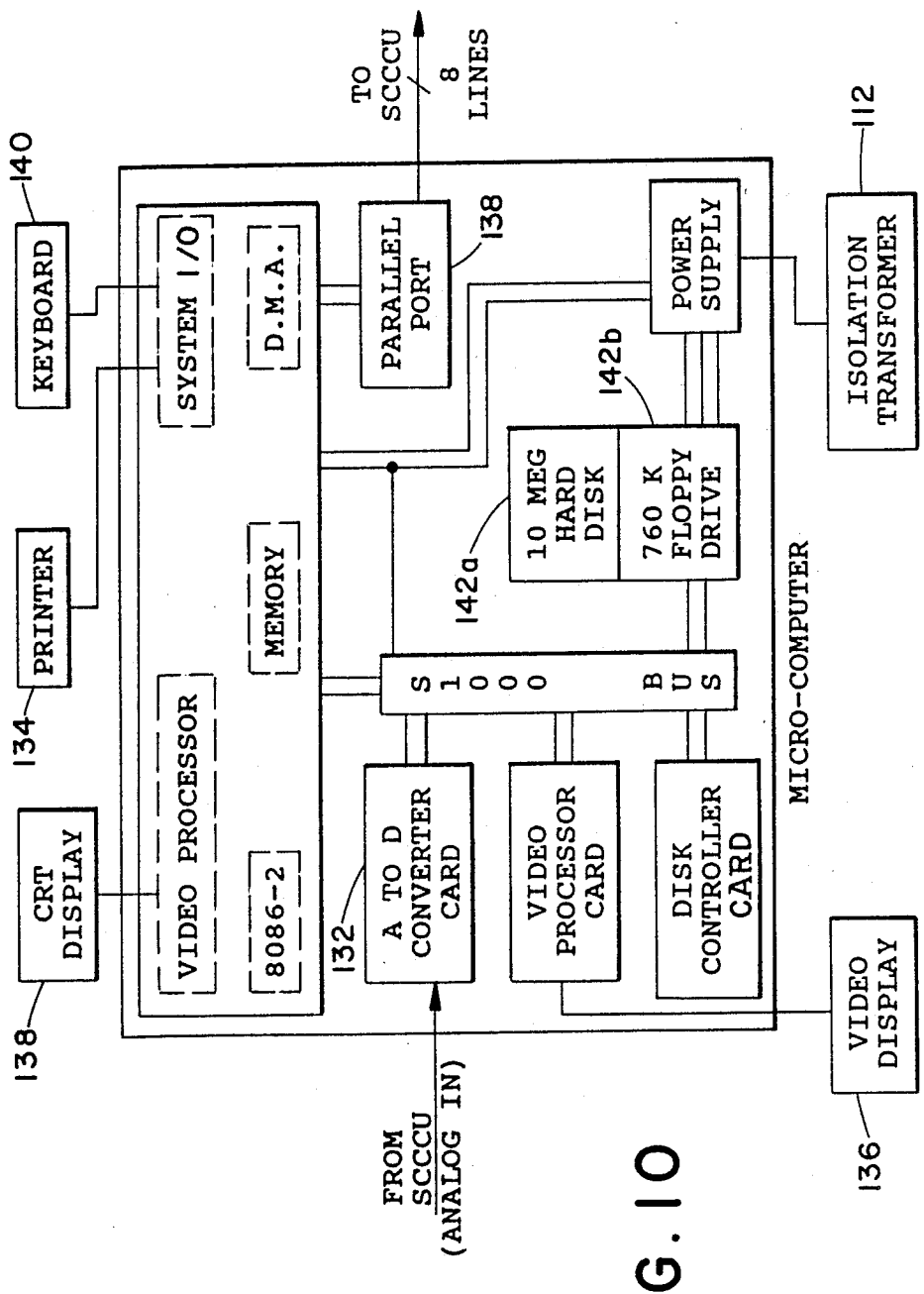
FIG. 10 is a block diagram of a microcomputer of the system of FIG. 3.

Turning now to FIG. 10, a more detailed description of the microcomputer 130 as implemented in the preferred embodiment is presented. It will be noted that the microcomputer is illustrated as based on an 8086-2 microprocessor, of Intel Corp. of Santa Clara, California. Suitable computers having the characteristics illustrated by FIG. 10 are commonly available in the market.

Figure 11:
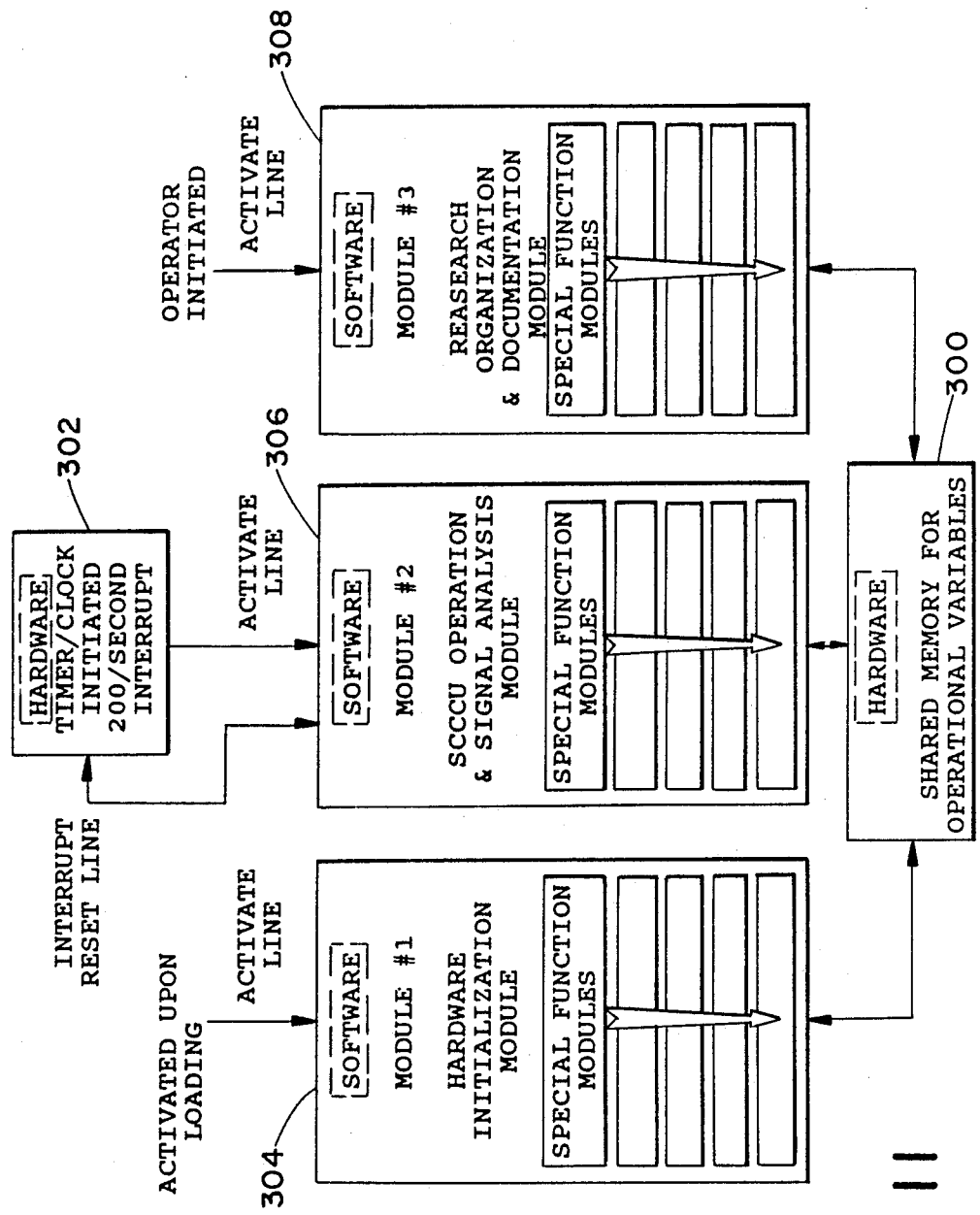
FIG. 11 is a block diagram of the three primary software modules utilized in the computer of FIG. 10.
Figure 12:
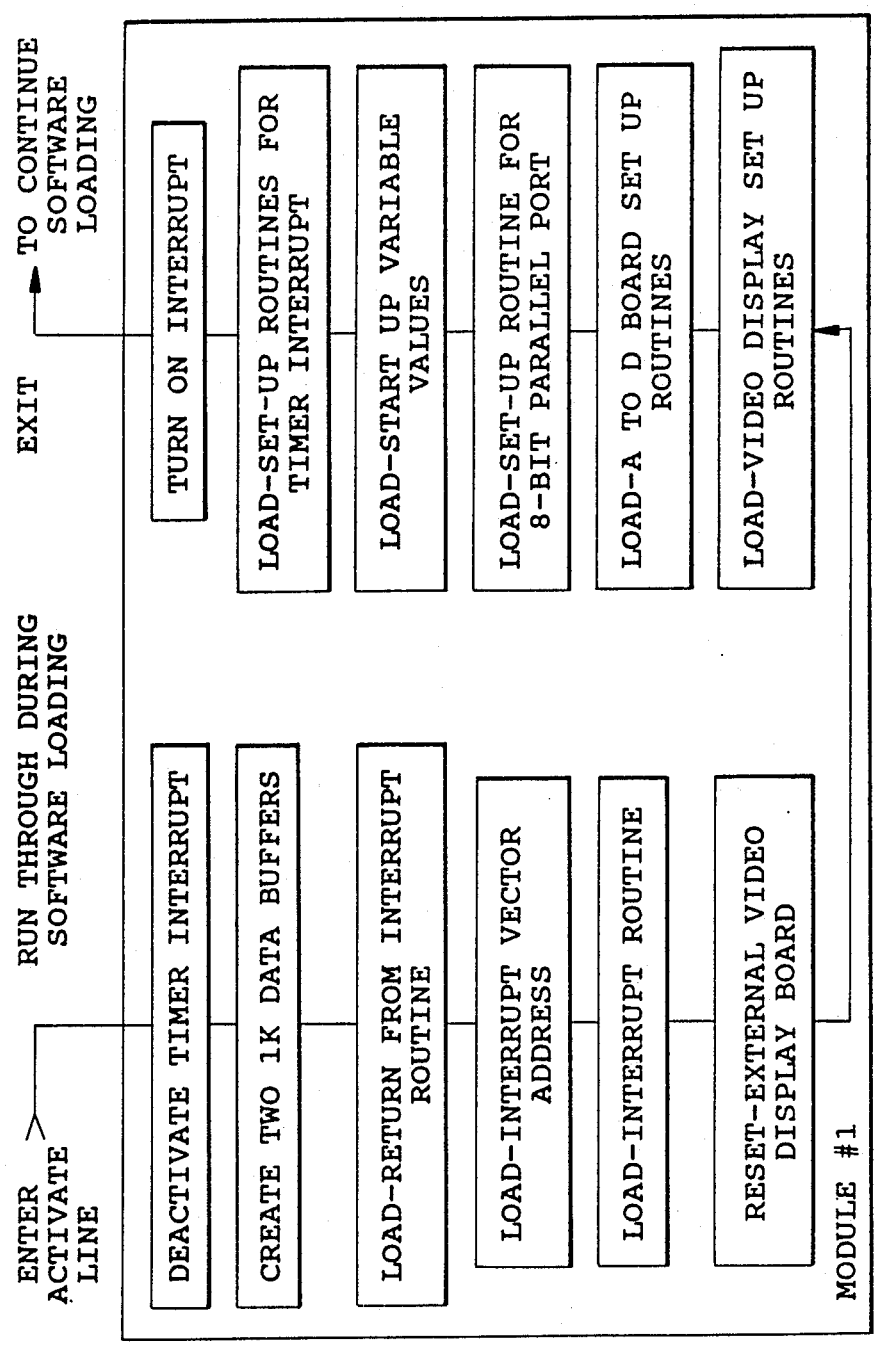
FIG. 12 is a flow diagram of the software routines in module 1 of the modules illustrated in FIG. 11.
Figure 13A:
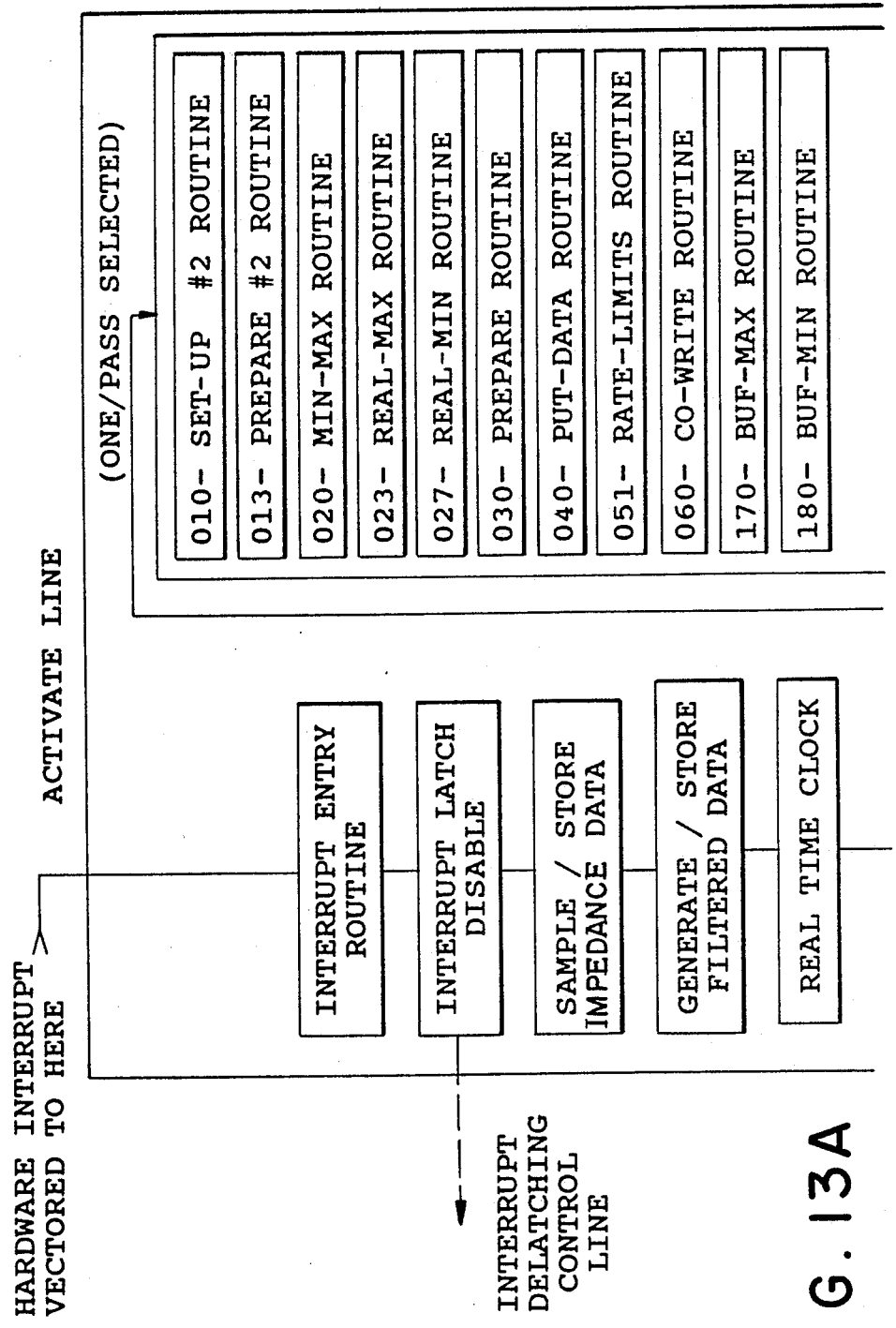
FIG. 13 is a flow diagram of the software routines in module 2 of the modules illustrated in FIG. 11.
Figure 13B:
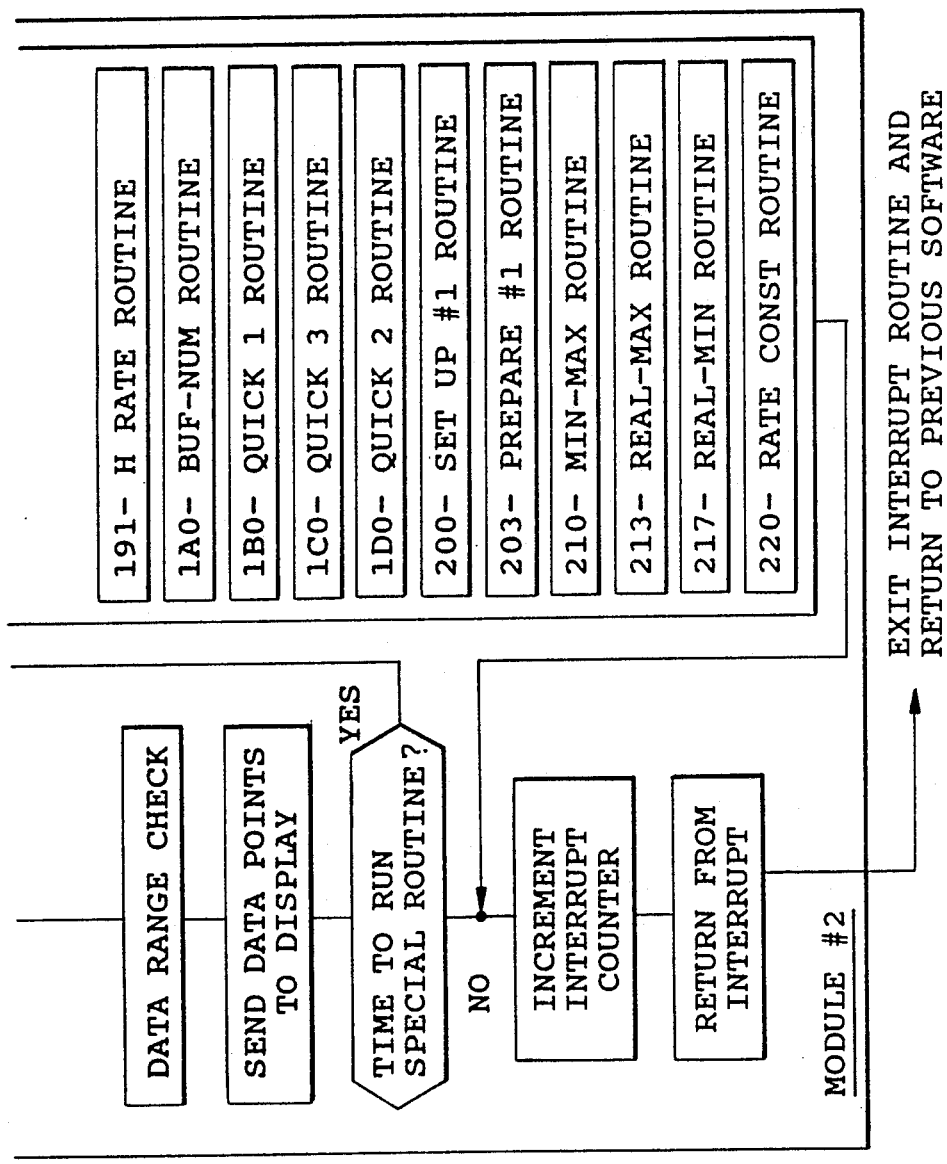

Turning now to FIGS. 11–13, a software routine for the microcomputer of FIG. 10 will be disclosed. With particular reference to FIG. 11, the three primary software modules and their interactions will be described.

Figure 14:
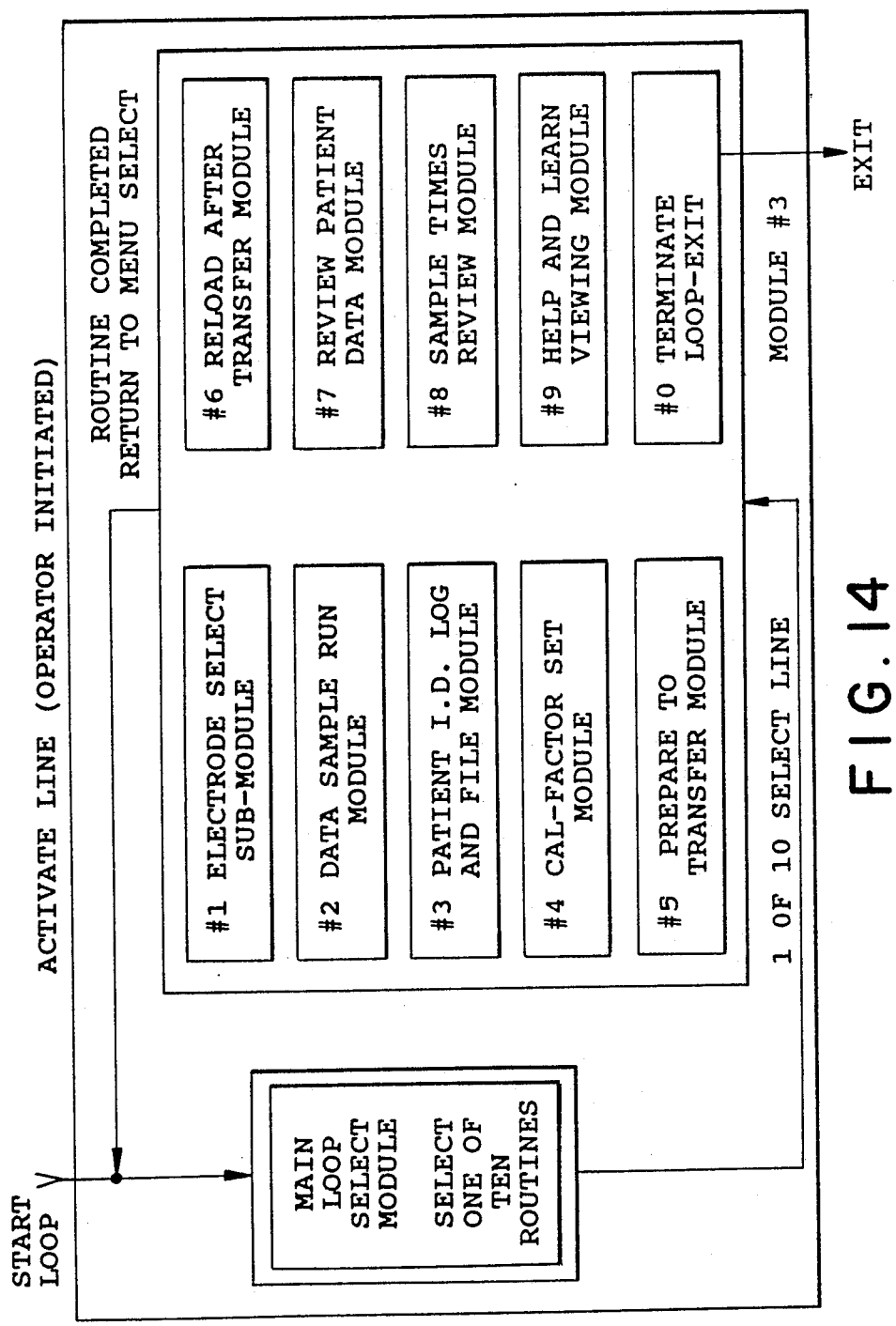
FIG. 14 is a flow diagram of the software routines in module 3 of the modules illustrated in FIG. 11.

FIG. 11 shows common structural links between modules and how they are initiated. A shared or common memory 300 is provided to hold variables which are used by all modules or units in the subject system. This provides means by which modules which may have been programmed in different languages are able to change a state of a stored variable independently of one another. Each routine is initiated without respect to a status of any other routine. SCCCU operation and signal analysis is operationally separated from other code modules, but by virtue of the shared memory 300, shares common variables with other code sections. Activation is preferably not user controlled, but instead is a function of a hardware timer and clock circuit 302 which activates the module at a frequency of suitably 200 times per second, regardless of a state of the remaining modules. This section of code is essentially running in the background while all other code is running in the foreground. Because of its mode of activation, the SCCCU operation and signal analysis module has priority over other code modules. This module is termed "free-running" and requires no operator interaction to begin or complete its task. The software routine implemented in modules 1, 2, and 3 (304, 306, and 308 respectively), are illustrated in FIGS. 12, 13, and 14, respectively.

Figure 16:
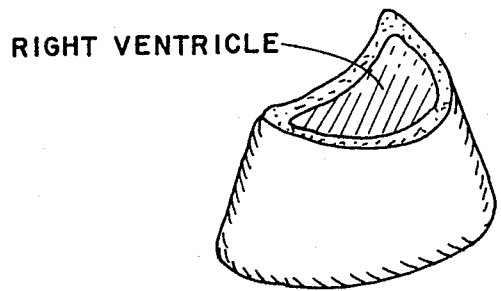
FIG. 16 is a perspective view of a removed section of the right ventricle of the heart of FIG. 15.
Figure 17A:
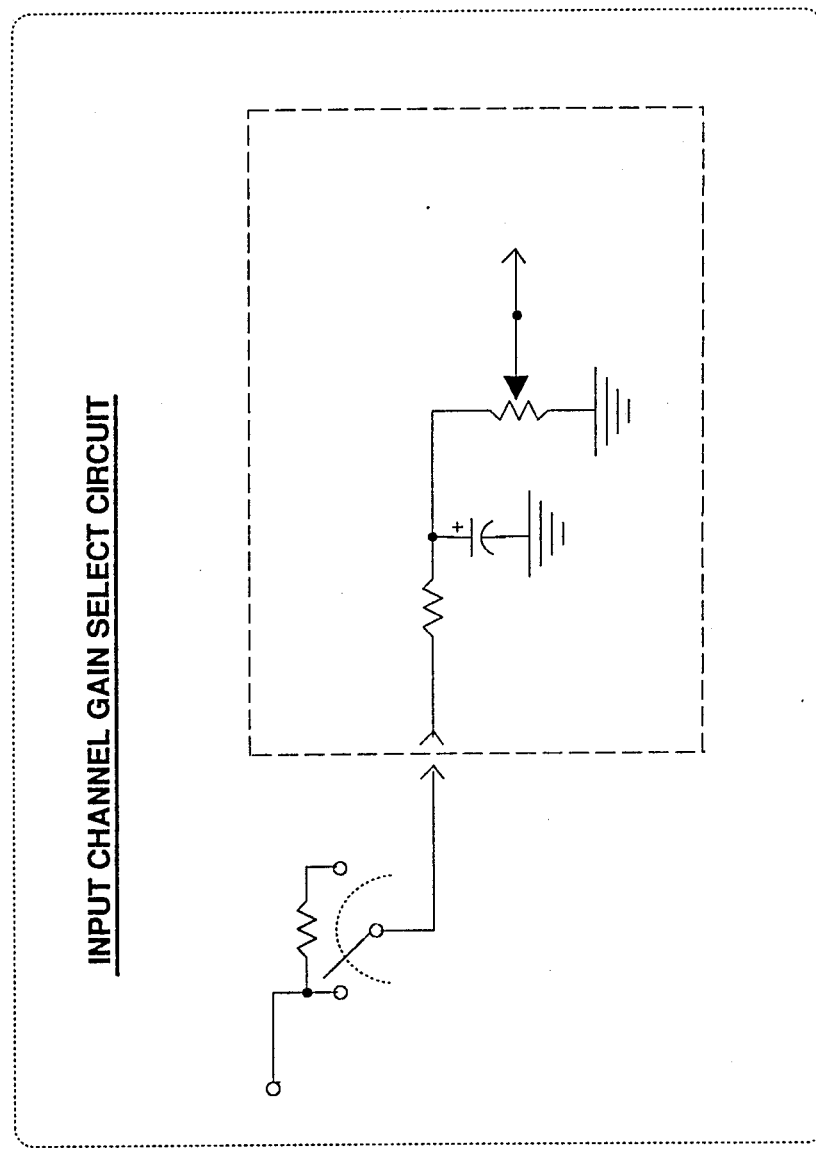
Figure 17B:
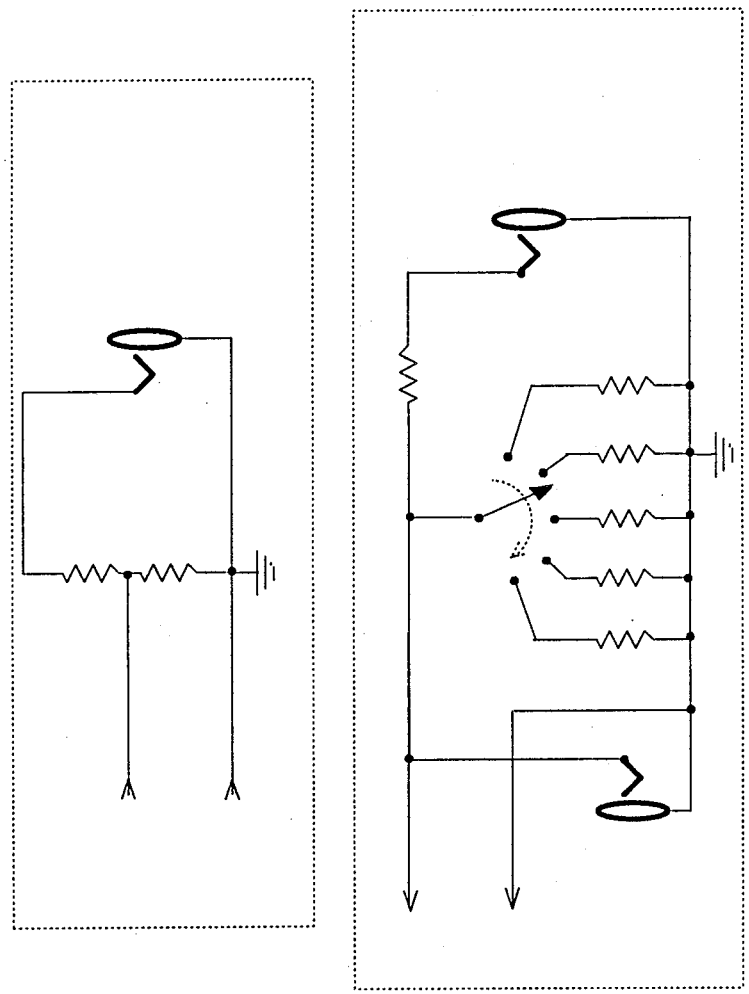
Figure 17C:
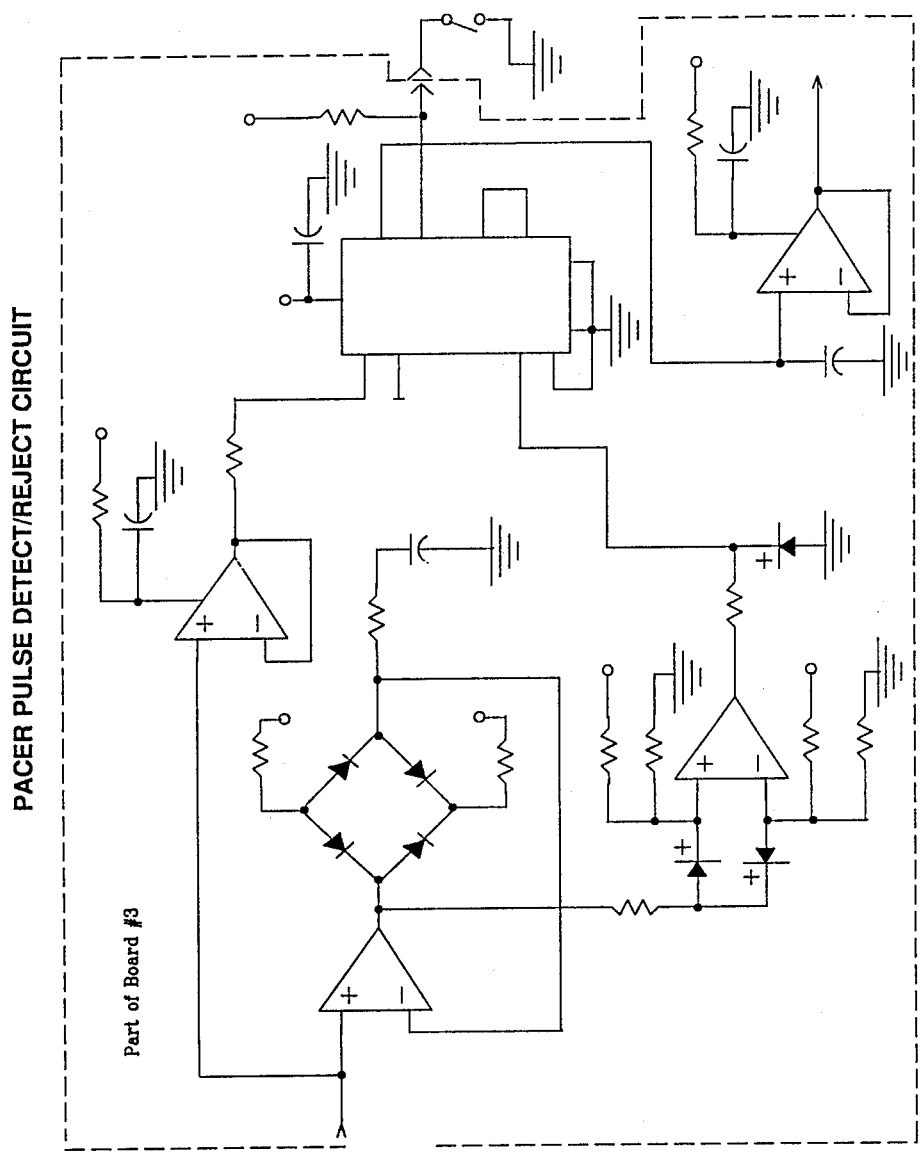
Figure 17D:
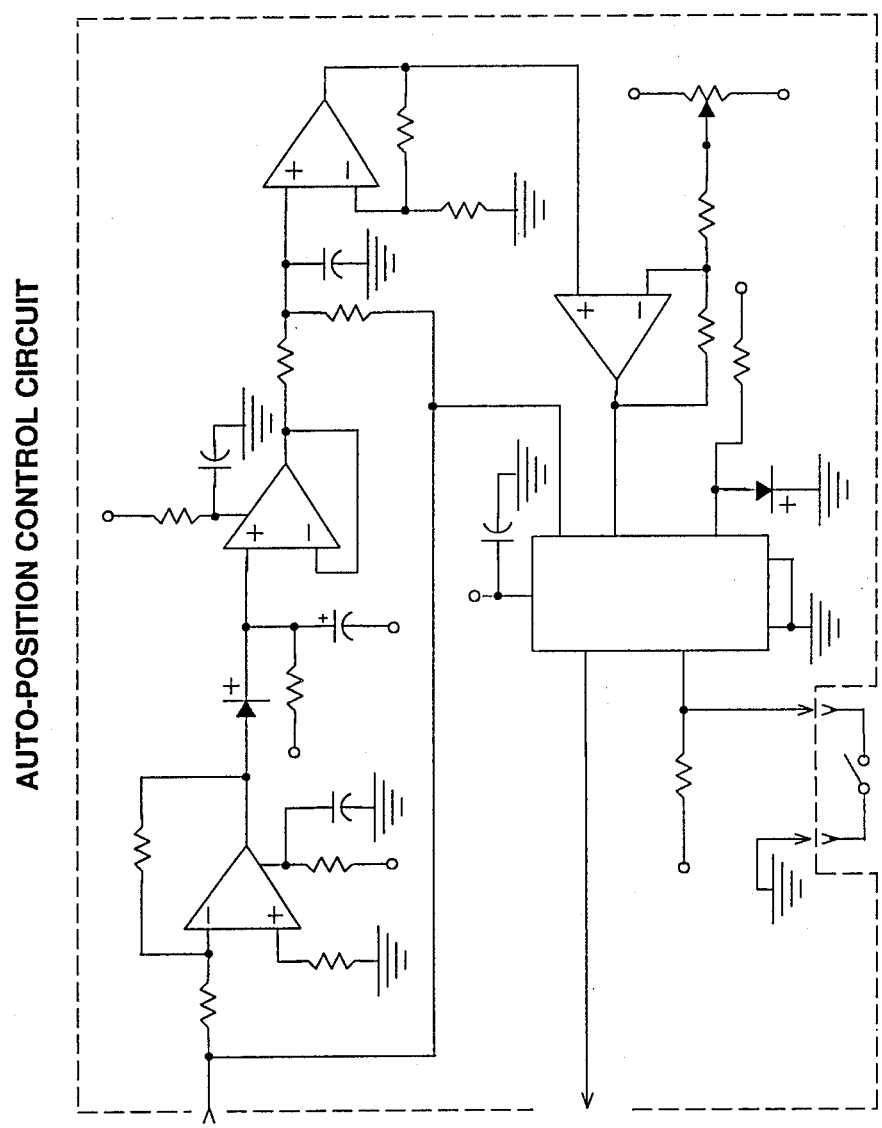
Figure 17F:
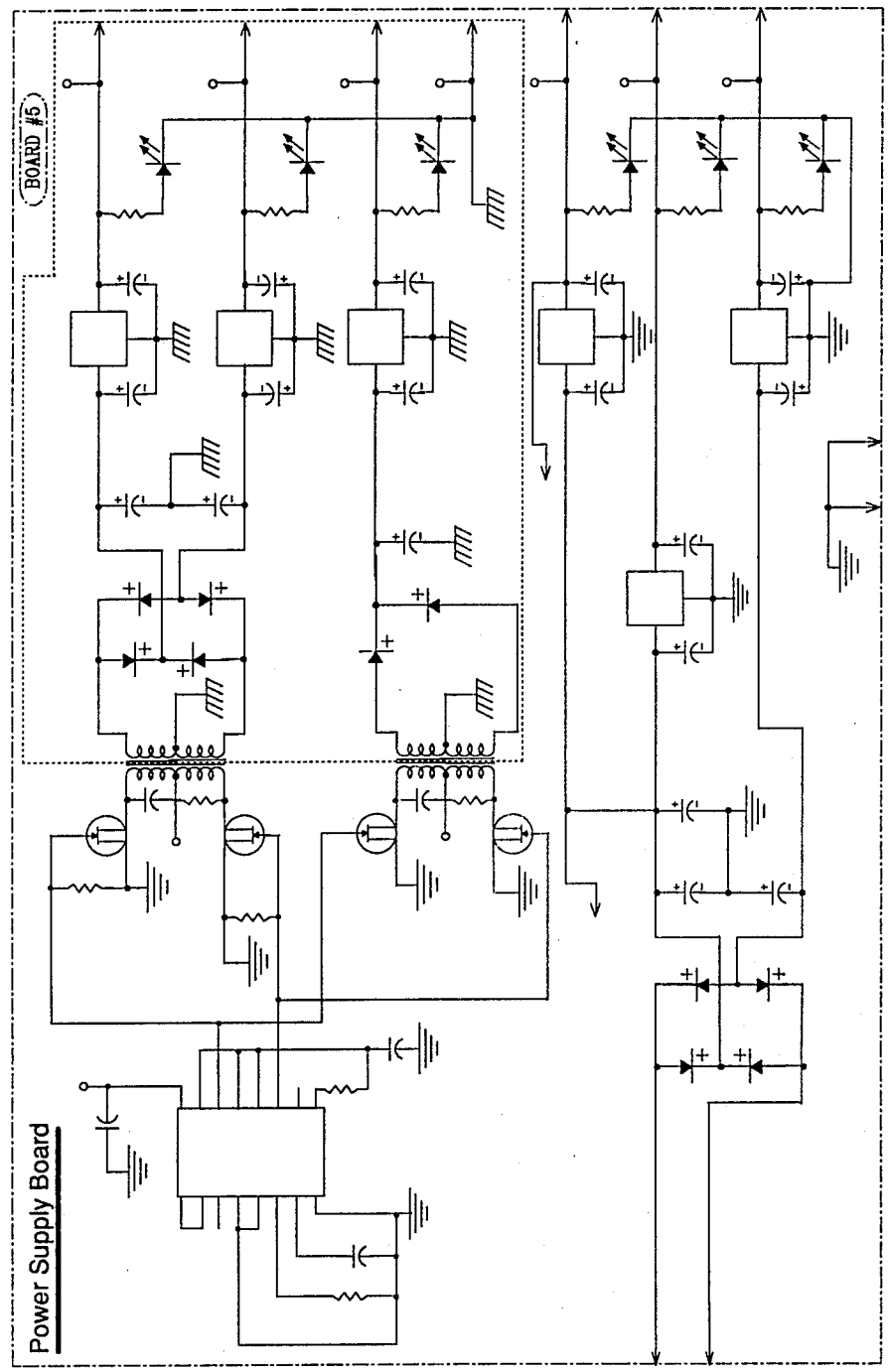
Figure 17G:
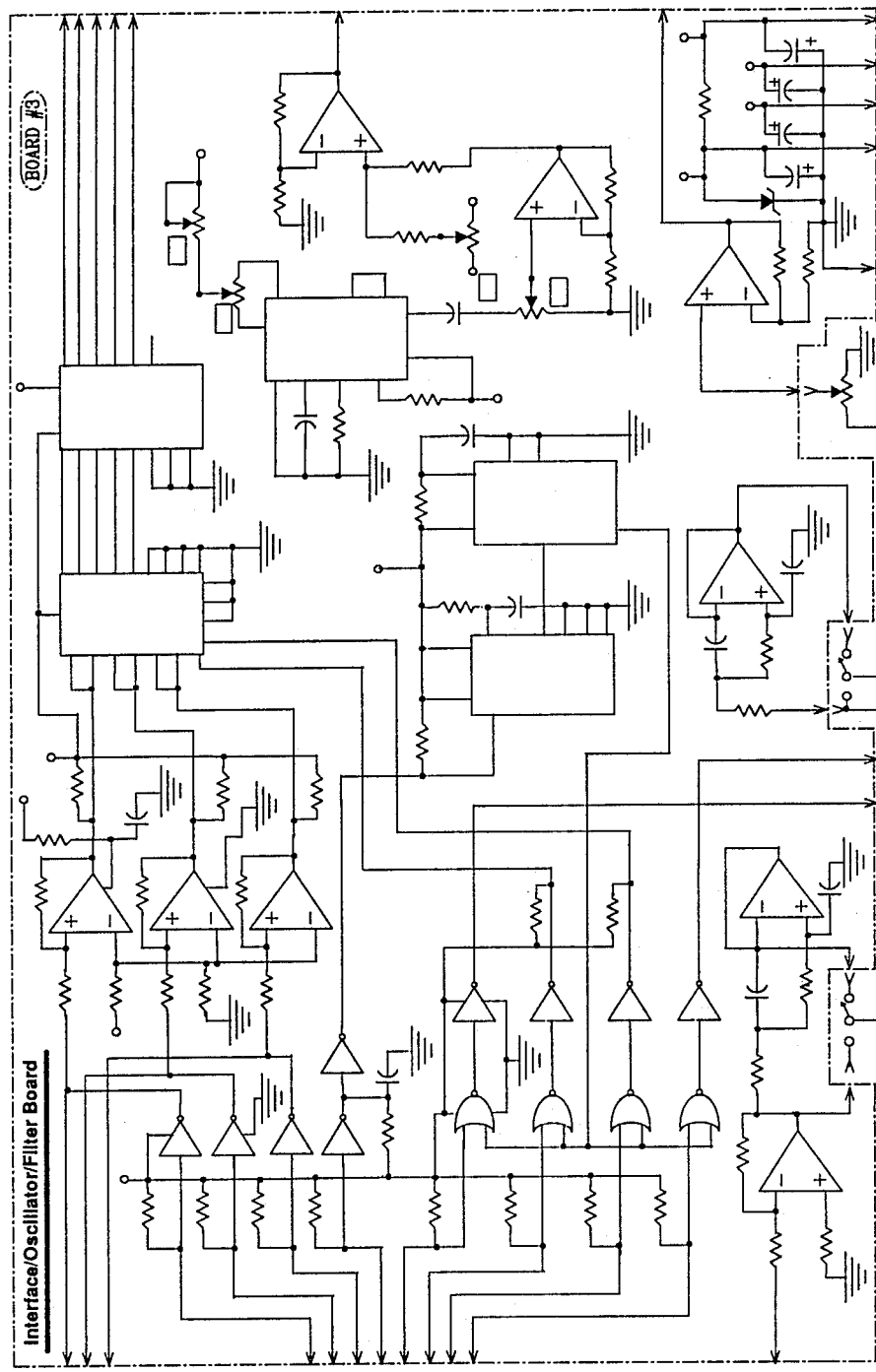
Figure 17H:
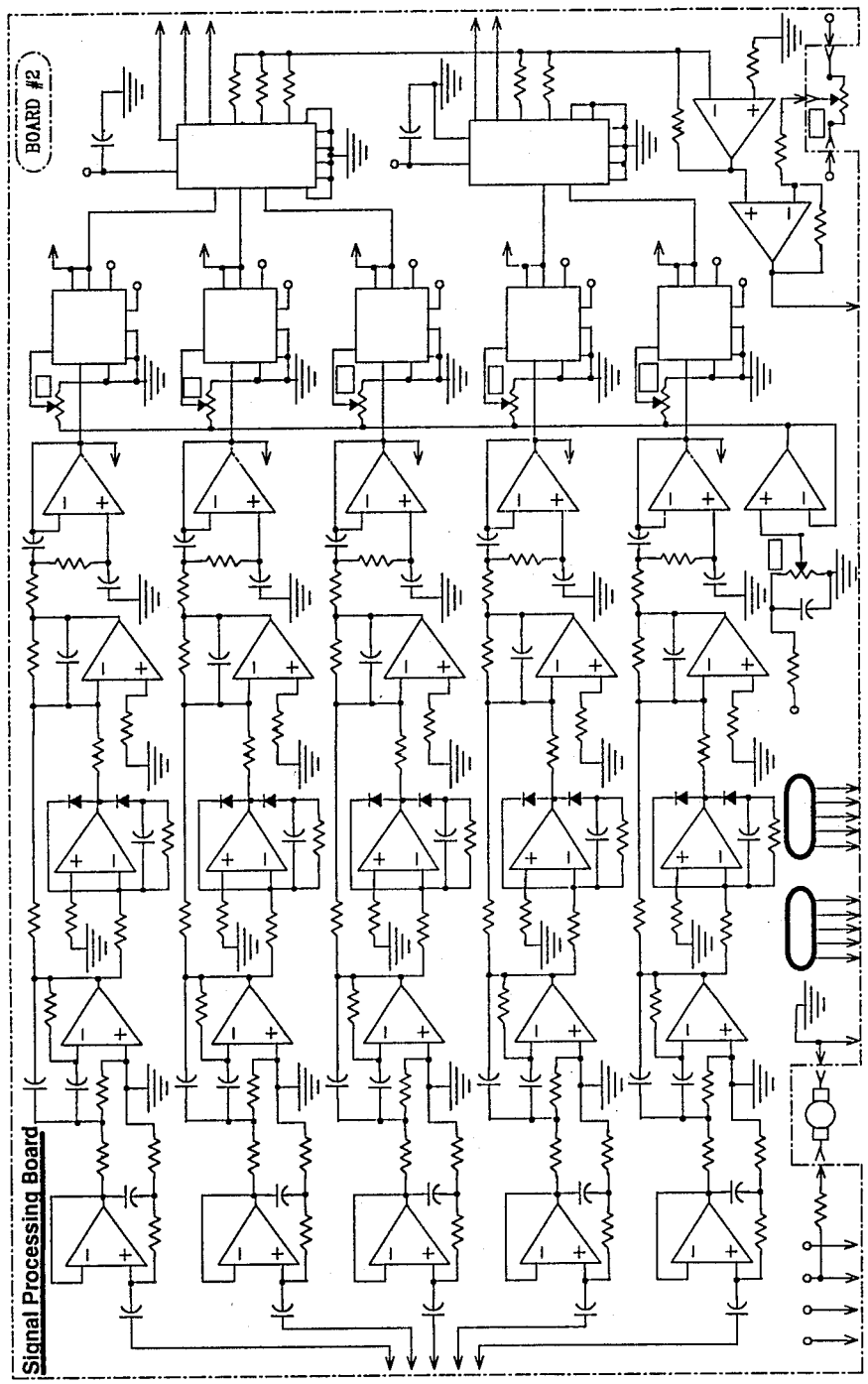
Figure 17I:
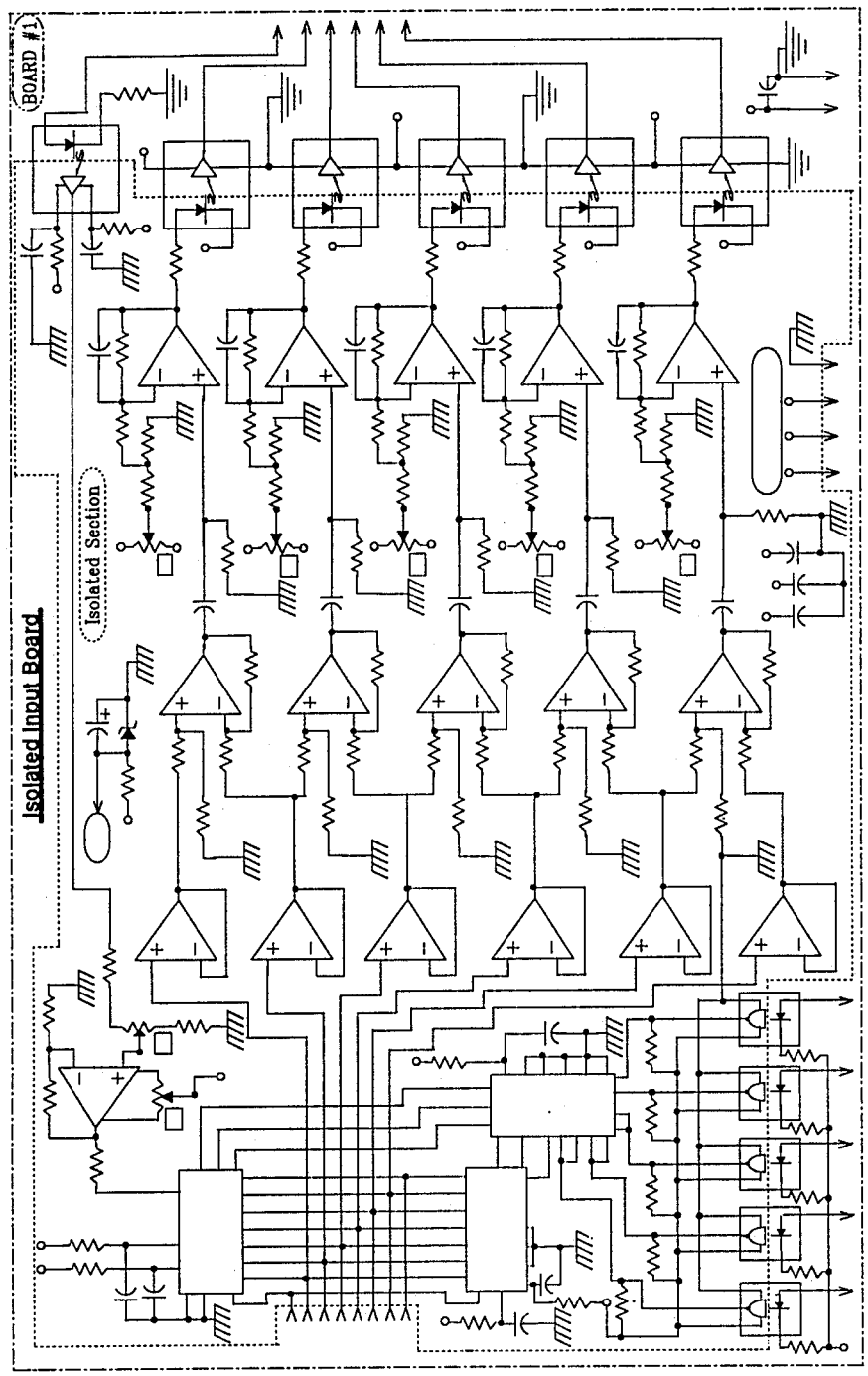

The computation of the volume of the right ventricular segments (one is illustrated in FIG. 16) between selected pairs of sense electrodes is done according to the formula Volume=$(I_c \times \rho \times L^2)/V_{EE}$ where $I_c$ is a known constant current source, $\rho$ is the resistivity of the medium, L is the distance between electrodes and $V_{EE}$ is the measured end to end voltage. This formula is substantially accurate although it does not take into consideration the loss of current to surrounding tissue or the varying conductivity of blood.

If L is designated to be 1 cm., then each segment volume is directly proportional to $\rho/Z_{EE}$, where $Z_{EE}$ is the impedance of the blood volume in the measured segment and is equal to $I_c/V_{EE}$. Using the thermodilution technique, $\rho$ can be determined as well as any signal losses due to the leakage of drive current through surrounding tissue. Thus, the total ventricular volume, i.e. the sum of the segments, can be determined by the formula $V_T = K \, \Sigma 1/Z_{EE}$ where K is a constant which represents the effects of blood resistivity and drive signal losses.

It should be appreciated that the potential from each sensing electrode pair can also be used to detect the position of the catheter within the cardiovascular system. The dynamic potentials from the sensing pairs of electrodes are examined and the pair location is determined from the timing and waveform characteristics.

In the present system, the current source for the electrodes is a sinusoidal waveform of approximately 20 microamperes at a frequency of approximately 2 KHz. Twenty (20) microamperes has been determined to be the maximum RMS safe current at 2 KHz by the Association for the Advancement of Medical Instrumentation.

It should also be appreciated that the construction of the inventive system allows any electrode to be a sense electrode or a drive electrode as desired and selected.

This invention has been described with reference to a preferred embodiment, obviously modifications and alterations will occur to others upon the reading and understanding of this specification. It is intended that all such modifications and alterations be included insofar as they come within the scope of the appended claims or the equivalents thereof.

What is claimed is:

1. A diagnostic catheter for use in measuring cardiac output in the right ventricular chamber comprising:
   (a) an elongated, multi-lumen, flexible member having a distal end and a proximal end, a first lumen extending the entire length of said member and terminating in a distal port, a second port extending through the side wall of said member at a location immediately proximate of said distal end of said flexible member and a second lumen extending from said proximal end of said member to said second port;
   (b) an expandable sleeve surrounding said member and spanning said second port, said sleeve inflatable by a fluid introduced into the proximal end of said second lumen;
   (c) a plurality of ring electrodes secured to the outer surface of said member at predetermined axial spacing including a distal ring electrode located a first predetermined distance proximal of said distal end of said flexible member, a proximal ring electrode located a second predetermined distance greater than said first predetermined distance from said distal end of said flexible member and a further plurality of intermediate ring electrodes disposed between said distal ring electrode and said proximal ring electrode;
   (d) a plurality of electrical conductors extending longitudinally through a third lumen in said flexible member from said proximal end of said flexible member and individually connected to separate ones of said plurality of ring electrodes; and,
   (e) a first stiffening member disposed in a fourth lumen in said flexible member and extending from a third predetermined distance to a fourth predetermined distance proximal of said distal end of said flexible member, said third and fourth distances being greater than said second predetermined distance.

2. The diagnostic catheter as in claim 1 and further including a fifth lumen extending from said proximal end of said flexible member and terminating in a third port formed through the side wall of said flexible member and located within said first predetermined distance; and a thermistor element exposed to heat conduction through said third port and having conductor means extending therefrom through said fifth lumen to the proximal end of said flexible member.

3. The diagnostic catheter as in claim 2 wherein said third port containing said thermistor includes a plastic seal covering said thermistor, said plastic having a thermal conductivity property allowing said thermistor to detect a small temperature change rapidly.

4. The diagnostic catheter as in claim 1 and further including a fourth port extending through the side wall of said flexible member and communicating with said fourth lumen at a location proximal of said stiffening member.

5. The diagnostic catheter as in claim 1 and further including a multi-terminal electrical connector connected to said plurality of electrical conductors.

6. The diagnostic catheter as in claim 1 and further including valve means connected to the proximal end of said second lumen of said flexible member.

7. A catheter for measuring cardiac output, comprising:
   a catheter body having an outer periphery and a distal section terminating in a distal end and a proximal section terminating in a proximal end;
   a plurality of spaced electrodes secured to said body outer periphery along said body distal section;
   a plurality of electrical leads, each one extending in said catheter body from a respective one of said electrodes to said proximal end of said catheter body; and
   an elongated rigid means for stiffening a portion of said catheter body, a distal end of said rigid means being located proximally of a proximal-most of one said plurality of electrodes, said rigid means being located proximally of said plurality of electrodes in order to allow them to be spaced away from endocardial tissue when said catheter body is correctly located in a heart.

8. The catheter of claim 7 further comprising a first lumen extending longitudinally through said catheter body from said body proximal end to a distal-most one of said plurality of electrodes, wherein said plurality of electrical leads are located in said first lumen.

9. The catheter of claim 8 further comprising a second lumen which extends from a proximal end of said catheter body to a port located at approximately 15 cm from said distal end of said catheter body.

10. The catheter of claim 9 further comprising:
   a balloon sleeve located adjacent a distal tip of said catheter body;

a third lumen communicating said balloon with said proximal end of said catheter body; and, a fourth lumen extending from said catheter body proximal end to a port located on said catheter body distal end.

11. The catheter of claim 10 further comprising a fifth lumen extending from said body proximal end and terminating in a port formed through side wall of said body and located at a predetermined distance from a proximalmost one of said plurality of electrodes.

12. The catheter of claim 7 further comprising:

a thermistor sensor secured to said catheter body and spaced distally from a distal-most one of said plurality of electrodes; and, an electrical lead extending in said catheter body from said thermistor to said proximal end of said catheter body.

13. The catheter of claim 7 wherein said plurality of electrodes comprises ten electrodes which are spaced apart from each other by approximately 0.8 to 1.0 cm and wherein a distal-most one of said plurality of electrodes is located at approximately 9 cm from said distal end of said catheter body.

14. The catheter of claim 7 wherein said stiffening means comprises an elongated stylet disposed in a lumen of the catheter, said stylet extending proximally from adjacent a proximal-most one of said plurality of electrodes.

15. The catheter of claim 7 further comprising a pair of drive electrodes, wherein a distal electrode and a proximal electrode of said plurality of electrodes serve as said pair of drive electrodes and wherein said stiffening means so locates said distal electrode and said proximal electrode as to be positioned adjacent a pulmonic valve and a tricuspid valve of the heart, respectively.

16. The catheter of claim 7 further comprising a terminal means secured to said catheter body proximal end for receiving a free end of each of said plurality of electrical leads.

17. A catheter for measuring cardiac output, comprising:

an elongated flexible multi-lumen catheter body having an outer periphery and a distal section terminating in a distal end and a proximal section terminating in a proximal end;

a balloon attached to said distal end of said body;

a first lumen extending the entire length of said catheter body and terminating in a first port which communicates with an interior surface of said balloon;

a plurality of spaced electrodes secured to said body outer periphery along said body distal section proximal of said balloon;

a second lumen extending from a distal most one of said plurality of spaced electrodes to said proximal end of said body;

a plurality of electrical leads, each one extending through said second lumen from a respective one of said electrodes to said proximal end of said catheter body; and, a means for taking blood pressure measurements in a right ventricle of a heart when the catheter is fully inserted in the heart, said means comprising a third lumen which extends longitudinally in said catheter body from said proximal end to a second port intermediate said plurality of spaced electrodes, wherein said second port is adapted to take blood pressure measurements as the port passes through a tricuspid valve and becomes stationary in the right ventricle of the heart.

18. The catheter of claim 17 further comprising:

a fourth lumen which extends longitudinally in said catheter body from said proximal end to a third port which is located proximally of said plurality of spaced electrodes; and, a stiffening member disposed in said fourth lumen distally of said third port.

19. The catheter of claim 17 further comprising a thermistor sensor secured to said catheter body and spaced proximally from said balloon.

20. The catheter of claim 17 wherein ten ring electrodes are provided which are spaced apart from each other by approximately 0.8 to 1.0 cm and wherein a distal-most one of said plurality of electrodes is located at approximately 9 cm from said distal end of said catheter body.

21. The catheter of claim 17 further comprising a multi-terminal electrical connector connected to said plurality of electrical leads.

* * * * *